United States Patent [19]

Zimmerman

[11] Patent Number: 4,487,626

[45] Date of Patent: Dec. 11, 1984

[54] HERBICIDAL SULFONAMIDES

[75] Inventor: William T. Zimmerman, Landenberg, Pa.

[73] Assignee: E. I. Du Pont de Nemours and Company, Wilmington, Del.

[21] Appl. No.: 286,159

[22] Filed: Jul. 27, 1981

Related U.S. Application Data

[63] Continuation-in-part of Ser. No. 180,482, Aug. 22, 1980, abandoned.

[51] Int. Cl.$^3$ .................. A01N 9/14; C07D 491/048
[52] U.S. Cl. ................................. 71/90; 71/92; 544/117; 544/278
[58] Field of Search ............... 71/92, 90; 544/278, 544/117

[56] References Cited

U.S. PATENT DOCUMENTS

| | | | |
|---|---|---|---|
| 3,520,887 | 7/1970 | Heerdt et al. | 544/278 |
| 4,159,377 | 6/1979 | Temple, Jr. | 544/278 |
| 4,169,719 | 10/1979 | Levitt | 544/320 |
| 4,191,553 | 3/1980 | Reap | 71/92 |
| 4,199,584 | 4/1980 | Cox et al. | 544/278 |

FOREIGN PATENT DOCUMENTS

| | | | |
|---|---|---|---|
| EP0015683 | 9/1980 | European Pat. Off. | 544/278 |
| 1443336 | 11/1969 | Fed. Rep. of Germany | 544/278 |

OTHER PUBLICATIONS

Van Den Bos et al., "Rec. Irav. Chim. Pays-Bas," vol. 79, 1960, pp. 807–824.
Chem. Abstr., 80, 96012f (1974).
Bull. Soc. Chim. Fr., 803 (1969), Bi sagni et al.
Chem. Ber., 106, 874 (1973), Wolfers et al.
Chem. Ber., 99 (3), 1002 (1966), Gewald.

Primary Examiner—Glennon H. Hollrah
Assistant Examiner—James H. Turnipseed

[57] ABSTRACT

This invention relates to a novel class of arylsulfonylureidofuro[2,3-d]pyrimidines, such as N'-[(4,6-dimethylfuro[2,3-d]pyrimidin-2-yl)aminocarbonyl]-N,N-dimethylbenzene-1,2-sulfonamide, and their use as herbicides and plant growth regulants. These novel compounds can be prepared by reacting an appropriate furo[2,3-d]pyrimidin-2-amine with an appropriately substituted arylsulfonyl isocyanate or isothiocyanate.

40 Claims, No Drawings.

HERBICIDAL SULFONAMIDES

RELATED APPLICATIONS

This application is a continuation-in-part of my copending application Ser. No. 180,482, filed Aug. 22, 1980, now abandoned.

BACKGROUND OF THE INVENTION

This invention relates to a novel class of arylsulfonylureidofuro[2,3-d]pyrimidines and their use as herbicides and plant growth regulants.

In U.S. Pat. No. 4,199,584, compounds of the following type are taught as pesticides:

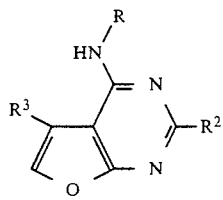

U.S. Pat. No. 4,169,719, issued Oct. 2, 1979 to George Levitt, teaches arylsulfonylureidopyrimidines such as N-[(4,6-dimethylpyrimidin-2-yl)aminocarbonyl]-2-chlorobenzenesulfonamide.

In U.S. Pat. No. 4,191,553, there is a disclosure of compounds having the formula:

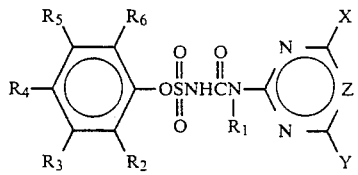

wherein
$R_1$ is H, $OCH_3$ or alkyl of 1-3 carbons;
$R_2$ is H, Cl, F, Br, $NO_2$, alkyl of 1-4 carbons, alkoxy of 1-4 carbons,

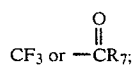

$R_3$ is H, Cl, F, Br, $CH_3$, or alkoxy of 1-4 carbons;
$R_4$ is H, Cl, F, Br, $NO_2$, alkyl of 1-4 carbons, alkoxy of 1-4 carbons,

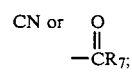

$R_5$ is H, Cl, F, Br, $CH_3$, $NO_2$ or $CF_3$;
$R_6$ is H, Cl, F, Br, alkyl of 1-4 carbons or alkoxy of 1-4 carbons;
$R_7$ is $Na+O—$, OH, or alkoxy of 1-4 carbons;
X is $CH_3$, $CH_3CH_2$, alkoxy of 1-3 carbons, $CH_3OCH_2$, $CH_3OCH_2CH_2O$, $CH_3S$, $CH_3CH_2S$, $CF_3$ or Cl;
Y is $CH_3$, $CH_3CH_2$, alkoxy of 1-3 carbons, $CH_3OCH_2$, $CH_3OCH_2CH_2O$, $CH_3S$ or $CH_2CH_3S$; and
Z is CH or N;
provided that only one of $R_2$, $R_3$ or $R_4$ is alkoxy; and
when $R_5$ is $NO_2$, $R_4$ is other than $NO_2$.

Unexamined European Pat. No. 7687, teaches arylsulfonylureidopyrimidines such as N-[(4,6-dimethylpyrimidin-2-yl)aminocarbonyl]-2-methoxycarbonylbenzenesulfonamide.

In the Bull. Soc. Chim. Fr., 803 (1969), the authors, Bisagni etc. teach the compound 2-amino-4,6-dimethylfuro[2,3-d]pyrimidine.

In Chem. Ber., 106, 874 (1973), Wolfers et al. teach 2-amino-6-phenylfuro[2,3-d]pyrimidines.

In addition, 4-aminofuro[2,3-d]pyrimidines are well known in the art, see for example, Japan. Kokai 73 78,199 [Chem. Abstr. 80 96012f (1974)] wherein the following is taught:

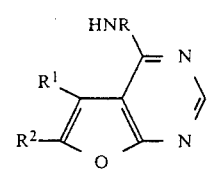

In Chem. Ber., 99 (3), 1002 (1966), the following compound is taught:

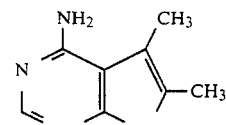

The presence of undesired vegetation causes substantial damage to useful crops, especially agricultural products that satisfy man's basic food needs, such as rice, corn, wheat, soybean and the like. The current population explosion and concomitant world food shortage demand improvements in the efficiency of producing these crops. Preventing or minimizing the loss of a portion of such valuable crops by killing or inhibiting the growth of undesired crops is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

This invention relates to novel compounds of Formula I and their agricultural salts, suitable agricultural compositions containing them, and their method of use as general and selective herbicides having both preemergence and postemergence activity and as plant growth regulants.

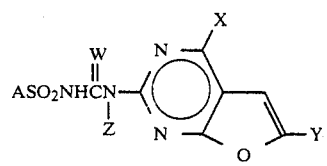

where A is

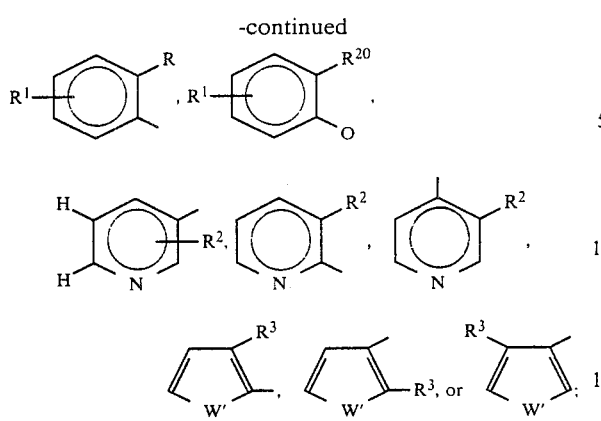

R is H, $C_1$-$C_4$ alkyl, $C_2$-$C_4$ alkenyl, $C_5$-$C_6$ cycloalkenyl, phenyl, phenyl substituted with one Cl or $CH_3$ group, $C_1$-$C_4$ alkoxy, F, Cl, Br, $NO_2$, $NH_2$, CN, $CF_3$, $C(O)R_4$, $S(O)_mR^5$, $SO_2NR^6R^7$, $SO_2N(OCH_3)CH_3$, $SO_2OCH_2CF_3$, $SO_2OCH_2CCl_3$, $BR^8$, $OSO_2R^9$, $CH_2L$ or $CH(CH_3)L$;

Z is H or $CH_3$;

$R^1$ is H, F, Cl, Br, $CF_3$, $C_1$-$C_4$ alkyl, $C_1$-$C_4$ alkoxy or $NO_2$;

$R^4$ is H, $C_1$-$C_3$ alkyl, $C_1$-$C_6$ alkoxy, benzyloxy, $C_3$-$C_6$ alkenyloxy, $C_3$-$C_6$ alkynyloxy, $C_2$-$C_6$ haloalkoxy substituted with 1-3 atoms selected from F, Cl or Br, $C_5$-$C_6$ cycloalkoxy, $O(CH_2CH_2O)_nR^{10}$, $OCH_2CH_2CH_2OR^{10}$, $OCH_2OR^5$, $OCH_2OCH_2CH_2OR^{10}$, $NR^{11}R^{12}$ or $C_1$-$C_4$ alkylthio;

m is 0, 1 or 2;

n is 1 or 2;

$R^5$ is $C_1$-$C_4$ alkyl;

$R^6$ and $R^7$ are independently $C_1$-$C_4$ alkyl, provided that the total number of carbon atoms of $R^6$ and $R^7$ is less than or equal to 5;

B is O or $S(O)_m$;

$R^8$ is $CHF_2$, $CF_3$, $CH_2CF_3$ or $CF_2CHFG$ where G is F, Cl, Br or $CF_3$;

$R^9$ is $C_1$-$C_4$ alkyl, $CH_2CH_2OCH_3$, $CH_2CH_2CH_2OCH_3$, or $C_1$-$C_4$ alkyl substituted with 1-3 atoms of F, Cl or Br;

L is Cl, Br, $C_1$-$C_4$ alkoxy, $C_3$-$C_4$ alkenyloxy, OH, $S(O)_mR^5$, $CO_2R^{17}$ or $SO_2N(CH_3)_2$;

$R^{10}$ is $CH_3$ or $C_2H_5$;

$R^{11}$ is H, $C_1$-$C_4$ alkyl, $OCH_3$ or

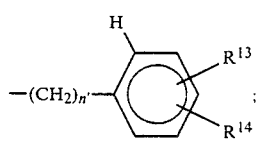

$R^{12}$ is H or $C_1$-$C_4$ alkyl;

$R^{11}$ and $R^{12}$ can also be taken together to form $-(CH_2)_4-$, $-(CH_2)_5-$ or $-CH_2CH_2OCH_2CH_2-$;

n' is 0 or 1;

$R^{13}$ is H, F, Cl, Br, $NO_2$, CN, $CF_3$, $C_1$-$C_3$ alkyl, $OCH_3$ or $SCH_3$;

$R^{14}$ is H, F, Cl, Br, $CH_3$ or $OCH_3$;

$R^2$ is H, F, Cl, Br, $C_1$-$C_4$ alkyl, $C_1$-$C_4$ alkoxy, $NO_2$, $CO_2R^{15}$, $S(O)_mR^{16}$, $SO_2NR^{18}R^{19}$ or $SO_2N(OCH_3)CH_3$;

$R^{15}$ is $C_1$-$C_4$ alkyl;

$R^{16}$ is $C_1$-$C_3$ alkyl;

$R^{17}$ is $C_1$-$C_4$ alkyl, $C_3$-$C_4$ alkenyloxy, $CH_2CH_2OCH_3$ or $CH_2CH_2Cl$;

$R^{18}$ and $R^{19}$ are independently $CH_3$ or $C_2H_5$;

W' is O or S;

$R^3$ is $C_1$-$C_4$ alkyl, $C_1$-$C_4$ alkoxy, H, F, Cl, Br, $NO_2$, $SO_2MR^6R^7$, $SO_2N(OCH_3)CH_3$ or $C(O)R^4$;

$R^{20}$ is F, Cl, Br, $CO_2R^{17}$, $OSO_2R^9$, $No_2$, $C_1$-$C_4$ alkyl or $C_1$-$C_4$ alkoxy;

W is O or S;

X is $CH_3$, $C_2H_5$, Cl, $OCH_3$, $OC_2H_5$, $N(CH_3)_2$ or $SCH_3$;

Y is H, $CH_3$ or $C_2H_5$;

and their agriculturally suitable salts; provided that
(a) when $R^{11}$ is $OCH_3$; then $R^{12}$ is $CH_3$;
(b) if $R^1$ is other than H and R is H, then $R^1$ cannot be in the 4-position of the benzene ring;
(c) when $R^{11}$ is

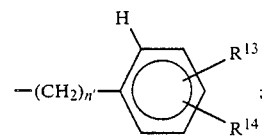

then $R^{12}$ is H or $CH_3$; and
(d) when W' is O, then $R^3$ is $CO_2R^{17}$.

Preferred for reasons of higher herbicidal activity and/or more favorable ease of synthesis are:

(1) Compounds of the generic scope where
W is O;
Y is $CH_3$;
X is other than Cl;
A is other than

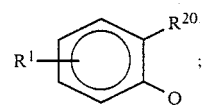

and
Z is H;

(2) Compounds of Preferred (1) where
X is $CH_3$ or $OCH_3$; and
A is

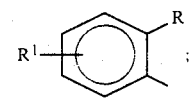

(3) Compounds of Preferred (1) where
X is $CH_3$ or $OCH_3$; and
A is

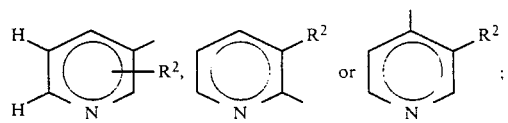

(4) Compounds of Preferred (1) where
X is $CH_3$ or $OCH_3$; and
A is

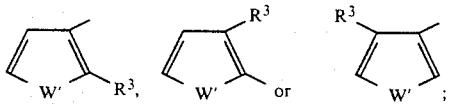

(5) Compounds of Preferred (2) where
R is $C_1-C_3$ alkyl, $OCH_3$, F, Cl, Br, $NO_2$, $CF_3$, $C(O)R^4$, $S(O)_mR^5$, $SO_2NR^6R^7$, $SO_2N(OCH_3)CH_3$, $BR^8$, $OSO_2R^9$ or $CH_2L$;
$R^4$ is H, $C_1-C_3$ alkyl, $C_1-C_4$ alkoxy, $C_3-C_4$ alkenyloxy, haloethoxy containing 1-3 atoms of F or Cl, $OCH_2CH_2OR^{10}$, $OCH_2CH_2CH_2OR^{10}$, $OCH_2OR^5$, $OCH_2OCH_2CH_2OR^{10}$, $NR^{11}R^{12}$ or $C_1-C_4$ alkylthio;
B is O;
L is $OCH_3$ or $CO_2R^{17}$;
$R^{11}$ is $C_1-C_4$ alkyl or $OCH_3$;
$R^{12}$ is $C_1-C_4$ alkyl; and
$R^{11}$ and $R^{12}$ can be taken together to form $-(CH_2)_4-$, $-(CH_2)_5-$ or $-CH_2CH_2OCH_2CH_2-$,
provided that the total carbon atoms of $R^{11}$ and $R^{12}$ is less than or equal to 5;
(6) Compounds of Preferred (5) where
$R^1$ is H;
$R^4$ is $C_1-C_4$ alkoxy, $C_3-C_4$ alkenyloxy, $OCH_2CH_2Cl$ or $OCH_2CH_2OCH_3$;
$R^8$ is $CF_3$, $CH_2CF_3$ or $CF_2CHF_2$;
$R^9$ is $CH_3$; and
L is $OCH_3$;
(7) Compounds of Preferred (6) where
R is $NO_2$, $C(O)R^4$, $SO_2R^5$ or $SO_2N(CH_3)_2$;
$R^4$ is $C_1-C_3$ alkoxy; and
$R^5$ is $C_1-C_3$ alkyl;
(8) Compounds of preferred (3) where
A is

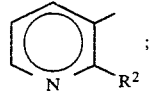

and
$R^2$ is Cl, Br, $CH_3$, $OCH_3$ or $S(O)_mCH_3$;
(9) Compounds of Preferred (4) where
W' is S;
$R^3$ is H, $CH_3$, Cl, Br or $C(O)R^4$; and
$R^4$ is $C_1-C_3$ alkoxy.

Specifically Preferred for highest herbicidal activity and/or most favorable ease of synthesis are:

2-Chloro-N-[(4,6-dimethylfuro[2,3-d]pyrimidin-2-ylaminocarbonyl]benzenesulfonamide, m.p. 200°-201° (d);
N-[(4,6-Dimethylfuro[2,3-d]pyrimidin-2-yl)aminocarbonyl]-2-nitrobenzenesulfonamide, m.p. 204°-205° (d);
2-[(4,6-Dimethylfuro[2.3-d]pyrimidin-2-yl)aminocarbonyl]aminosulfonyl benzoic acid, methyl ester, m.p. 197°-198° (d);
2-[(4,6-Dimethylfuro[2,3-d]pyrimidin-2-yl)aminocarbonyl]aminosulfonyl benzoic acid, (2-propenyl)ester, m.p. 185°-186° (d);
2-[(4,6-Dimethylfuro[2,3-d]pyrimidin-2-yl)aminocarbonyl]aminosulfonyl benzoic acid, (1-methylethyl)ester, m.p. 196°-197° (d);
2-Chloro-N-[(4,6-dimethylfuro[2,3-d]pyrimidin-2-yl)aminocarbonyl]-3-pyridinesulfonamide, m.p. 206°-207° (d);
3-[(4,6-Dimethylfuro[2,3-d]pyrimidin-2-yl)aminocarbonyl]aminosulfonyl-2-thiophenecarboxylate, methyl ester, m.p. 202°-203° (d);
N-[(4,6-Dimethylfuro[2,3-d]pyrimidin-2-yl)aminocarbonyl]-3-methyl-2-thiophenesulfonamide;
4-[(4,6-Dimethylfuro[2,3-d]pyrimidin-2-yl)aminocarbonyl]aminosulfonyl-3-thiophenecarboxylate, methyl ester;
2-[[(4,6-Dimethylfuro[2,3-d]pyrimidin-2-yl)aminocarbonyl]aminosulfonyl]benzoic acid, ethyl ester, m.p. 193°-195° (d);
2-[[(4-Methoxy-6-methylfuro[2,3-d]pyrimidin-2-yl)aminocarbonyl]aminosulfonyl]benzoic acid, methyl ester, m.p. 216°-218°;
N-[(4,6-Dimethylfuro[2,3-d]pyrimidin-2-yl)aminocarbonyl]-2-methylsulfonylbenzenesulfonamide, m.p. 208°-210° (d); and
N'-[(4,6-Dimethylfuro[2,3-d]pyrimidin-2-yl)aminocarbonyl]-N,N-dimethyl-benzene-1,2-sulfonamide, m.p. 199°-202°.

This invention also relates to novel compounds of Formula II-V which are useful intermediates for the herbicidal compounds of Formula I.

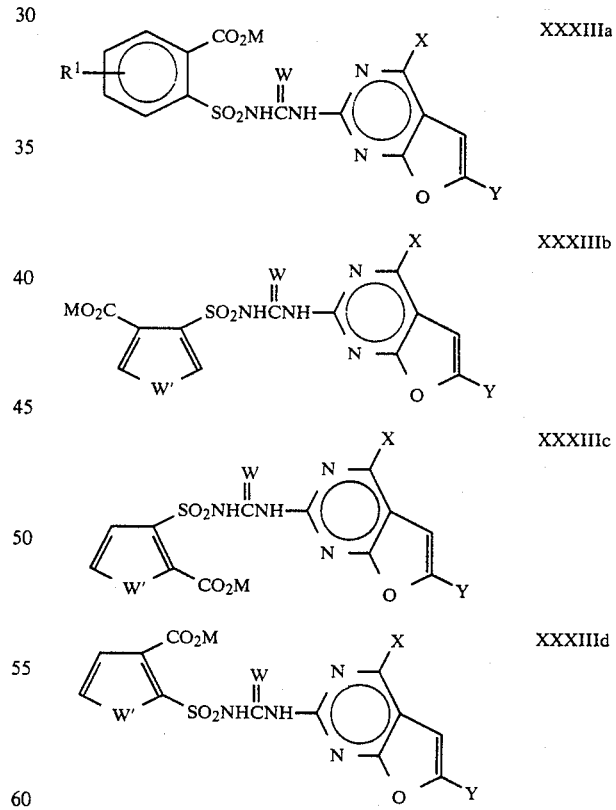

wherein
$R^1$ is H, F, Cl, Br, $CF_3$, $C_1-C_4$ alkyl or $C_1-C_4$ alkoxy;
M is H or an alkali metal;
W' is O or S;
W is O or S;
X is $CH_3$, $C_2H_5$, $OCH_3$ or $OC_2H_5$; and
Y is H, $CH_3$ or $C_2H_5$.

This invention also relates to a process preparing compounds of Formula VI

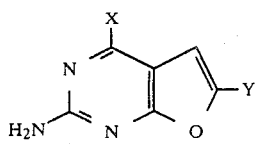

wherein X and Y are independently CH₃ or C₂H₅; which comprises contacting a keto-ester of the formula

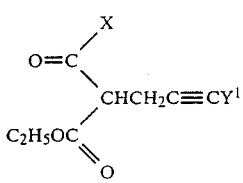

wherein Y¹ is H or CH₃; with an excess of guanidine carbonate in a polar aprotic solvent at a temperature in the range of about 80° to 200° and isolating the reaction product.

This invention also relates to a process for preparing compounds of Formula IIIb

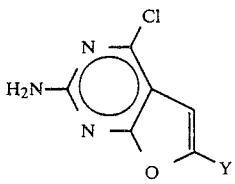

wherein Y is CH₃ or C₂H₅; which comprises contacting a dichloropyrimidine of the formula

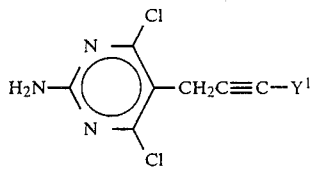

wherein Y¹ is H or CH₃; with two molar equivalents of an alkali metal hydroxide in a solvent medium comprised of water and a water-miscible organic solvent at a temperature in the range of 50° to 125° and isolating the reaction product.

Synthesis

Many of the compounds of Formula I can be prepared by reacting an appropriate furo[2,3-d]pyrimidin-2-amine of Formula III with an appropriately substituted sulfonyl isocyanate or isothiocyanate of Formula II, as shown in Equation 1:

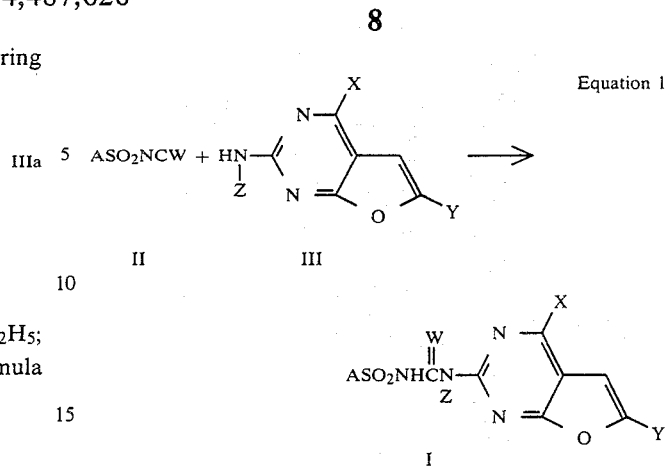

wherein
A, W, X, Y and Z are as previously defined except in the following instances:
where R is NH₂, CN, S(O)R⁵, CH₂OH, CH₂S(O)R⁵, CH(CH₃)OH, CH(CH₃)S(O)R⁵; or
where R² is S(O)R¹⁶; or
where R⁴ is H, C₁-C₃ alkyl, OCH₂OR⁵, C₃-C₆ alkynyloxy, OCH₂OCH₂CH₂OR¹⁰, NR¹¹R¹² or C₁-C₄ alkylthio.

In those instances, the compounds may be prepared from appropriately substituted compounds of Formula I in one or more steps and will be described below in part C: Special Preparations.

The reaction of Equation 1 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of the aminopyrimidine. Since such isocyanates and isothiocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether and filtration.

A. Sulfonyl Isocyanate or Isothiocyanate Intermediates

The intermediate aryl sulfonyl isocyanates of Formula II (W=O) can be prepared by reacting corresponding aryl sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI, p. 223–241, Academic Press, New York and London, W. Foerst Ed. The intermediates pyridyl sulfonyl isocyanate of Formula II (W=O) can be prepared by reacting an N-(alkylaminocarbonyl)pyridinesulfonamide with phosgene as described in unexamined European Pat. No. 13,480, the disclosure of which is hereby incorporated by reference. The N-(alkylaminocarbonyl)pyridinesulfonamide can be prepared as described in unexamined European Pat. No. 13,480, by the reaction of a pyridinesulfonamide, an alkyl isocyanate and an anhydrous base in an anhydrous solvent.

Similarly, the thiophene and furan sulfonyl isocyanates can be prepared as described in British Pat. No. 2,065,116 A (published June 24, 1981) and shown in equation 2, wherein $R^4$ and W' are as defined above.

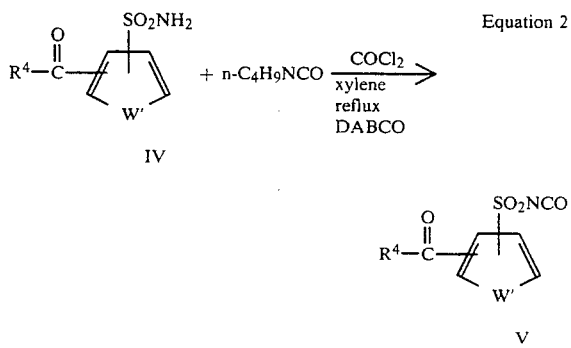

A mixture of the appropriate sulfonamide, e.g. an 2-alkoxycarbonyl-3-thiophene sulfonamide IV such as the methyl ester, which is known in the art, an alkyl isocyanate such as butyl isocyanate and a catalytic amount of 1,4-diaza[2.2.2]bicyclooctane (DABCO) in xylene or other inert solvent of sufficiently high boiling point (e.g. >135°) is heated to approximately 130°-150° C. Phosgene is added to the mixture until an excess of phosgene is present as indicated by a drop in the boiling point. After the mixture is cooled and filtered to remove a small amount of insoluble by-products, the solvent and alkyl isocyanate are distilled off in-vacuo leaving a residue which is the crude sulfonyl isocyanate V.

The preparation of sulfonamides from ammonium hydroxide and sulfonyl chloride is widely reported in the literature, e.g., Crossley et al., *J. Am. Chem. Soc.* 60, 2223 (1938). The preparation of pyridylsulfonamide is described in G. Machek, *Monatsch* 2, 84 (1939) and L. Thunus and C. L. Lapiere, *Ann. Farn* 33, 663 (1975).

Certain sulfonyl chlorides are best prepared by chlorosulfonation of a substituted benzene in carbon tetrachloride according to the teaching of H. T. Clarke et al., *Org. Synth.* Coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960). The preparation of pyridyl sulfonyl chlorides is described in *Chem. Abs.* 88, 190603 m (1978).

Arylsulfonylisothiocyanates of Formula II (W=S) can be prepared by treatment of sulfonamides with carbon disulfide and potassium hydroxide followed by reaction of the dipotassium salt with phosgene according to the teaching of K. Hartke, *Arch. Pharm.* 229, 174 (1966).

Pyridine sulfonylisothiocyanates can be prepared according to the procedure taught by K. Dickere and E. Kuhle in U.S. Pat. No. 3,346,590. A suitable pyridinesulfonyliminodithiocarbonate is reacted with phosgene in the presence of a solvent such as toluene or xylene.

The thiophene sulfonylisothiocyanate intermediates of Formula VI, prepared according to Equation 3 and 4, are useful for the preparation of compounds of Formula I where W=S and A is a thiophene ring.

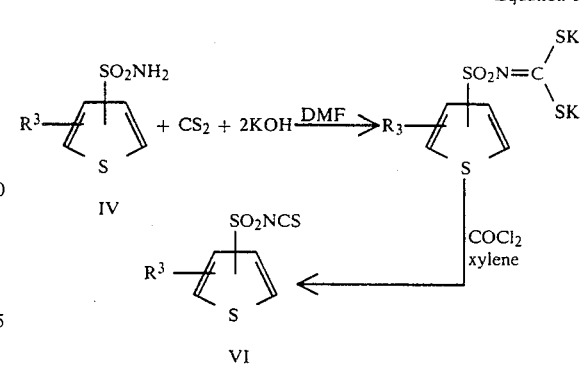

The substituted thiophenesulfonamide is dissolved in dimethylformamide (DMF) with an equivalent amount of carbon disulfide and two equivalents of potassium hydroxide are added portionwise at room temperature. The mixture is stirred for 1-8 hours and diluted with ethyl acetate, ethyl ether or similar aprotic solvent to cause the dipotassium salt of the dithiocarbamic acid to precipitate. The salt is isolated, dried and suspended in an inert solvent such as xylene, benzene, carbon tetrachloride or methylene chloride. Phosgene is added to the stirred suspension at below room temperature and the mixture stirred for 1-3 hours. In place of phosgene, a chloroformic ester (e.g. methyl chloroformate), phosphorous pentachloride, sulfuryl chloride or thionyl chloride can be used.

The sulfonylisothiocyanate which is formed is usually soluble in the solvent and is isolated filtering off the insoluble potassium chloride and concentrating the filtrate. These isothiocyanates tend to be unstable and dimerize readily, (Equation 4) however, the dimers can be used in the same manner as the parent isothiocyanates for the purposes of this invention.

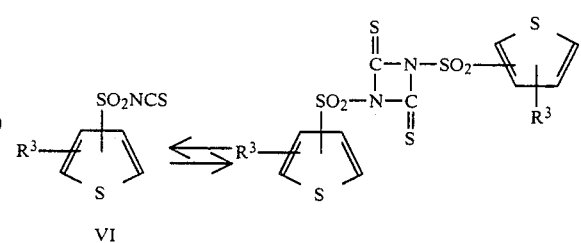

The method used for preparing the intermediate sulfonamides when R or $R^3$ is $SO_2NR^6R^7$ is illustrated in Equations 5a-d.

Equations 5a-d

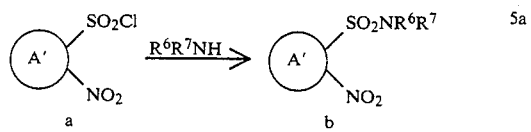

-continued
Equations 5a–d

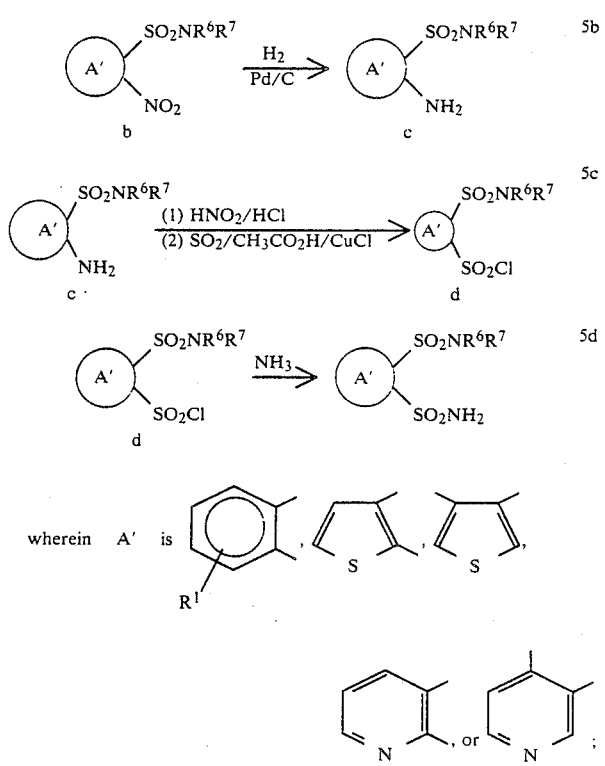

and $R^6$ and $R^7$ are as previously defined.

In step (5a), the o-nitrobenzenesulfonyl chlorides or nitrothiophenesulfonyl chlorides in Formula a, which are well-known in the art, are treated with an amine, $R^6R^7NH$, in an inert organic solvent such as methylene chloride, ethyl ether, or tetrahydrofuran at 0°–50°. The amine may be taken in excess to act as an acid acceptor; alternatively, a tertiary amine such as triethylamine or pyridine may be used as an acid acceptor. The by-product amine hydrochloride is filtered off or washed out of the solvent with water and the product isolated by evaporation of the solvent.

The reduction described in step (5b) is accomplished by treating a solution of the compounds of Formula b, in a solvent such as ethanol, ethyl acetate, or DMF, in a pressure vessel with 100–1000 pounds per square inch of hydrogen at 80°–150° in the presence of a hydrogenation catalyst such as 5–10% palladium adsorbed on carbon. When the theoretical amount of hydrogen has been absorbed, the solution is cooled and the catalyst is removed by filtration. The product is then isolated by evaporation of the solvent.

The diazotization and coupling with sulfur dioxide, described in step (5c), is accomplished in the following manner. A solution of the sulfamoyl compound of Formula c in a mixture of concentrated hydrochloric acid and glacial acetic acid is treated with a solution of sodium nitrite in water at −5° to 0°. After stirring for 10–15 minutes at 0° to insure complete diazotization, this solution is added to a mixture of an excess of sulfur dioxide and a catalytic amount of cuprous chloride in glacial acetic acid at 0°–5°. The temperature is kept at 0°–5° for ¼ to 1 hour and is then raised to 20°–25° and held at that temperature for 2–4 hours. This solution is then poured into a large excess of ice water. The sulfonyl chloride products, d, can be isolated by filtration or by extraction into solvent such as ethyl ether or methylene chloride followed by evaporation of the solvent.

The amination described in step (5d) is conveniently carried out by treating a solution of the sulfonyl chloride of Formula d with an excess of anhydrous ammonia in a solvent such as ethyl ether or methylene chloride at 0°–25°. If the product sulfonamide is insoluble it may be isolated by filtration followed by washing out the salts with water. If the product sulfonamide is soluble in the reaction solution, it may be isolated by filtering off the precipitated ammonium chloride and evaporating the solvent.

The sulfonamide precursors to intermediates of Formula II in which R or $R^3$ is $SO_2OCH_2CF_3$, $SO_2OCH_2CCl_3$ or $SO_2N(CH_3)OCH_3$, or $R^2$ is $SO_2N(CH_3)OCH_3$ can be prepared through a sequence analogous to that shown in Equations 5a–d. In step 5a, the amine is replaced by the appropriate alkoxide salt or N-methoxy-N-methylamine and the resulting nitro compound is treated as in Equations 5b–d.

Equation 6 describes the preparation of intermediates of Formula II when R or $R^3$ is $S(O)_mR^5$, or $R^2$ is $S(O)_mR^{16}$ and where $m = 0$ or 2.

Equation 6

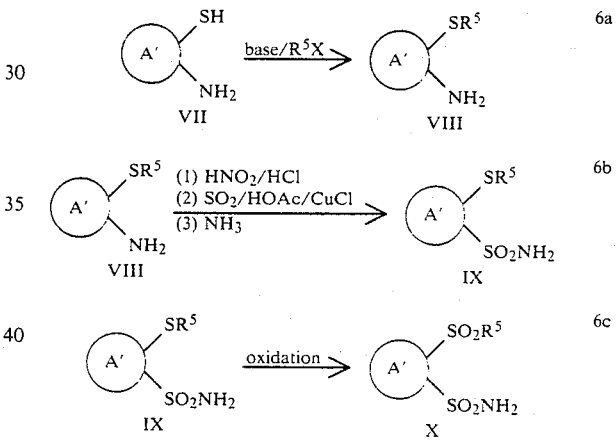

wherein $A'$, and $R^5$ are as previously defined.

The thioether of Formula VIII may be prepared from the appropriate 2-aminothiophenol or aminothiothiophene and an alkyl halide as described in the literature, e.g., R. N. Prasad et al., *Can J. Chem.* 44, 1247 (1966). The formation of the sulfonamide IX is analogous to that presented in Equations 5c and 5d above.

The oxidation of IX to the corresponding 2-alkylsulfonylbenzenesulfonamides or alkylsulfonylthiophenesulfonamides of Formula X may be carried out utilizing any of several of standard literature procedures with m-chloroperbenzoic acid (C. R. Johnson, et al., *Tetrahedron*, 25, 5649 (1969)), or with aqueous hydrogen peroxide in acetic acid (F. G. Bordwell, et al., *J. Amer. Chem. Soc.* 77, 1141, (1955).

Preparation of sulfonyl isocyanates and sulfonyl isothiocyanates of Formula II wherein R is $BR^8$ (B and $R^8$ are as previously defined) can be prepared by the methods described in unexamined European Pat. No. 23,422.

The compounds of this application in which R is a sulfonate derivative ($OSO_2R^9$) may also be prepared via the corresponding sulfonyl isocyanate or isothiocyanate of Formula II. Sulfonamides, prepared as described in Research Disclosure, pg. 52, (1978), may conveniently be converted to the corresponding isocyanates or isothiocyanates of Formula (II) by methods described above.

The preparation of intermediates II in which R is $CH_2L$ (where L is Cl, Br, alkoxy, alkenyloxy, alkylthio or alkylsulfonyl) may be accomplished from the corresponding sulfonamides by the methods described above. Many of these sulfonamides are available from the corresponding nitrobenzenes by reduction, then diazotization in the presence of sulfur dioxide and cuprous chloride as shown above.

The o-alkoxymethyl- or o-thioalkoxymethylnitrobenzenes are in turn prepared via "Williamson Synthesis", according to Equations 7a or 7b.

Equation 7a

Equation 7b

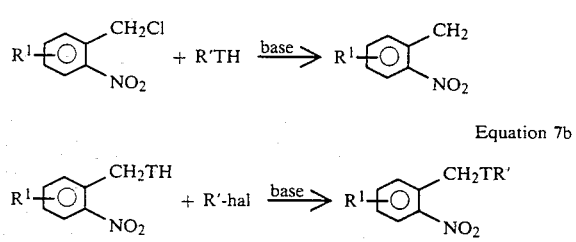

T=O or S;
R'=$C_1$-$C_4$ alkyl or $C_3$-$C_4$ alkenyl.

"Williamson Synthesis" has been widely used for the preparation of ethers as reviewed by W. Theilheimer, *Syn. Methods of Org. Chem.*, Vol. VII, p. 112.

Alternatively, o-alkoxymethyl or o-thioalkoxymethylbenzenesulfonyl chlorides, XIV, can be obtained from an appropriately substituted α-hydroxy-o-toluenesulfonic acid-α-sultone, XI, via ring-opening reaction with an alkoxide or thioalkoxide anion as depicted in Equations 7c and 7d.

Equation 7c

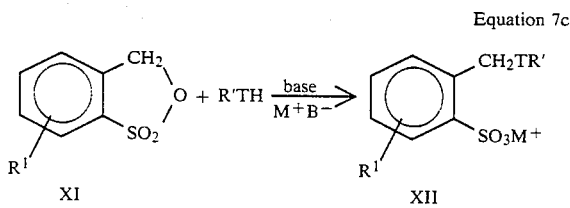

Equation 7d

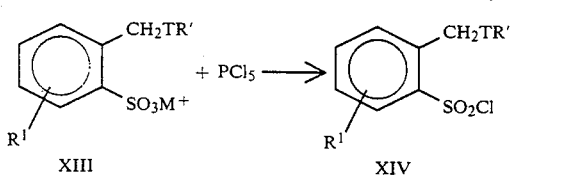

Reaction 7c is closely related to the alkylation of acyloxides and acetamide with sultones as disclosed by J. H. Helberger et al., *Ann.*, 565, 22 (1949). Conversion of the sulfonic acid salt to the sulfonyl chloride is then carried out according to the teaching of *Org. Synthesis*, Coll. Vol. IV, 846, 693.

Benzenesulfonamides of Formula XVI can also be derived from compound XV as illustrated in Equation 7e.

Equation 7e

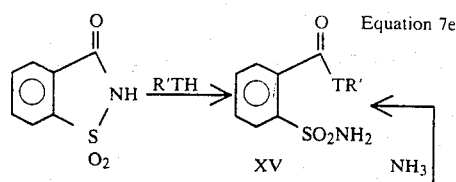

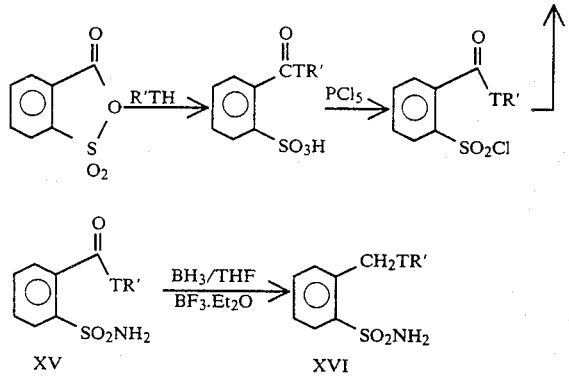

Preparation of o-sulfamylbenzoic acid esters, XV, from saccharin or sulfobenzoic acid anhydride is well known in the art, e.g., B. Loev and M. Kormendy, *J. Org. Chem.* 27, 1703 (1962). The esters, XV, can be readily reduced to the ethers XVI with diborane in a suitable organic solvent, e.g., tetrahydrofuran, in the presence of fifteen fold of boron trifluoride etherate under reflux for 18 hours, as described by R. P. Graber and M. B. Meyers, *J. Org. Chem.* 26, 4773 (1961).

When A is a substituted phenoxy group, the corresponding isocyanates of Formula II may be prepared by methods analogous to those described in U.S. Pat. No. 4,191,553.

Preparation of the sulfonylisocyanates or isothiocyanates of Formula II in which R is cycloalkenyl may be accomplished from the corresponding sulfonyl chlorides by the methods described above. These sulfonyl chlorides may be prepared starting from the sulfonic acid salt XVII as shown in Equation 8, wherein p=1 or 2, and $R^1$ is as defined above.

Equation 8

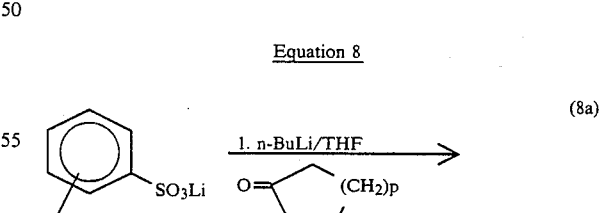

(8a)

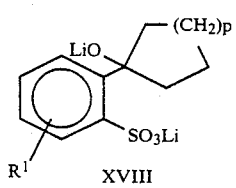

-continued
Equation 8

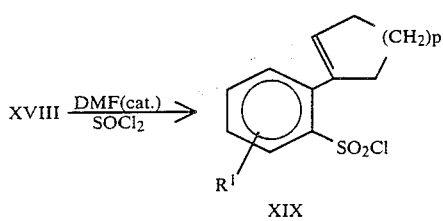   (8b)

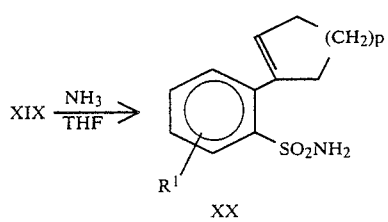   (8c)

In Reaction (8a) a substituted benzenesulfonic acid salt is contacted with a slight excess of an alkyllithium reagent such as n-butyllithium at 0° to 50° C., preferably below ambient temperature, and in an inert aprotic solvent such as tetrahydrofuran (THF). After allowing this mixture to stir at ambient temperature for approximately one hour, it is cooled in an ice bath and contacted slowly with a slight excess of the appropriate ketone then allowed to stir at ambient temperature overnight. The dilithium salt (XVIII) normally precipitates from the mixture and is collected by filtration and dried.

The product obtained from reaction (8a), may then be converted to the alkenylsulfonyl chloride XIX by reacting XVIII with a 10 to 20 fold excess of thionyl chloride containing a catalytic amount of N,N-dimethylformamide (1% is conveniently used) at 0° to 10° C., preferably. After 1 hour the reaction is normally complete and is then warmed to room temperature, filtered to remove inorganic by-products and the filtrate is evaporated under reduced pressure.

Conversion of the crude product XIX into the desired sulfonamide XX can be accomplished using the standard procedures mentioned above, for example, by dissolving XIX in THF and adding an excess of concentrated aqueous ammonia.

This procedure outlined in Equation 8 may also be used to prepare acyclic 2-alkenylarylsulfonamides from acyclic ketones and the appropriate benzenesulfonic acid salt (XVIII).

An additional synthesis of sulfonamides XXVI which may also be used as precursors to isocyanates of Formula II is presented in Equation 9, wherein R' is hydrogen or methyl, and M is an alkali metal.

Equation 9

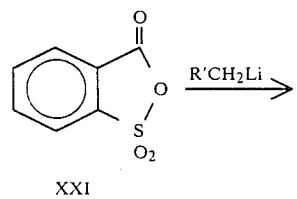   (9a)

-continued
Equation 9

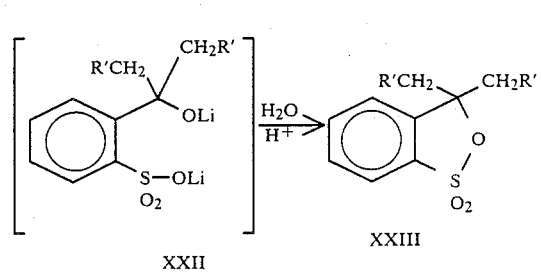

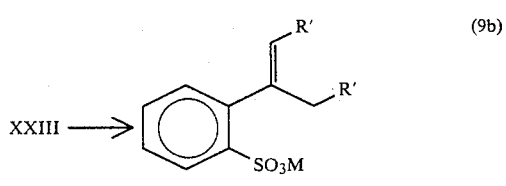   (9b)

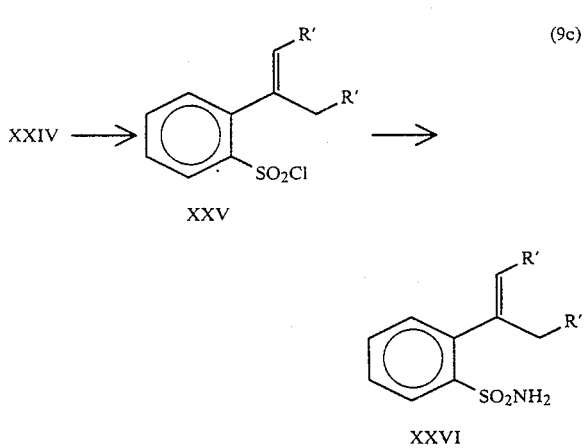   (9c)

Commercially available sulfobenzoic anhydride (XXI) may be contacted with methyl- (or ethyl)lithium in an anhydrous aprotic solvent such as diethyl ether or THF to yield the water soluble dilithium salt XXII. This salt is not isolated but warmed in aqueous mineral acid solution such as hydrochloric acid to form the water insoluble sultone XXIII. The product XXIII is conveniently isolated by extraction with an organic solvent such as methylene chloride or chloroform and evaporation to dryness. The sultone product thus obtained (XXIII) can be ring opened to the sulfonic acid salt XXIV upon treatment with an equivalent amount of a strong alkali metal alkoxide base such as potassium tert-butoxide in tert-butanol solution at temperatures from 20° to 100° C., preferably at the boiling point of the solvent. The salt XXIV conveniently precipitates as it is formed and can be isolated by filtration.

Conversion of the sulfonic acid salt XXIV to the sulfonyl chloride XXV proceeds in the same manner as that described above for the preparation of XIX. Similarly, standard amination procedures yield the sulfonamide XXVI.

The intermediates of Formula II in which R is $CH_2L$ or $CH(CH_3)L$, and L is $SO_2N(CH_3)_2$ or $CO_2R^{17}$ may be prepared from the corresponding sulfonamides by the procedures outlined above. These sulfonamide starting materials may be synthesized by methods known in the art, for example, by procedures directly analogous to that outlined above in Equations 5a through 5d.

B. Furo [2,3-d]pyrimidine Intermediates

The pyrimidine intermediates III in which Z is hydrogen or methyl, X and Y are both methyl have been reported in the literature by E. Bisagni et al., [*Bul. Soc. Chim. Fr.*, 803 (1969)]. An apparently more efficient procedure is depicted in Equation 10 for the case in which Z is hydrogen, Y' is methyl or hydrogen, and Y is ethyl or methyl.

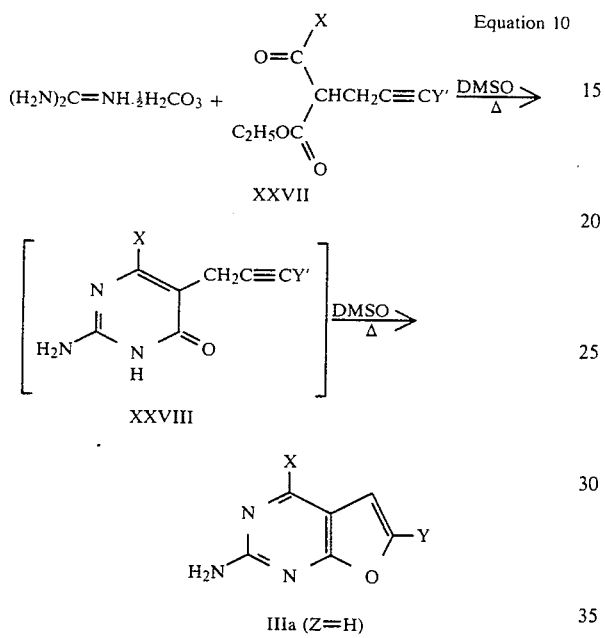

$X = CH_3$ or $C_2H_5$, $Y = CH_3$ or $C_2H_5$.

The keto-ester precursors XXVII are prepared by well known literature methods, e.g, J. F. Tinker and T. E. Whatmough, *J. Amer. Chem. Soc.* 74 5235 (1952).

Reacting XXVII with an excess of guanidine carbonate in an organic solvent, preferably a polar aprotic solvent such as dimethylsulfoxide (DMSO), dimethylformamide (DMF), or N,N-dimethylacetamide, at a temperature of 80° to 200°, preferably 100° to 160°, ambient pressure and preferably under an inert atmosphere, yields both IIIa and XXVIII as products. The products are isolated upon dilution of the reaction mixture with, for example, acetone and water successively. Higher reaction temperatures and longer reaction times (e.g., in DMSO at 130°–150° for 2 to 8 hours) favor the production of the furopyrimidine IIIa over the uncyclized pyrimidine XXVIII.

The intermediates of Formula III in which X is chloro, Y is methyl or ethyl and Z is H may be prepared from the appropriate malonic esters derivatives XXIX which are known in the art, as outlined in Equation 11, where Y' is hydrogen or methyl.

Equation 11

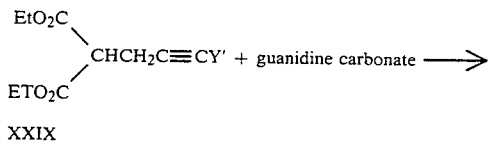

XXIX

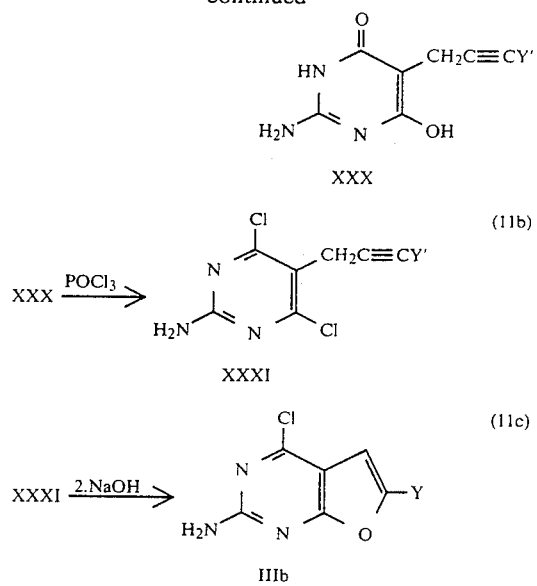

In equation 11a the diester XXIX is reacted with an excess of guanidine carbonate and heated in a suitable solvent such as ethanol or methanol at 50° to 150°, most conveniently at the boiling point of the solvent chosen. The product pyrimidine XXX is then isolated and contacted with a large excess of phosphorus oxychloride at 50° to 150°, most conveniently at the boiling point of the reaction mixture. The dichloro compound XXXI may be isolated by removal of the excess phosphorus oxychloride under reduced pressure, trituration of the solid residue in ice water and filtration of the product. Cyclization of XXXI occurs readily in a solvent medium comprised of water and a water-miscible organic solvent such as t-butanol and two equivalents of a base such as an alkali metal hydroxide with heat applied in the range of 50° to 125°. The product is conveniently isolated upon removal of the organic solvent under reduced pressure and filtration of the water-insoluble pyrimidine IIIb.

The chloro compound IIIb may also be used as an intermediate to additional heterocyclic amines of Formula III. Displacement of the chlorine of IIIb by various reagents such as sodium methoxide, potassium thiomethoxide, dimethylamine or similar nucleophilic species readily affords the corresponding substituted furo[2,3-d]pyrimidines and is depicted in Equation 12.

Equation 12

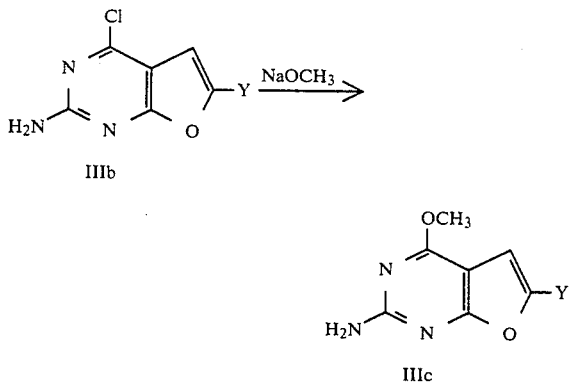

19
-continued

IIIb $\xrightarrow{KSCH_3}$ 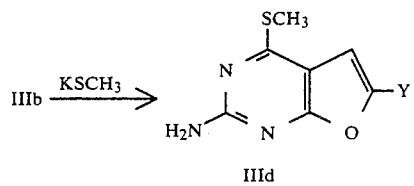

IIId

IIIb $\xrightarrow{(CH_3)_2NH}$ 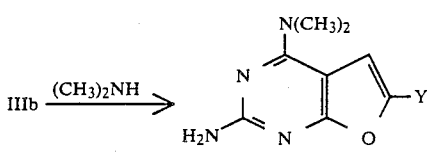

IIIe

IIb $\xrightarrow{[H]}$ 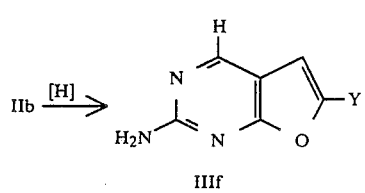

IIIf

Compounds of Formula III in which X is hydrogen (IIIf) may be prepared by reduction of the chloro compound IIIb with reducing agents such as zinc in acetic acid.

The compounds of Formula III in which Y is hydrogen and X is methyl or ethyl may be prepared by reduction of the corresponding lactone as depicted in Equation 13. The condensation of dimethyl acetylsuccinate or methyl 4-oxo-3-carbomethoxyhexanoate and guanidine carbonate at elevated temperatures produces the lactone XXXII. Treatment of XXXII with a reducing agent such as aqueous sodium amalgam in a dilute acid reaction medium at ambient temperature followed by heating in more concentrated aqueous mineral acid affords the unsubstituted furo[2,3-d]pyrimidin-2-amine IIIe. The latter may be isolated by neutralization of the aqueous mixture and filtration or extraction of the product with an organic solvent and evaporation to dryness.

Equation 13

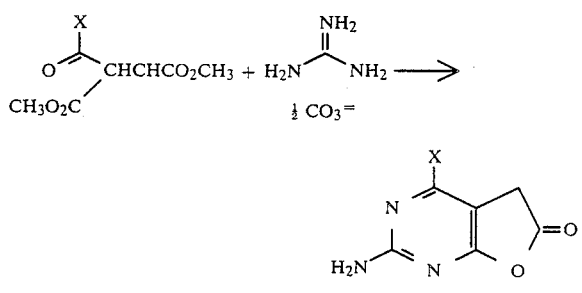

XXXII

XXXII $\xrightarrow[\text{2. H}^+]{\text{1. [H]}}$ 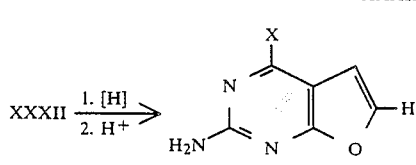

IIIe

20

C. Special Preparations

Several of the compounds of this invention of Formula I may also be used as starting materials for preparing compounds of Formula I which are agriculturally useful.

Compounds of Formula I in which R or $R^3$ is $COR^4$, wherein $R^4$ is an alkylthio or a secondary alkoxy moiety may be prepared from the corresponding methyl esters ($R^4 = CH_3O$) as shown in Equation 14a.

Equation 14a

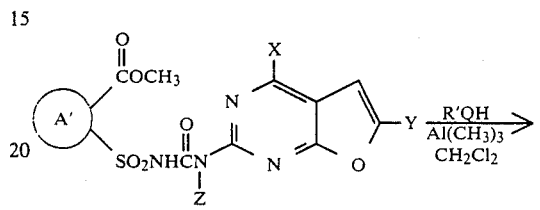

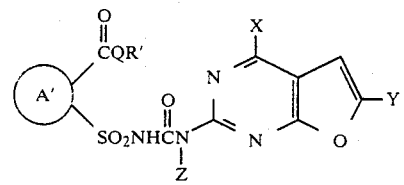

Similarly, the amides of Formula I (wherein R is $COR^4$ and $R^4$ is $NR^{11}R^{12}$) may be synthesized using the appropriate dialkylaluminum amide (from an amine and trimethylaluminum) as illustrated in Equation 14b. The procedures outlined in Equation 14b

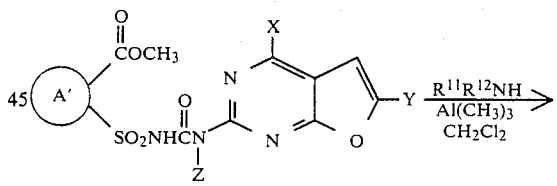

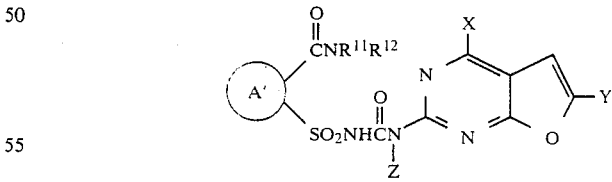

Equations 14a and 14b are described in unexamined European Pat. No. 7687, published Feb. 6, 1980.

Certain compounds of Formula I are prepared by the reaction of an excess of organolithium compound with a carboxylic acid derivative as described in Equation 15.

Equation 15

-continued

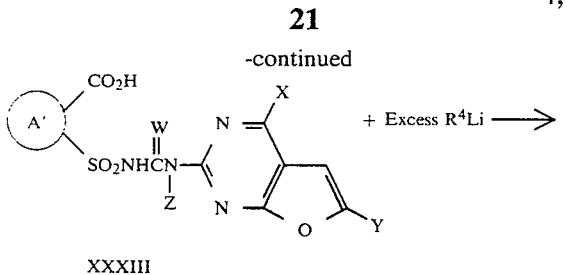

XXXIII

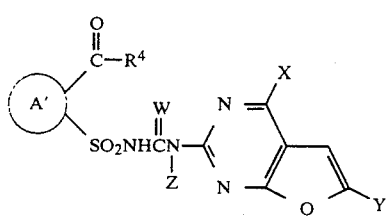

XXXIV where

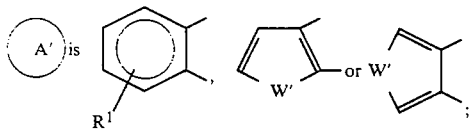

$R^4$ is $C_1-C_3$ alkyl; and
W', $R^1$, W, Z, X, and Y are as previously described.
An excess of organolithium compound in a suitable solvent such as diethyl ether, hexane, pentane, or benzene is added to a solution or slurry of XXXIII in a similar solvent at temperatures between −100° and 0° C. The mixture is allowed to warm to room temperature and stir for 30 minutes. Aqueous acid is then added and the compound XXXIV is extracted into a suitable solvent to free it from salts followed by evaporation of the solvent. Purification is done by chromatography on silica gel.

The synthesis of a wide variety of organolithium compounds by many different procedures is known in the art. A summary of methods with bibliography is contained in *Organo-Metallic Compounds*, G. E. Coates, John Wiley and Sons, 1960, p. 3–21.

The preparation of compound XXXIII is accomplished by dissolving the compound in an aqueous methanol or ethanol solution containing KOH. The mixture is stirred at 0°–25° for 6–24 hours. The reaction yields the soluble alkali metal salt of the carboxylic acid. The salt is converted to the acid form by addition of strong mineral acids causing the carboxylic acid to precipitate. The reaction is shown in Equation 16.

Equation 16

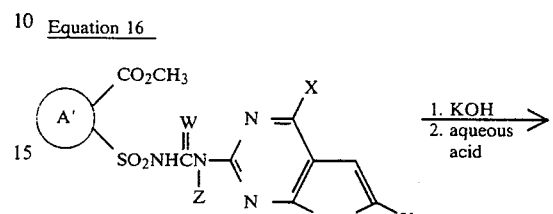

XXXIV

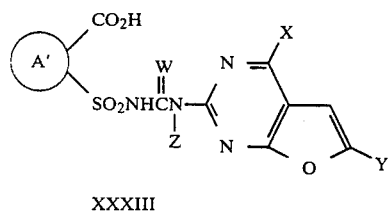

XXXIII

Aldehydes of Formula I ($R^4$=H) wherein $R^1$ does not equal $NO_2$ are prepared by the procedure of Equation 17.

Equation 17

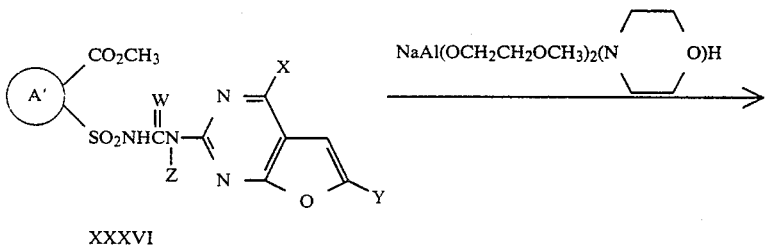

XXXVI

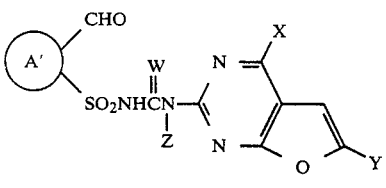

XXXVII

Following the procedure of R. Kanazawa and T. Tokoroyama, *Synthesis*, 526 (1976), a solution of sodium bis-(2-methoxyethoxy)aluminum hydride in THF is reacted with one equivalent of morpholine. To this solution at −40° C. is added a methyl ester of Formula XXXVI and the solution is allowed to warm to 25° C. The product is isolated by addition of aqueous acid and extraction into ether or methylene chloride. Evaporation of the solvent and crystallization or column chromatography on silica gel affords the pure aldehyde, XXXVII.

The aldehydes may also be prepared from the esters by treatment with diisobutylaluminum hydride according to the procedures of E. Winterfeldt, *Synthesis,* 617 (1975).

Aldehydes of Formula I ($R^4=H$) where $R^1=NO_2$ can be prepared by the procedure outlined in Equation 18.

Equation 18

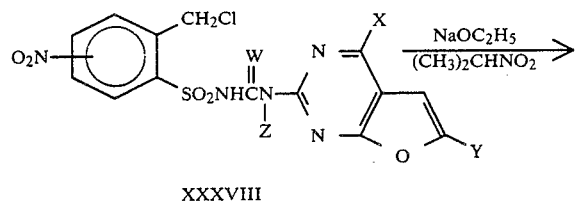

XXXVIII

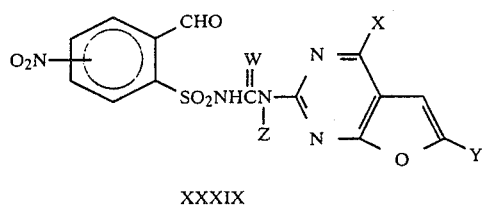

XXXIX

Following the teachings of N. Kornblum, *Angew. Chem. Int. Ed.,* 14, 734 (1975), the chloromethyl compound XXXVIII is contacted with the sodium salt of 2-nitropropane in ethanol at reflux for 4 hours. The solvent is removed under reduced pressure and the crude product is dissolved in water. Acidification causes the crude aldehyde XXXIX to precipitate. The product is purified by chromatography or recrystallization.

Certain compounds of Formula I can be prepared by reaction of salts of the carboxylic acid derivative with $R^{4'}$-halogen as shown in Equation 19.

Equation 19

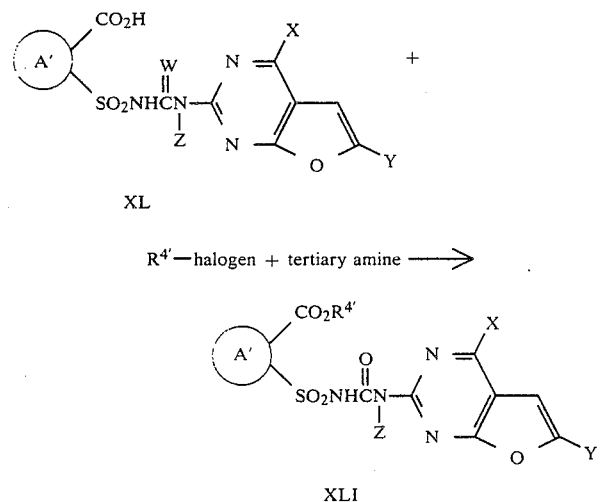

The reaction of Equation 19 is of use where the intermediate compound $R^{4'}$-halogen contains a readily replaceable halogen as is the case for substituted or unsubstituted allylic, propargillic halides, α-halonitriles, or halomethylethers.

The procedure of Equation 19 is best carried out in inert polar solvents such as THF, acetonitrile or acetone by combining the appropriately substituted carboxylic acid and base such as triethylamine, 1,4-diaza[2,2,2]bicyclooctane or diisopropylethylamine, adding the appropriate halide and heating the mixture to reflux with stirring for 1 to 16 hours. The reaction mixture can be evaporated to dryness and the residue triturated with water, filtered and washed with water to separate the desired product from the water insoluble salt.

The procedure of Equation 19 can also be used for the synthesis of compounds wherein $R^{4'}$-halogen of Equation 19 is of a less reactive species than described above. In these cases, the silver salt of the carboxylic acid is used rather than the amine salt. The silver salt which is precipitated by adding silver nitrate to an aqueous solution of the sodium salt of the acid of Formula XL is combined with the appropriate $R^{4'}$-halide using the same solvents and conditions as shown above for the amine salt.

Compounds of Formula I where R is $NH_2$ are prepared from the corresponding nitro compounds as shown in Equation 20.

Equation 20

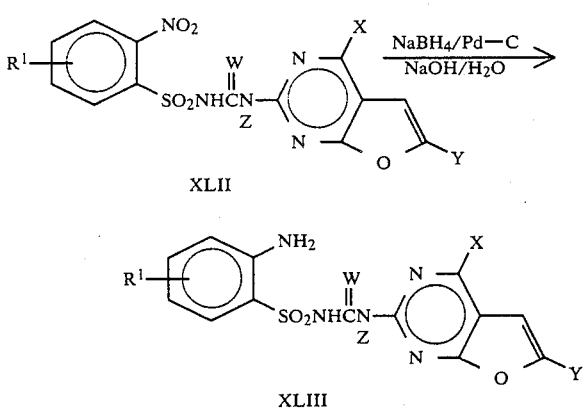

The reaction of compounds of Formula XLII is carried out in an aqueous solution containing one equivalent of NaOH and a catalytic amount of palladium on carbon by slow addition of $NaBH_4$ at ambient temperature. Reaction time is 4 to 24 hours. The product is isolated by filtration to remove catalyst followed by acidification of the precipitated solid. Recrystallization affords pure amino compounds of Formula XLIII.

Compounds of Formula I where R is cyano are prepared from the corresponding amino compounds as shown in Equation 21.

Equation 21

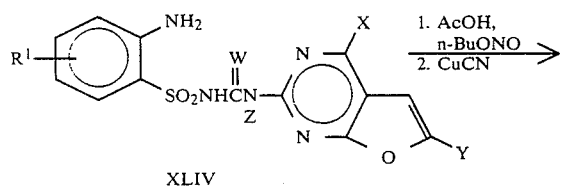

XLIV

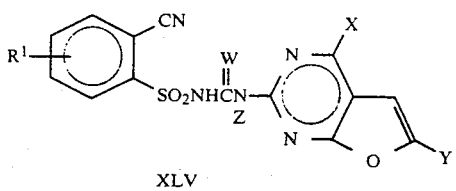

XLV

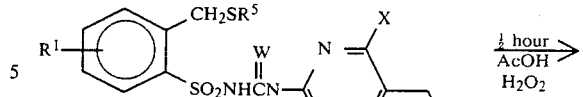

XLVII

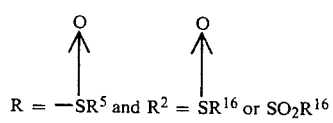

XLVIII

AcOH | H$_2$O$_2$
72 hours

↓

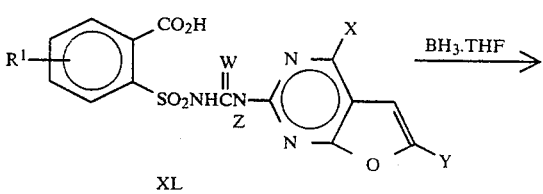

XLIX

Compounds of Formula XLIV are diazotized in acetic acid solution with an alkyl nitrite such as n-butyl nitrite at ambient temperature for 2 to 6 hours. In some instances, the addition of a small amount of water accelerates the diazotization. Excess nitrite is destroyed by the addition of sulfamic acid.

The addition of excess KCu(CN)$_2$ results in gas evolution and the mixture is stirred at ambient temperature for 1 to 4 hours. Addition of water followed by extraction with methylene chloride separates the product from salts. Evaporation of solvent yield the cyano compound of Formula XLV which can be purified by recrystallization or chromatography.

The preparation of compounds of Formula I where R=CH$_2$OH can be accomplished as shown in Equation 22.

Equation 22

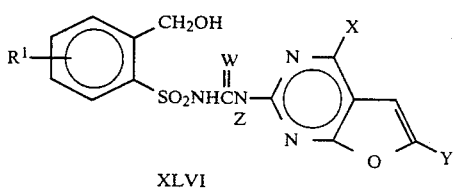

XL

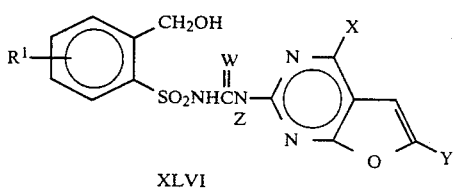

XLVI

The carboxylic acid, may be converted to the alcohol by reduction with 4-5 equivalents of borane-THF reagent in THF at ambient pressure and temperature for 4 to 18 hours. Isolation is achieved by drowning in dilute acid followed by extraction of the product with a solvent such as methylene chloride, ethyl acetate or ethyl ether. Evaporation of solvent and crystallization or column chromatography on silica gel affords the pure alcohol XLVI.

The preparation of compounds of Formula I where R=CH$_2$S(O)$_m$R$^5$ and m=1, 2 can be accomplished as shown in Equation 23.

Equation 23

The o-alkylsulfenyl- and o-alkylsulfonylmethylbenzenesulfonylureas are made from their corresponding o-thioalkoxymethylbenzenesulfonylureas XLVII by means of peroxide oxidation. Reaction of the sulfidesulfonylurea XLVII with aqueous hydrogen peroxide in acetic acid at room temperature for half an hour affords exclusively the sulfoxidesulfonylurea XLVIII. If the sulfide or sulfoxide is allowed to react for 72 hours under the same conditions, the sulfone XLIX is obtained. Oxidation for 20 hours often results in a mixture of both sulfoxide and sulfone, which can be readily separated by column chromatography and eluted with ethyl acetate. Sulfonylureas described above are generally stable under these reaction conditions. They will however, split into heterocyclic amine and o-alkylsulfonylbenzenesulfonamide if heated. A general procedure for peroxide oxidation of sulfides to sulfones can be found in the paper by A. M. Van Arendonk and E. C. Kliderer, J. Am. Chem. Soc., 62, 3521 (1940).

Compounds of Formula I where $$R = -SR^5 \text{ and } R^2 = SR^{16} \text{ or } SO_2R^{16}$$

are prepared in a similar manner apparent to one skilled in the art.

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

2-Amino-6-methyl-5-(2-propynyl)-4(3H)pyrimidinone

A mixture of 4.0 g 3-carbethoxy-5-hexyn-2-one and 2.4 g guanidine carbonate was heated in 6 ml dimethylsulfoxide under a nitrogen atmosphere at 110°–120° for 2 hours. The solution was then cooled, acetone added and the solid collected then rinsed with water to afford 0.27 g of 4,6-dimethylfuro[2,3-d]pyrimidin-2-amine: m.p. 263°–265°. The above filtrates were diluted further with water and the deposited solid was collected and dried to give 0.44 g of 2-amino-6-methyl-5-(2-propynyl)-4(3H)pyrimidinone, m.p. 245°–249°. Absorptions at 2.1 (triplet), 2.55 (singlet), and 3.45 (doublet) ppm in the nuclear magnetic resonance spectrum (60 MHz) indicated the title compound.

EXAMPLE 2

4,6-Dimethylfuro[2,3-d]pyrimidin-2-amine

A mixture of 6.0 g 3-carbethoxy-5-hexyn-2-one and 3.6 g guanidine carbonate was heated in 9 ml dimethylsulfoxide under a nitrogen atmosphere at 140° for 4 hours. The ethanol produced in the reaction was removed as it was formed by distillation. After cooling to room temperature, acetone was added then the crystalline solid was collected then rinsed with water to yield 2.6 g of 4,6-dimethylfuro[2,3-d]pyrimidine; m.p. 262°–263°. Absorptions at 2.55 (singlet), 2.82 (singlet) and 6.58 (broadened singlet) ppm in the nuclear magnetic resonance spectrum (60 MHz) indicated the title compound.

EXAMPLE 3

Methyl 2-{[(4,6-dimethylfuro[2,3-d]pyrimidin-2-yl)aminocarbonyl]aminosulfonyl}benzoate To a dry stirred solution of 0.5 g of 4,6-dimethylfuro[2,3-d]pyrimidin in 10 ml of acetonitrile at ambient temperature and pressure was added 1.6 g of 2-carbomethoxybenzenesulfonyl isocyanate. The resulting mixture was warmed on the steam bath for several minutes then stirred at ambient temperature for 4 hours. The suspended solid was collected by filtration and rinsed with acetonitrile to yield 0.87 g of methyl 2-{[(4,6-dimethylfuro[2,3-d]pyrimidin-2-yl)aminocarbonyl]aminosulfonyl}benzoate, m.p. 197°–198°. The product showed characteristic absorption bands at 1690 and 1735 cm$^{-1}$ in the infrared spectrum and at 2.45, 2.75, 3.95, 6.6, 7.7, 8.3, 10.4 and 13.0 ppm in the nuclear magnetic resonance (60 MHz) spectrum indicating the title compound.

EXAMPLE 4

2-{[(4,6-Dimethylfuro[2,3-d]pyrimidin-2-yl)aminocarbonyl]aminosulfonyl}benzoic acid, cyclopentyl ester To 30 ml of dry methylene chloride was added 7.5 ml of 2M trimethylaluminum in toluene under a nitrogen atmosphere. Subsequently, 2.0 g of cyclopentanol in 2 ml methylene chloride was added via syringe and the mixture stirred at ambient temperature for 15 minutes. After addition of 2.0 g of methyl 2-{[(4,6-dimethylfuro[2,3-d]pyrimidin-2-yl)aminocarbonyl]aminosulfonyl}benzoate to the mixture, the reaction was heated to reflux for 48 hours. The mixture was then cooled and poured into excess dilute hydrochloric acid and mixed with ethyl acetate.

The product crystallized from the two-phase mixture and was collected by filtration and rinsed well with water and ether, m.p. 202°–205°. The nuclear magnetic resonance spectrum (60 MHz) exhibited absorptions at 1.6–2.1, 5.35, 2.5 (s), 2.8 (s), 6.4, 7.6, 8.4, and 13.2 (NH) ppm indicating the title compound.

EXAMPLE 5

2-Amino-6-hydroxy-5-(2-propynyl)-4-(3H)-pyrimidinone (XXX, Y'=H)

A mixture of 5.0 g ethyl 2-carboethoxy-4-pentynoate [J. Org. Chem. 40, 851 (1975)] and 2.5 g of guanidine carbonate was heated to reflux in 50 ml of absolute ethanol for 24 hours. The suspension was then cooled to 20° and the solid product was collected. This was subsequently dissolved in 30 ml of water and acidified to pH 3 with 1N hydrochloric acid whereupon a thick precipitate formed. The mixture was warmed briefly to produce a filterable suspension which was then cooled, filtered and rinsed with water, then acetone. The yield of 2-amino-6-hydroxy-5-(2-propynyl)-4(3H)-pyrimidinone was 1.3 g (32%) as a slightly pink powder, m.p. 292°–293° dec. An NMR spectrum (60 MHz) in trifluoroacetic acid solution exhibited absorptions at 2.2 (1H), and 3.6 (2H) indicating the title compound.

EXAMPLE 6

4,6-Dichloro-5-(2-propynyl)-2-pyrimidinamine (XXXI, Y'=H)

The product of example 5 (7.2 g) was heated in 300 ml of phosphorous oxychloride to the boiling point of the mixture (ca 110°) for 24 hours. Excess phosphorus oxychloride was removed by evaporation at reduced pressure and water was added. The solid material that formed was collected in several crops, then resuspended in water and neutralized to pH 5 with saturated sodium bicarbonate solution. The product was then collected in several crops for a total yield of 7.9 g, m.p. 211°–212°.

EXAMPLE 7

4-Chloro-6-methylfuro[2,3-d]pyrimidin-2-amine (IIIb, Y=CH₃)

To a mixture of 80 ml t-butanol and 60 ml water was added 6.0 g of 4,6-dichloro-5-(2-propynyl)-2-pyrimidinamine followed by 30 ml of 2N sodium hydroxide. After heating to reflux (ca 70°) for 20 hours, the mixture was cooled and the solid product was collected by filtration. The yield of product was 1.8 g, m.p. 255°–257°. An NMR (60 MHz) spectrum in trifluoroacetic acid solution exhibited absorptions at 2.8 (doublet) and 6.6 (triplet) ppm in a 3 to 1 ratio indicating the title compound.

EXAMPLE 8

4-Methoxy-6-methylfuro[2,3-d]pyrimidin-2-amine (IIIc, Y=CH₃)

To 100 ml of anhydrous methanol was added 0.9 g sodium methoxide plus 1.7 g of 4-chloro-6-methylfuro[2,3-d]pyrimidin-2-amine and the mixture was heated to boiling for 24 hours. The methanol was then removed under reduced pressure and the product was triturated with water and filtered to afford a yield of 1.5 g, m.p. 173°–175°. An NMR (60 MHz) spectrum in trifluoroacetic acid solution exhibited absorptions at 2.5, 4.4 and 6.5 ppm in a 3:3:1 ratio indicating the title compound.

EXAMPLE 9

Methyl 3-[[(4-Methoxy-6-methylfuro[2,3-d]pyrimidin-2-yl)aminocarbonyl]aminosulfonyl]-2-thiophenecarboxylate A 0.2 g sample of 4-methoxy-6-methylfuro[2,3-d]pyrimidin-2-amine of Example 8 was stirred in 10 ml of anhydrous acetonitrile while 2.0 ml of a 1M solution of 2-carbomethoxy-3-thiophenesulfonylisocyanate in acetonitrile was added at once. The mixture immediately became homogenous then the solid product crystallized out at ambient temperature and was collected after 1 hour. The yield of product was 0.3 g, m.p. 194°–196°. An NMR (60 MHz) spectrum (CDCl₃/DMSO-d₆) exhibited absorptions at 2.5, 4.2, 6.4, 7.3, 7.9, 3.9 (methyl ester), 7.5 and 12.5 (broad NH's) ppm and the infrared spectrum (nujol) exhibited bands at 3100 (NH), 1730 (ester), 1700 (urea) cm⁻¹ indicating the title compound.

EXAMPLE 10

2-(Methylsulfonyloxy)phenyl 1-[(4,6-Dimethylfuro[2,3-d]pyrimidin-2-yl)aminocarbonyl]sulfamate A 0.6 g sample of 4,6-dimethylfuro[2,3-d]pyrimidin-2-amine of Example 2 was stirred in 20 ml of acetonitrile (anhydrous) while 1.9 g of 2-(methylsulfonyloxy)-phenoxysulfonyl isocyanate was added and the homogenous mixture was stirred for several days at ambient temperature. The solvent was then removed in vacuo and the residue chromatographed on silica gel in 10% acetone in methylene chloride. The eluted fractions containing pure product were evaporated and the residue crystallized from a methylene chloride/ether/hexane mixture to afford 0.37 g of white powder, m.p. 174°–176°. An infrared spectrum (nujol) exhibited bands at 3150 (NH), 1705 (urea) cm⁻¹ and an NMR (60 MHz) spectrum (CDCl₃/DMSO-d₆) exhibited absorptions at 2.5, 2.6 (methyls), 3.4 (CH₃SO₂O), 6.5, 7.4–7.8 and 10.8 (NH) ppm indicating the title compound.

EXAMPLE 11

2-Chloro-N-[(4,6-dimethylfuro[2,3-d]pyrimidin-2-yl)aminocarbonyl]-3-pyridinesulfonamide To 10 ml of dry acetonitrile was added 0.4 g of 4,6-dimethylfuro[2,3-d]pyrimidin-2-amine of Example 2 followed by 1.7 g of 2-chloro-3-pyridinesulfonyl isocyanate. The mixture was warmed on the steam bath briefly then stirred at ambient temperature overnight and subsequently filtered to afford 0.64 g of product, m.p. 206°–207° dec. The infrared spectrum (nujol) exhibited bands at 1715 (urea), 3300 (NH) cm⁻¹, and the NMR spectrum (60 MHz) exhibited absorptions at 2.5, 2.75, 6.55, 7.6, 8.5 and 10.7 (NH) ppm in CDCl₃/DMSO-d₆ solution indicating the title compound.

By application of one or more of the procedures of Example 1 to 11 and/or the methods described above, using the appropriate reactants, the compounds of Table I to XI can be prepared.

TABLE I

| R | R¹ | W | X | Y | Z | m.p. (°C.) |
|---|---|---|---|---|---|---|
| H | H | O | CH₃ | CH₃ | H | |
| Cl | H | O | CH₃ | CH₃ | H | 200–201° |
| Cl | 6-NO₂ | O | CH₃ | CH₃ | H | 205–206° |
| NH₂ | 5-F | O | CH₃ | CH₃ | H | |
| CN | H | O | CH₃ | CH₃ | CH₃ | |
| OC₂H₅ | 5-NO₂ | O | C₂H₅ | CH₃ | H | |
| CF₃ | H | S | CH₃ | CH₃ | H | |
| CH₃ | H | O | CH₃ | CH₃ | H | 203–206° |
| CH(CH₃)C₂H₅ | H | O | CH₃ | CH₃ | CH₃ | |
| OCH₃ | H | S | C₂H₅ | CH₃ | H | |
| O(CH₂)₃CH₃ | H | O | OC₂H₅ | CH₃ | H | |
| OCH(CH₃)₂ | 6-Cl | O | CH₃ | CH₃ | H | |
| C₂H₅ | 3-CH₃ | O | CH₃ | CH₃ | H | |
| Br | H | O | CH₃ | CH₃ | CH₃ | |
| NO₂ | H | O | CH₃ | CH₃ | H | 204–205° |
| SCH₃ | 5-CH(CH₃)₂ | S | CH₃ | CH₃ | H | |
| SC(CH₃)₃ | H | S | OCH₃ | CH₃ | H | |
| S(O)CH₃ | H | O | C₂H₅ | CH₃ | H | |

4,487,626

TABLE I-continued

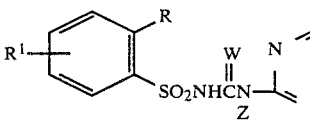

| R1 | R | W | X | Y | Z | mp |
|---|---|---|---|---|---|---|
| S(O)CH(CH3)C2H5 | 3-F | O | CH3 | C2H5 | H | |
| SO2CH3 | 5-C2H5 | O | CH3 | CH3 | H | |
| SO2CH(CH3)2 | 5-Br | O | CH3 | CH3 | H | |
| SO2(CH2)3CH3 | 6-F | O | CH3 | CH3 | CH3 | |
| SO2CH3 | H | O | CH3 | CH3 | H | 208–210° |
| SO2C2H5 | H | O | OCH3 | CH3 | H | |
| SO2OCH2CF3 | H | O | CH3 | CH3 | H | |
| SO2OCH2CCl3 | H | O | CH3 | CH3 | H | |
| SO2N(OCH3)CH3 | H | O | CH3 | CH3 | H | |
| CH3 | H | O | OCH3 | CH3 | H | |
| Cl | H | O | OCH3 | CH3 | H | 215–217° |
| NO2 | H | O | OCH3 | CH3 | H | 210–213° |
| SO2CH3 | H | O | OCH3 | CH3 | H | |
| CH3 | H | O | N(CH3)2 | CH3 | H | |
| NO2 | H | O | SCH3 | CH3 | H | |
| OCHF2 | H | O | CH3 | CH3 | H | |
| SCF3 | 5-NO2 | O | CH3 | CH3 | H | |
| S(O)CH2CF3 | H | O | OCH3 | CH3 | H | |
| SO2CF2CHF2 | 5-CH2CH(CH3)2 | O | CH3 | CH3 | H | |
| OCF2CHFCl | 3-OCH3 | S | CH3 | CH3 | H | |
| SCF2CHFBr | H | O | CH3 | CH3 | H | |
| OCF2CHFCF3 | H | O | CH3 | CH3 | H | |
| OSO2CF3 | 3-OC(CH3)3 | O | CH3 | CH3 | H | |
| OSO2CH2CH3 | H | S | CH3 | CH3 | H | |
| OSO2CHCl2 | H | O | CH3 | H | H | |
| OSO2(CH2)3Br | 3-OC2H5 | S | CH3 | CH3 | H | |
| OSO2CH(CH3)CHFCH3 | H | O | OCH3 | CH3 | H | |
| OSO2CCl3 | 4-OCH(CH3)2 | O | CH3 | CH3 | H | |
| OSO2(CH2)3CHCl2 | H | S | CH3 | CH3 | H | |
| OSO2CH(CH3)2 | H | O | CH3 | H | H | |
| CH2Cl | 3-Br | O | CH3 | CH3 | H | |
| CH2Br | H | O | CH3 | CH3 | H | |
| CH2OCH3 | H | S | C2H5 | CH3 | H | |
| CH2OCH(CH3)C2H5 | H | O | CH3 | CH3 | H | |
| CH2OCHCH=CH2 | 6-Cl | O | CH3 | CH3 | H | |
| CH2OC(CH3)CH=CH2 | H | O | OCH3 | CH3 | H | |
| CH2SCH2CH3 | H | S | CH3 | CH3 | H | |
| CH2S(O)C2H5 | H | O | CH3 | CH3 | H | |
| CH2SO2(CH2)3CH3 | H | O | CH3 | CH3 | H | |
| CH2S(O)CH3 | H | O | CH3 | C2H5 | H | |
| CH2SO2CH(CH3)2 | H | O | CH3 | CH3 | H | |
| SO2N(CH3)2 | H | O | CH3 | CH3 | H | 199–202° |
| SO2N(CH(CH3)C2H5)CH3 | 3-CF3 | S | CH3 | CH3 | H | |
| SO2N(CH(CH3)2)CH3 | 5-NO2 | S | C2H5 | CH3 | H | |
| SO2N(CH3)C2H5 | H | O | C2H5 | CH3 | CH3 | |
| SO2N(n-C4H9)2 | 3-Cl | O | CH3 | CH3 | H | |
| SO2N(C2H5)2 | 4-Br | O | CH3 | CH3 | H | |
| CH2OH | H | O | CH3 | CH3 | H | |
| NO2 | H | O | Cl | CH3 | H | |
| Cl | H | O | Cl | CH3 | H | 192–194° |
| SO2N(CH3)2 | H | O | CH3 | CH3 | H | |
| SO2N(CH3)2 | H | O | N(CH3)2 | CH3 | H | 197–199° |
| SO2N(CH3)2 | H | O | SCH3 | CH3 | H | 219–221° |
| SO2CH3 | H | O | CH3 | CH3 | H | |
| NO2 | H | O | CH3 | CH3 | H | |
| NO2 | H | O | CH3 | CH3 | CH3 | |
| CH3 | H | O | CH3 | CH3 | H | |
| SCH3 | H | O | CH3 | C2H5 | H | |
| OCH3 | 5-Cl | O | CH3 | CH3 | H | |
| OSO2CH3 | H | O | C2H5 | CH3 | H | |
| CH2SO2N(CH3)2 | H | O | CH3 | CH3 | H | |
| CH(CH3)SO2N(CH3)2 | H | O | CH3 | CH3 | H | |
| CH(CH3)Cl | H | O | CH3 | CH3 | H | |
| CH(CH3)SO2CH3 | H | O | CH3 | CH3 | H | |
| CH(CH3)OCH3 | H | O | OC2H5 | CH3 | H | |
| CH(CH3)O(CH2)4H | H | O | CH3 | CH3 | H | |
| CH(CH3)SO2(CH2)3H | H | O | CH3 | CH3 | H | |
| C(CH3)=CH2 | H | S | CH3 | CH3 | H | |
| C(CH3)=CH2 | H | O | OCH3 | CH3 | H | |
| C(CH3)=CH2 | H | O | CH3 | CH3 | H | |
| C(CH3)=CH2 | H | O | CH3 | CH3 | H | |
| Cl | H | O | N(CH3)2 | C2H5 | H | 238–240° |
| Cl | H | O | SCH3 | CH3 | H | 214–216° |
| CH=CH2 | H | O | CH3 | CH3 | H | |
| CH=CH2 | H | S | CH3 | CH3 | CH3 | |

TABLE I-continued

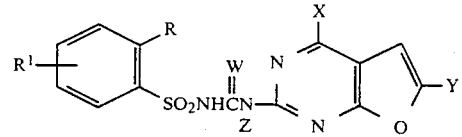

| R | R¹ | W | X | Y | Z |
|---|---|---|---|---|---|
| C(CH₃)=CHCH₃ | H | O | CH₃ | CH₃ | H |
| 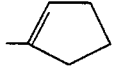 | H | O | CH₃ | CH₃ | H |
|  | H | O | OCH₃ | CH₃ | H |
| 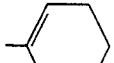 | H | O | OCH₃ | CH₃ | H |
| 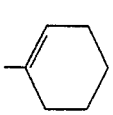 | H | O | CH₃ | H | H |
| CH₂CO₂CH₃ | H | O | CH₃ | CH₃ | H |
| CH₂CO₂CH₃ | H | O | OCH₃ | CH₃ | H |
| CH(CH₃)CO₂CH₃ | H | O | OC₂H₅ | CH₃ | H |
| CH₂CO₂CH(CH₃)₂ | H | S | CH₃ | CH₃ | H |
| CH₂CO₂(CH₂)₄H | H | O | SCH₃ | CH₃ | H |
| CH₂CO₂CH₂=CH₂ | H | O | H | CH₃ | H |
| CH₂CO₂CH₂C(CH₃)=CH₂ | H | O | CH₃ | CH₃ | H |
| CH₂CO₂(CH₂)₂OCH₃ | H | O | CH₃ | CH₃ | H |
| CH₂CO₂(CH₂)₂Cl | H | O | CH₃ | CH₃ | H |
| C₆H₅ | H | O | CH₃ | CH₃ | H |
| 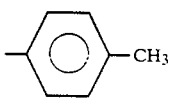 | H | O | CH₃ | CH₃ | H |
| 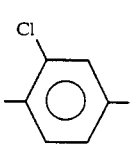 | H | O | CH₃ | CH₃ | H |
| 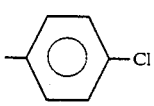 | H | O | CH₃ | CH₃ | H |

| R = COR⁴ | | | | | | |
|---|---|---|---|---|---|---|
| R⁴ | R¹ | W | X | Y | Z | m.p. (°C.) |
| H | H | O | CH₃ | CH₃ | H | |
| CH₃ | H | O | CH₃ | CH₃ | H | |
| CH₂CH₂CH₃ | 5-Cl | O | CH₃ | CH₃ | CH₃ | |
| OCH₃ | H | O | CH₃ | CH₃ | H | 197-198° |
| OCH₃ | H | O | N(CH₃)₂ | CH₃ | H | 210-212° |
| OCH₃ | 5-CF | O | CH₃ | CH₃ | H | |
| OCH₃ | H | O | OCH₃ | CH₃ | H | 216-218° |
| OCH₃ | H | O | CH₃ | Ch₃ | CH₃ | |
| OCH₃ | H | O | Cl | CH₃ | H | 194-196° |
| OCH₃ | H | S | C₂H₅ | CH₃ | H | |
| OCH₃ | 5-Cl | O | CH₃ | Ch₃ | H | |
| OCH₃ | H | O | SCH₃ | CH₃ | H | 205-207° |
| OC₂H₅ | H | O | CH₃ | CH₃ | H | 193-195° |
| O(CH₂)₅CH₃ | H | O | C₂H₅ | CH₃ | H | |
| OCH(CH₃)₂ | H | O | CH₃ | CH₃ | H | 196-197° |
| OCH(CH₃)₂ | H | O | OCH₃ | CH₃ | H | 209-212° |
| OCH(CH₃)C₂H₅ | 3-CF₃ | S | CH₃ | CH | H | |

TABLE I-continued

| | R | W/Z | X | | Y | mp |
|---|---|---|---|---|---|---|
| cyclopentyl-O- | H | O | CH₃ | CH₃ | H | 202–205° |
| cyclohexyl-O- | H | O | CH₃ | CH₃ | H | 212–214° |
| OCH₂CH=CH₂ | H | O | CH₃ | CH₃ | H | 185–186° |
| OCH(CH₃)CH=CH₂ | H | O | CH₃ | CH₃ | H | 184–186° |
| OCH₂C(CH₃)=CH₂ | H | O | C₂H₅ | CH₃ | H | |
| O(CH₂)₄CH=CH₂ | H | S | CH₃ | CH₃ | H | |
| OCH₂CN | H | O | CH₃ | CH₃ | H | |
| OCH₂C≡CH | H | O | CH₃ | CH₃ | H | |
| OCH₂C≡C(CH₂)₂CH₃ | H | O | CH₃ | CH₃ | CH₃ | |
| OCH₂C≡CCH₃ | 5-NO₂ | O | CH₃ | C₂H₅ | H | |
| OCH(CH₃)C≡CCH₃ | 6-F | O | CH₃ | CH₃ | H | |
| OCH₂CCl₃ | H | O | CH₃ | CH₃ | H | |
| OCH₂CH₂F | H | O | C₂H₅ | CH₃ | H | |
| OCH₂CH₂CH₂Br | 3-Br | O | CH₃ | CH₃ | CH₃ | |
| O(CH₂)₅CH₂Cl | H | S | CH₃ | CH₃ | H | |
| OCH₂CHFCH₂F | H | O | CH₃ | H | H | |
| OCH₂CHClCHClCH₃ | 5-OC₂H₅ | O | CH₃ | CH₃ | H | |
| OCH₂CH₂Br | H | O | C₂H₅ | CH₃ | CH₃ | |
| OCH₂CH₂OCH₃ | H | O | CH₃ | CH₃ | H | |
| (OCH₂CH₂)₂OC₂H₅ | H | S | CH₃ | CH₃ | H | |
| OCH₂CH₂CH₂OCH₃ | H | O | CH₃ | CH₃ | H | |
| OCH₂OCH₃ | H | O | CH₃ | CH₃ | H | |
| OCH₂OCH₂CH₂CH₂CH(CH₃)₂ | 3-CH₃ | O | CH₃ | CH₃ | H | |
| OCH₂OCH₂CH₂OCH₃ | H | O | CH₃ | CH₃ | H | |
| N(CH₃)₂ | H | O | CH₃ | CH₃ | H | |
| N(CH₃)C₂H₅ | 5-Cl | O | CH₃ | CH₃ | H | |
| N(C₂H₅)₂ | H | O | CH₃ | CH₃ | H | |
| NH₂ | H | O | CH₃ | CH₃ | CH₃ | |
| NH(CH₂)₃CH₃ | H | O | CH₃ | CH₃ | H | |
| N(CH₃)CH(CH₃)₂ | H | S | CH₃ | CH₃ | H | |
| pyrrolidin-1-yl | H | O | CH₃ | CH₃ | H | 193–195° |
| morpholin-4-yl | H | O | CH₃ | CH₃ | H | |
| piperidin-1-yl | H | O | CH₃ | CH₃ | H | |
| N(CH₃)OCH₃ | H | O | CH₃ | CH₃ | H | |
| NH-(2-F,4-Cl-phenyl) | H | O | CH₃ | H | H | |
| NH-(4-Cl-phenyl) | 5-Cl | O | CH₃ | CH₃ | H | |

TABLE I-continued

[Structure: R¹-substituted phenyl-SO₂NHC(W)=N-C(=N-)-furan with X, Y substituents and R on phenyl; Z on central nitrogen]

| R¹ group | R | W | X | Y | Z |
|---|---|---|---|---|---|
| N(CH₃)₂-C₆H₄-CH(CH₃)₂ | 6-F | O | CH₃ | CH₃ | H |
| NH-C₆H₄-CN | H | O | CH₃ | CH₃ | H |
| NH-C₆H₃(3-CH₃)(Cl) | H | O | CH₃ | C₂H₅ | H |
| NH-C₆H₃(Br)(CF₃) | 5-CH₃ | O | CH₃ | CH₃ | H |
| N(CH₃)CH₂-C₆H₃(OCH₃)(OCH₃) | H | O | CH₃ | CH₃ | H |
| N(CH₃)CH₂-C₆H₃(CH₃)(NO₂) | H | O | CH₃ | CH₃ | H |
| NH-C₆H₄-SCH₃ | 3-CF₃ | O | CH₃ | CH₃ | H |
| NH-C₆H₄-Br | H | O | CH₃ | CH₃ | H |
| SCH₃ | H | O | CH₃ | CH₃ | H |
| SC₂H₅ | H | S | CH₃ | CH₃ | H |
| SCH(CH₃)C₂H₅ | H | O | CH₃ | CH₃ | H |
| SCH(CH₃)₂ | 3-Br | O | CH₃ | CH₃ | H |

TABLE II

[Structure: pyridyl-SO₂NHC(W)(Z)=N-C(X)=N-furan(Y)]

| R² | W | X | Y | Z | m.p. (°C.) |
|---|---|---|---|---|---|
| H | O | CH₃ | CH₃ | H | |
| 2-Cl | O | CH₃ | CH₃ | H | 206–207° |
| 2-Cl | O | OCH₃ | CH₃ | H | |
| 4-F | S | CH₃ | CH₃ | H | |

TABLE II-continued

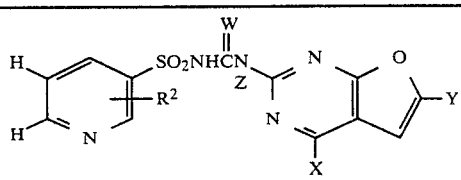

| R² | W | X | Y | Z | m.p. (°C.) |
|---|---|---|---|---|---|
| 2-Br | O | C₂H₅ | CH₃ | H | |
| 4-CH₃ | O | CH₃ | CH₃ | CH₃ | |
| 2-CH₂CH(CH₃)₂ | O | CH₃ | CH₃ | H | |
| 2-OCH₃ | S | CH₃ | CH₃ | H | |
| 4-O(CH₂)₃CH₃ | O | CH₃ | C₂H₅ | H | |
| 2-NO₂ | O | CH₃ | CH₃ | H | |
| 2-CO₂CH₃ | O | CH₃ | CH₃ | H | |
| 2-CO₂CH₃ | O | OCH₃ | CH₃ | H | |
| 4-CO₂CH₂CH₃ | S | CH₃ | CH₃ | H | |
| 2-CO₂CH(CH₃)₂ | O | C₂H₅ | CH₃ | H | |
| 2-CO₂(CH₂)₃CH₃ | S | CH₃ | CH₃ | H | |
| 2-SCH₃ | O | OCH₃ | CH₃ | H | |
| 4-SCH(CH₃)₂ | O | CH₃ | CH₃ | H | |
| 2-S(O)CH₃ | O | CH₃ | CH₃ | H | |
| 4-S(O)CH₂CH₂CH₃ | O | CH₃ | CH₃ | H | |
| 2-SO₂CH₃ | O | CH₃ | CH₃ | H | |
| 4-SO₂C₂H₅ | S | OCH₃ | CH₃ | CH₃ | |
| 2-SO₂CH(CH₃)₂ | O | CH₃ | H | H | |
| 2-CH₃ | O | CH₃ | CH₃ | H | |
| 2-OCH₃ | O | CH₃ | CH₃ | H | |
| 2-SO₂N(CH₃)₂ | O | CH₃ | CH₃ | H | |
| 2-SO₂N(C₂H₅)₂ | O | OCH₃ | CH₃ | H | |
| 4-SO₂N(CH₃)C₂H₅ | O | CH₃ | CH₃ | H | |
| 2-SO₂N(OCH₃)CH₃ | O | OCH₃ | CH₃ | H | |
| 2-Br | O | SCH₃ | CH₃ | H | |
| 4-NO₂ | O | N(CH₃)₂ | CH₃ | H | |

TABLE III

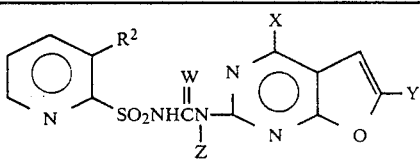

| R² | W | X | Y | Z | m.p. (°C.) |
|---|---|---|---|---|---|
| H | O | OCH₃ | CH₃ | H | |
| Cl | O | CH₃ | CH₃ | H | |
| Cl | O | OCH₃ | CH₃ | H | |
| F | O | CH₃ | CH₃ | H | |
| Br | O | OCH₃ | CH₃ | H | |
| CH₃ | S | CH₃ | C₂H₅ | H | |
| CH₂CH(CH₃)₂ | O | OCH₃ | CH₃ | CH₃ | |
| OCH₃ | O | SCH₃ | CH₃ | H | |
| O(CH₂)₃CH₃ | O | N(CH₃)₂ | CH₃ | H | |
| NO₂ | O | CH₃ | CH₃ | H | |
| CO₂CH₃ | O | CH₃ | CH₃ | H | |
| CO₂CH₃ | O | OCH₃ | CH₃ | H | |
| CO₂CH₂CH₃ | O | H | CH₃ | H | |
| CO₂(CH₂)₃CH₃ | O | OCH₃ | CH₃ | H | |
| SCH₃ | O | CH₃ | CH₃ | H | |
| SCH(CH₃)₂ | O | OC₂H₅ | CH₃ | H | |
| S(O)CH₃ | O | C₂H₅ | CH₃ | H | |
| S(O)CH₂CH₂CH₃ | O | CH₃ | CH₃ | H | |
| SO₂CH₃ | O | CH₃ | CH₃ | H | |
| SO₂C₂H₅ | S | CH₃ | CH₃ | CH₃ | |
| SO₂CH(CH₃)₂ | O | CH₃ | H | H | |
| CH₃ | O | CH₃ | CH₃ | H | |
| OCH₃ | O | CH₃ | CH₃ | H | |
| SO₂N(CH₃)₂ | O | CH₃ | CH₃ | H | |
| SO₂N(C₂H₅)₂ | O | CH₃ | CH₃ | H | |
| Br | O | OCH₃ | CH₃ | H | |
| NO₂ | O | CH₃ | CH₃ | H | |

TABLE IV

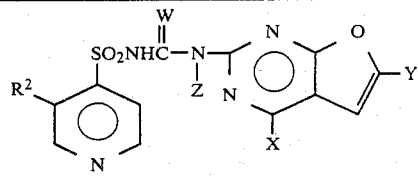

| R² | W | X | Y | Z | m.p. (°C.) |
|---|---|---|---|---|---|
| H | O | OCH₃ | CH₃ | H | |
| Cl | O | CH₃ | CH₃ | H | |
| Cl | O | OCH₃ | CH₃ | H | |
| F | O | CH₃ | CH₃ | H | |
| Br | O | OCH₃ | CH₃ | H | |
| CH₃ | S | CH₃ | C₂H₅ | H | |
| CH₂CH(CH₃)₂ | O | OCH₃ | CH₃ | CH₃ | |
| OCH₃ | O | SCH₃ | CH₃ | H | |
| O(CH₂)₃CH₃ | O | N(CH₃)₂ | CH₃ | H | |
| NO₂ | O | CH₃ | CH₃ | H | |
| CO₂CH₃ | O | CH₃ | CH₃ | H | |
| CO₂CH₃ | O | OCH₃ | CH₃ | H | |
| CO₂CH₂CH₃ | O | H | CH₃ | H | |
| CO₂(CH₂)₃CH₃ | O | OCH₃ | CH₃ | H | |
| SCH₃ | O | CH₃ | CH₃ | H | |
| SCH(CH₃)₂ | O | OC₂H₅ | CH₃ | H | |
| S(O)CH₃ | O | C₂H₅ | CH₃ | H | |
| S(O)CH₂CH₂CH₃ | O | CH₃ | CH₃ | H | |
| SO₂CH₃ | O | CH₃ | CH₃ | H | |
| SO₂C₂H₅ | S | CH₃ | CH₃ | CH₃ | |
| SO₂CH(CH₃)₂ | O | CH₃ | H | H | |
| CH₃ | O | CH₃ | CH₃ | H | |
| OCH₃ | O | CH₃ | CH₃ | H | |
| SO₂N(CH₃)₂ | O | CH₃ | CH₃ | H | |
| SO₂N(C₂H₅)₂ | O | CH₃ | CH₃ | H | |
| Br | O | OCH₃ | CH₃ | H | |
| NO₂ | O | CH₃ | CH₃ | H | |

TABLE V

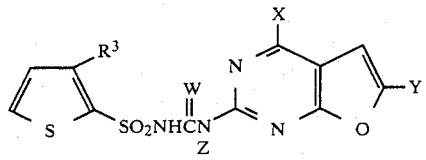

| R³ | W | X | Y | Z | m.p. (°C.) |
|---|---|---|---|---|---|
| H | O | CH₃ | CH₃ | H | |
| Cl | O | CH₃ | CH₃ | H | |
| OC₂H₅ | O | C₂H₅ | CH₃ | H | |
| CH₃ | O | CH₃ | CH₃ | H | |
| CH(CH₃)C₂H₅ | O | OCH₃ | CH₃ | H | |
| OCH₃ | S | OC₂H₅ | CH₃ | H | |
| O(CH₂)₃CH₃ | O | CH₃ | CH₃ | H | |
| OCH(CH₃)₂ | O | CH₃ | CH₃ | H | |
| C₂H₅ | O | CH₃ | CH₃ | H | |
| Br | O | CH₃ | CH₃ | H | |
| Br | O | OCH₃ | CH₃ | H | |
| NO₂ | O | CH₃ | CH₃ | H | |
| SO₂N(CH₃)₂ | O | CH₃ | CH₃ | H | |
| SO₂N(CH(CH₃)C₂H₅)CH₃ | S | CH₃ | CH₃ | H | |
| SO₂N(CH(CH₃)₂)CH₃ | S | C₂H₅ | CH₃ | H | |
| SO₂N(CH₃)C₂H₅ | O | C₂H₅ | CH₃ | CH₃ | |
| SO₂N(n-C₄H₉)₂ | O | CH₃ | CH₃ | H | |
| SO₂N(C₂H₅)₂ | O | CH₃ | H | H | |
| SO₂N(OCH₃)CH₃ | O | CH₃ | CH₃ | H | |
| COR⁴ | | | | | |
| R⁴ | | | | | |
| H | O | CH₃ | CH₃ | H | |
| CH₃ | O | CH₃ | CH₃ | H | |
| CH₂CH₂CH₃ | O | OCH₃ | CH₃ | CH₃ | |
| OCH₃ | O | CH₃ | CH₃ | H | |
| OCH₃ | O | CH₃ | CH₃ | CH₃ | |
| OCH₃ | O | C₂H₅ | CH₃ | H | |
| OCH₃ | O | OCH₃ | C₂H₅ | H | |

TABLE V-continued

| | W | X | Y | Z | m.p. (°C.) |
|---|---|---|---|---|---|
| OCH$_3$ | S | SCH$_3$ | CH$_3$ | H | |
| OCH$_3$ | O | N(CH$_3$)$_2$ | CH$_3$ | H | |
| OCH$_3$ | O | OCH$_3$ | CH$_3$ | H | |
| OCH$_3$ | S | CH$_3$ | CH$_3$ | H | |
| OCH$_3$ | S | OC$_2$H$_5$ | CH$_3$ | CH$_3$ | |
| OCH$_2$CH$_3$ | O | CH$_3$ | CH$_3$ | H | |
| O(CH$_2$)$_5$CH$_3$ | O | OCH$_3$ | CH$_3$ | H | |
| OCH(CH$_3$)$_2$ | O | CH$_3$ | CH$_3$ | H | |
| OCH(CH$_3$)C$_2$H$_5$ | O | CH$_3$ | CH$_3$ | H | |
| O-cyclopentyl | O | OCH$_3$ | CH$_3$ | H | |
| O-cyclohexyl | O | CH$_3$ | CH$_3$ | H | |
| OCH$_2$CH=CH$_2$ | O | SCH$_3$ | CH$_3$ | H | |
| OCH(CH$_3$)CH=CH$_2$ | O | CH$_3$ | CH$_3$ | H | |
| OCH$_2$C(CH$_3$)=CH$_2$ | O | CH$_3$ | C$_2$H$_5$ | H | |
| O(CH$_2$)$_4$CH=CH$_2$ | S | CH$_3$ | CH$_3$ | H | |
| OCH$_2$CN | O | CH$_3$ | CH$_3$ | H | |
| OCH$_2$C≡CH | O | CH$_3$ | CH$_3$ | H | |
| OCH$_2$C≡C(CH$_2$)$_2$CH$_3$ | O | OCH$_3$ | CH$_3$ | H | |
| OCH$_2$C≡CCH$_3$ | O | CH$_3$ | CH$_3$ | H | |
| OCH(CH$_3$)C≡CCH$_3$ | O | OCH$_3$ | CH$_3$ | H | |
| OCH$_2$CCl$_3$ | O | CH$_3$ | CH$_3$ | H | |
| OCH$_2$CH$_2$F | O | C$_2$H$_5$ | CH$_3$ | H | |
| OCH$_2$CH$_2$CH$_2$Br | O | CH$_3$ | H | CH$_3$ | |
| O(CH$_2$)$_5$CH$_2$Cl | S | CH$_3$ | CH$_3$ | H | |
| OCH$_2$CHFCH$_2$F | O | OCH$_3$ | CH$_3$ | H | |
| OCH$_2$CH$_3$ | O | N(CH$_3$)$_2$ | CH$_3$ | H | |
| OCH$_3$ | O | H | H | H | |
| OCH$_2$CHClCHClCH$_3$ | O | CH$_3$ | CH$_3$ | H | |
| OCH$_2$CH$_2$Br | O | C$_2$H$_5$ | CH$_3$ | CH$_3$ | |
| OCH$_2$CH$_2$OCH$_3$ | O | CH$_3$ | CH$_3$ | H | |
| (OCH$_2$CH$_2$)$_2$OC$_2$H$_5$ | S | OCH$_3$ | CH$_3$ | H | |
| OCH$_2$CH$_2$CH$_2$OCH$_3$ | O | CH$_3$ | CH$_3$ | H | |
| OCH$_2$OCH$_3$ | O | CH$_3$ | CH$_3$ | H | |
| OCH$_2$OCH$_2$CH(CH$_3$)$_2$ | O | CH$_3$ | CH$_3$ | H | |
| OCH$_2$OCH$_2$CH$_2$OCH$_3$ | O | OCH$_3$ | CH$_3$ | H | |
| N(CH$_3$)$_2$ | O | CH$_3$ | CH$_3$ | H | |
| N(CH$_3$)C$_2$H$_5$ | O | CH$_3$ | H | H | |
| N(C$_2$H$_5$)$_2$ | O | CH$_3$ | CH$_3$ | H | |
| NH$_2$ | O | OCH$_3$ | CH$_3$ | CH$_3$ | |
| NH(CH$_2$)$_3$CH$_3$ | O | CH$_3$ | CH$_3$ | H | |
| N(CH$_3$)CH(CH$_3$)$_2$ | S | CH$_3$ | CH$_3$ | H | |
| pyrrolidinyl | O | CH$_3$ | CH$_3$ | H | |
| morpholinyl | O | OCH$_3$ | CH$_3$ | H | |
| piperidinyl | O | CH$_3$ | CH$_3$ | H | |
| N(CH$_3$)OCH$_3$ | O | CH$_3$ | CH$_3$ | H | |
| NH-(2-F,4-Cl-C$_6$H$_3$) | O | CH$_3$ | C$_2$H$_5$ | H | |
| NH-(4-Cl-C$_6$H$_4$) | O | OCH$_3$ | CH$_3$ | H | |
| N(CH$_3$)-(4-CH(CH$_3$)$_2$-C$_6$H$_4$) | O | CH$_3$ | CH$_3$ | H | |
| NH-(4-CN-C$_6$H$_4$) | O | CH$_3$ | CH$_3$ | H | |
| NH-(3-CH$_3$,5-Cl-C$_6$H$_3$) | O | OCH$_3$ | CH$_3$ | H | |
| NH-(2-Br,4-CF$_3$-C$_6$H$_3$) | O | OCH$_3$ | CH$_3$ | H | |
| N(CH$_3$)CH$_2$-(3,4-diOCH$_3$-C$_6$H$_3$) | O | CH$_3$ | CH$_3$ | H | |
| N(CH$_3$)CH$_2$-(3-CH$_3$,4-NO$_2$-C$_6$H$_3$) | O | CH$_3$ | CH$_3$ | H | |
| NH-(4-SCH$_3$-C$_6$H$_4$) | O | OCH$_3$ | CH$_3$ | H | |
| NH-(4-Br-C$_6$H$_4$) | O | CH$_3$ | CH$_3$ | H | |
| SCH$_3$ | O | CH$_3$ | CH$_3$ | H | |
| SC$_2$H$_5$ | S | CH$_3$ | CH$_3$ | H | |
| SCH(CH$_3$)C$_2$H$_5$ | O | CH$_3$ | CH$_3$ | H | |
| SCH(CH$_3$)$_2$ | O | OCH$_3$ | CH$_3$ | H | |

TABLE VI

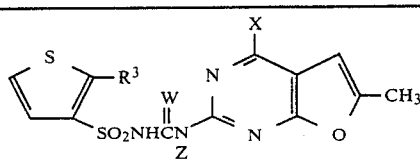

| R³ | W | X | Y | Z | m.p. (°C.) |
|---|---|---|---|---|---|
| H | O | CH₃ | CH₃ | H | |
| Cl | O | CH₃ | CH₃ | H | |
| OC₂H₅ | O | C₂H₅ | CH₃ | H | |
| CH₃ | O | CH₃ | CH₃ | H | |
| CH(CH₃)C₂H₅ | O | OCH₃ | CH₃ | H | |
| OCH₃ | S | OC₂H₅ | CH₃ | H | |
| O(CH₂)₃CH₃ | O | CH₃ | CH₃ | H | |
| OCH(CH₃)₂ | O | CH₃ | CH₃ | H | |
| C₂H₅ | O | CH₃ | CH₃ | H | |
| Br | O | CH₃ | CH₃ | H | |
| Br | O | OCH₃ | CH₃ | H | |
| NO₂ | O | CH₃ | CH₃ | H | |
| SO₂N(CH₃)₂ | O | CH₃ | CH₃ | H | |
| SO₂N(CH(CH₃)C₂H₅)CH₃ | S | CH₃ | CH₃ | H | |
| SO₂N(CH(CH₃)₂)CH₃ | S | C₂H₅ | CH₃ | H | |
| SO₂N(CH₃)C₂H₅ | O | C₂H₅ | CH₃ | CH₃ | |
| SO₂N(n-C₄H₉)₂ | O | CH₃ | CH₃ | H | |
| SO₂N(C₂H₅)₂ | O | CH₃ | H | H | |
| SO₂N(OCH₃)CH₃ | O | CH₃ | CH₃ | H | |

COR⁴

| R⁴ | W | X | Y | Z | |
|---|---|---|---|---|---|
| H | O | CH₃ | CH₃ | H | |
| CH₃ | O | CH₃ | CH₃ | H | |
| CH₂CH₂CH₃ | O | OCH₃ | CH₃ | CH₃ | |
| OCH₃ | O | CH₃ | CH₃ | H | 202–203° |
| OCH₃ | O | CH₃ | CH₃ | CH₃ | |
| OCH₃ | O | C₂H₅ | CH₃ | H | |
| OCH₃ | O | OCH₃ | C₂H₅ | H | |
| OCH₃ | S | SCH₃ | CH₃ | H | |
| OCH₃ | O | N(CH₃)₂ | CH₃ | H | |
| OCH₃ | O | OCH₃ | CH₃ | H | 209–212° |
| OCH₃ | S | CH₃ | CH₃ | H | |
| OCH₃ | S | OC₂H₅ | CH₃ | CH₃ | |
| OCH₂CH₃ | O | CH₃ | CH₃ | H | |
| O(CH₂)₅CH₃ | O | OCH₃ | CH₃ | H | |
| OCH(CH₃)₂ | O | CH₃ | CH₃ | H | |
| OCH(CH₃)C₂H₅ | O | CH₃ | CH₃ | H | |
| 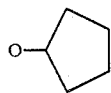 | O | OCH₃ | CH₃ | H | |
| 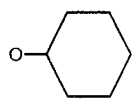 | O | CH₃ | CH₃ | H | |
| OCH₂CH=CH₂ | O | SCH₃ | CH₃ | H | |
| OCH(CH₃)CH=CH₂ | O | CH₃ | CH₃ | H | |
| OCH₂C(CH₃)=CH₂ | O | CH₃ | C₂H₅ | H | |
| O(CH₂)₄CH=CH₂ | S | CH₃ | CH₃ | H | |
| OCH₂CN | O | CH₃ | CH₃ | H | |
| OCH₂C≡CH | O | CH₃ | CH₃ | H | |
| OCH₂C≡C(CH₂)₂CH₃ | O | OCH₃ | CH₃ | H | |
| OCH₂C≡CCH₃ | O | CH₃ | CH₃ | H | |
| OCH(CH₃)C≡CCH₃ | O | OCH₃ | CH₃ | H | |
| OCH₂CCl₃ | O | CH₃ | CH₃ | H | |
| OCH₂CH₂F | O | C₂H₅ | CH₃ | H | |
| OCH₂CH₂CH₂Br | O | CH₃ | H | CH₃ | |
| O(CH₂)₅CH₂Cl | S | CH₃ | CH₃ | H | |
| OCH₂CHFCH₂F | O | OCH₃ | CH₃ | H | |
| OCH₂CH₃ | O | N(CH₃)₂ | CH₃ | H | |
| OCH₃ | O | H | H | H | |
| OCH₂CHClCHClCH₃ | O | CH₃ | CH₃ | H | |
| OCH₂CH₂Br | O | C₂H₅ | CH₃ | CH₃ | |
| OCH₂CH₂OCH₃ | O | CH₃ | CH₃ | H | |
| (OCH₂CH₂)₂OC₂H₅ | S | OCH₃ | CH₃ | H | |

TABLE VI-continued
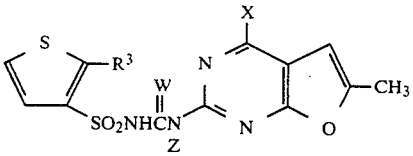
| R³ | W | X | Z | (CH₃ pos) |
|---|---|---|---|---|
| OCH₂CH₂CH₂OCH₃ | O | CH₃ | CH₃ | H |
| OCH₂OCH₃ | O | CH₃ | CH₃ | H |
| OCH₂OCH₂CH₂CH(CH₃)₂ | O | CH₃ | CH₃ | H |
| OCH₂OCH₂CH₂OCH₃ | O | OCH₃ | CH₃ | H |
| N(CH₃)₂ | O | CH₃ | CH₃ | H |
| N(CH₃)C₂H₅ | O | CH₃ | H | H |
| N(C₂H₅)₂ | O | CH₃ | CH₃ | H |
| NH₂ | O | OCH₃ | CH₃ | CH₃ |
| NH(CH₂)₃CH₃ | O | CH₃ | CH₃ | H |
| N(CH₃)CH(CH₃)₂ | S | CH₃ | CH₃ | H |
|  | O | CH₃ | CH₃ | H |
|  | O | OCH₃ | CH₃ | H |
|  | O | CH₃ | CH₃ | H |
| N(CH₃)OCH₃ | O | CH₃ | CH₃ | H |
| 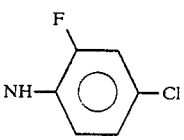 | O | CH₃ | C₂H₅ | H |
| 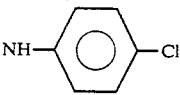 | O | OCH₃ | CH₃ | H |
| 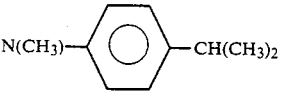 | O | CH₃ | CH₃ | H |
| 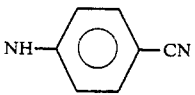 | O | CH₃ | CH₃ | H |
| 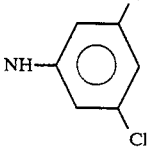 | O | OCH₃ | CH₃ | H |
| 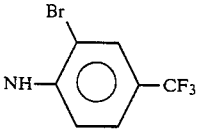 | O | OCH₃ | CH₃ | H |

TABLE VI-continued

Structure: thiophene-SO₂NHC(W)NZ-pyrimidine with X, Y, furan-CH₃, with R³ substituent

| R³ | W | X | Y | Z |
|---|---|---|---|---|
| N(CH₃)CH₂-(3,4-dimethoxyphenyl) | O | CH₃ | CH₃ | H |
| N(CH₃)CH₂-(2-methyl-4-nitrophenyl) | O | CH₃ | CH₃ | H |
| NH-(4-SCH₃-phenyl) | O | OCH₃ | CH₃ | H |
| NH-(4-Br-phenyl) | O | CH₃ | CH₃ | H |
| SCH₃ | O | CH₃ | CH₃ | H |
| SC₂H₅ | S | CH₃ | CH₃ | H |
| SCH(CH₃)C₂H₅ | O | CH₃ | CH₃ | H |
| SCH(CH₃)₂ | O | OCH₃ | CH₃ | H |

TABLE VII

| R³ | W | X | Y | Z | m.p. (°C.) |
|---|---|---|---|---|---|
| H | O | CH₃ | CH₃ | H | |
| Cl | O | CH₃ | CH₃ | H | |
| OC₂H₅ | O | C₂H₅ | CH₃ | H | |
| CH₃ | O | CH₃ | CH₃ | H | |
| CH(CH₃)C₂H₅ | O | OCH₃ | CH₃ | H | |
| OCH₃ | S | OC₂H₅ | CH₃ | H | |
| O(CH₂)₃CH₃ | O | CH₃ | CH₃ | H | |
| OCH(CH₃)₂ | O | CH₃ | CH₃ | H | |
| C₂H₅ | O | CH₃ | CH₃ | H | |
| Br | O | CH₃ | CH₃ | H | |
| Br | O | OCH₃ | CH₃ | H | |
| NO₂ | O | CH₃ | CH₃ | H | |
| SO₂N(CH₃)₂ | O | CH₃ | CH₃ | H | |
| SO₂N(CH(CH₃)C₂H₅)CH₃ | S | CH₃ | CH₃ | H | |
| SO₂N(CH(CH₃)₂)CH₃ | S | C₂H₅ | CH₃ | H | |
| SO₂N(CH₃)C₂H₅ | O | C₂H₅ | CH₃ | CH₃ | |
| SO₂N(n-C₄H₉)₂ | O | CH₃ | CH₃ | H | |
| SO₂N(C₂H₅)₂ | O | CH₃ | H | H | |
| SO₂N(OCH₃)CH₃ | O | CH₃ | CH₃ | H | |

| COR⁴ R⁴ | W | X | Y | Z | |
|---|---|---|---|---|---|
| H | O | CH₃ | CH₃ | H | |
| CH₃ | O | CH₃ | CH₃ | H | |
| CH₂CH₂CH₃ | O | OCH₃ | CH₃ | CH₃ | |
| OCH₃ | O | CH₃ | CH₃ | H | |
| OCH₃ | O | CH₃ | CH₃ | CH₃ | |
| OCH₃ | O | C₂H₅ | CH₃ | H | |

TABLE VII-continued

Structure: Thiophene-SO₂NHC(W)=NC(Z)-pyrimidine fused with furan bearing CH₃; with R³ on thiophene, X on pyrimidine.

| R³ | W | X | | |
|---|---|---|---|---|
| OCH₃ | O | OCH₃ | C₂H₅ | H |
| OCH₃ | S | SCH₃ | CH₃ | H |
| OCH₃ | O | N(CH₃)₂ | CH₃ | H |
| OCH₃ | O | OCH₃ | CH₃ | H |
| OCH₃ | S | CH₃ | CH₃ | H |
| OCH₃ | S | OC₂H₅ | CH₃ | CH₃ |
| OCH₂CH₃ | O | CH₃ | CH₃ | H |
| O(CH₂)₅CH₃ | O | OCH₃ | CH₃ | H |
| OCH(CH₃)₂ | O | CH₃ | CH₃ | H |
| OCH(CH₃)C₂H₅ | O | CH₃ | CH₃ | H |
| O-cyclopentyl | O | OCH₃ | CH₃ | H |
| O-cyclohexyl | O | CH₃ | CH₃ | H |
| OCH₂CH=CH₂ | O | SCH₃ | CH₃ | H |
| OCH(CH₃)CH=CH₂ | O | CH₃ | CH₃ | H |
| OCH₂C(CH₃)=CH₂ | O | CH₃ | C₂H₅ | H |
| O(CH₂)₄CH=CH₂ | S | CH₃ | CH₃ | H |
| OCH₂CN | O | CH₃ | CH₃ | H |
| OCH₂C≡CH | O | CH₃ | CH₃ | H |
| OCH₂C≡C(CH₂)₂CH₃ | O | OCH₃ | CH₃ | H |
| OCH₂C≡CCH₃ | O | CH₃ | CH₃ | H |
| OCH(CH₃)C≡CCH₃ | O | OCH₃ | CH₃ | H |
| OCH₂CCl₃ | O | CH₃ | CH₃ | H |
| OCH₂CH₂F | O | C₂H₅ | CH₃ | H |
| OCH₂CH₂CH₂Br | O | CH₃ | H | CH₃ |
| O(CH₂)₅CH₂Cl | S | CH₃ | CH₃ | H |
| OCH₂CHFCH₂F | O | OCH₃ | CH₃ | H |
| OCH₂CH₃ | O | N(CH₃)₂ | CH₃ | H |
| OCH₃ | O | H | H | H |
| OCH₂CHClCHClCH₃ | O | CH₃ | CH₃ | H |
| OCH₂CH₂Br | O | C₂H₅ | CH₃ | CH₃ |
| OCH₂CH₂OCH₃ | O | CH₃ | CH₃ | H |
| (OCH₂CH₂)₂OC₂H₅ | S | OCH₃ | CH₃ | H |
| OCH₂CH₂CH₂OCH₃ | O | CH₃ | CH₃ | H |
| OCH₂OCH₃ | O | CH₃ | CH₃ | H |
| OCH₂OCH₂CH₂CH(CH₃)₂ | O | CH₃ | CH₃ | H |
| OCH₂OCH₂CH₂OCH₃ | O | OCH₃ | CH₃ | H |
| N(CH₃)₂ | O | CH₃ | CH₃ | H |
| N(CH₃)C₂H₅ | O | CH₃ | H | H |
| N(C₂H₅)₂ | O | CH₃ | CH₃ | H |
| NH₂ | O | OCH₃ | CH₃ | CH₃ |
| NH(CH₂)₃CH₃ | O | CH₃ | CH₃ | H |
| N(CH₃)CH(CH₃)₂ | S | CH₃ | CH₃ | H |
| pyrrolidin-1-yl | O | CH₃ | CH₃ | H |
| morpholin-4-yl | O | OCH₃ | CH₃ | H |
| piperidin-1-yl | O | CH₃ | CH₃ | H |
| N(CH₃)OCH₃ | O | CH₃ | CH₃ | H |

TABLE VII-continued
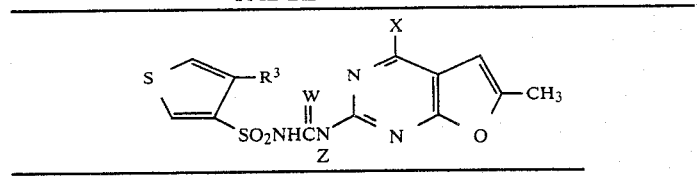
| R³ | W | X | Z | R³ position |
|---|---|---|---|---|
|  | O | CH₃ | C₂H₅ | H |
|  | O | OCH₃ | CH₃ | H |
| 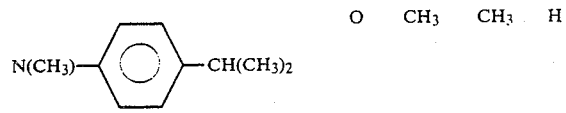 | O | CH₃ | CH₃ | H |
|  | O | CH₃ | CH₃ | H |
|  | O | OCH₃ | CH₃ | H |
|  | O | OCH₃ | CH₃ | H |
| 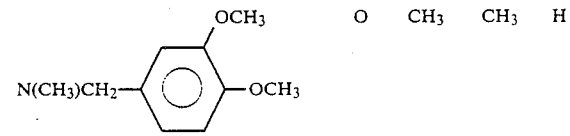 | O | CH₃ | CH₃ | H |
| 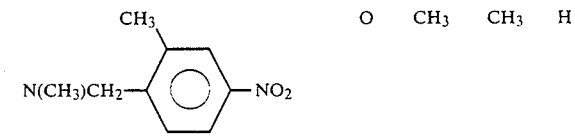 | O | CH₃ | CH₃ | H |
|  | O | OCH₃ | CH₃ | H |
|  | O | CH₃ | CH₃ | H |
| SCH₃ | O | CH₃ | CH₃ | H |
| SC₂H₅ | S | CH₃ | CH₃ | H |
| SCH(CH₃)C₂H₅ | O | CH₃ | CH₃ | H |

TABLE VII-continued

Structure: thiophene with R³, SO₂NHC(W)(Z)N=C(X)— fused furan with CH₃ and connected via N to the furan ring bearing CH₃ and O.

| R³ | W | X | Y | Z |
|---|---|---|---|---|
| SCH(CH₃)₂ | O | OCH₃ | CH₃ | H |

TABLE VIII

Structure: furan with CO₂R¹⁷ and SO₂NHC(W)(Z)N=C(X)— linked to furan with Y and O.

| R¹⁷ | W | X | Y | Z | m.p. (°C.) |
|---|---|---|---|---|---|
| CH₃ | O | C₂H₅ | CH₃ | H | |
| CH₃ | O | OCH₃ | CH₃ | H | |
| CH₃ | O | CH₃ | CH₃ | H | 179–181° |
| CH₃ | O | Cl | CH₃ | H | |
| CH₃ | O | SCH₃ | CH₃ | H | |
| CH₃ | O | N(CH₃)₂ | CH₃ | H | |
| CH₃ | S | CH₃ | CH₃ | H | |
| C₂H₅ | O | OCH₃ | CH₃ | H | |
| C₂H₅ | O | CH₃ | CH₃ | CH₃ | |
| CH(CH₃)₂ | O | H | CH₃ | H | |
| CH(CH₃)₂ | O | CH₃ | H | H | |
| CH(CH₃)C₂H₅ | O | C₂H₅ | CH₃ | H | |
| (CH₂)₃CH₃ | O | CH₃ | CH₃ | H | |
| CH₂CH(CH₃)₂ | O | OCH₃ | CH₃ | H | |
| CH₂CH=CH₂ | O | CH₃ | CH₃ | H | |
| CH₂CH=CH₂ | O | OC₂H₅ | CH₃ | H | |
| CH(CH₃)CH=CH₂ | O | CH₃ | C₂H₅ | H | |
| CH₂CH₂OCH₃ | O | Cl | CH₃ | H | |
| CH₂CH₂OCH₃ | S | CH₃ | CH₃ | H | |
| CH₂CH₂Cl | O | CH₃ | CH₃ | H | |
| CH₂CH₂Cl | O | OCH₃ | CH₃ | H | |

TABLE IX

Structure: furan with SO₂NHC(W)(Z)N=C(X)— linked to furan with Y, and CO₂R¹⁷.

| R¹⁷ | W | X | Y | Z | m.p. (°C.) |
|---|---|---|---|---|---|
| CH₃ | O | C₂H₅ | CH₃ | H | |
| CH₃ | O | OCH₃ | CH₃ | H | |
| CH₃ | O | CH₃ | CH₃ | H | 183–185° |
| CH₃ | O | Cl | CH₃ | H | |
| CH₃ | O | SCH₃ | CH₃ | H | |
| CH₃ | O | N(CH₃)₂ | CH₃ | H | |
| CH₃ | S | CH₃ | CH₃ | H | |
| C₂H₅ | O | OCH₃ | CH₃ | H | |
| C₂H₅ | O | CH₃ | CH₃ | CH₃ | |
| CH(CH₃)₂ | O | H | CH₃ | H | |
| CH(CH₃)₂ | O | CH₃ | H | H | |
| CH(CH₃)C₂H₅ | O | C₂H₅ | CH₃ | H | |
| (CH₂)₃CH₃ | O | CH₃ | CH₃ | H | |
| CH₂CH(CH₃)₂ | O | OCH₃ | CH₃ | H | |
| CH₂CH=CH₂ | O | CH₃ | CH₃ | H | |
| CH₂CH=CH₂ | O | OC₂H₅ | CH₃ | H | |
| CH(CH₃)CH=CH₂ | O | CH₃ | C₂H₅ | H | |
| CH₂CH₂OCH₃ | O | Cl | CH₃ | H | |
| CH₂CH₂OCH₃ | S | CH₃ | CH₃ | H | |
| CH₂CH₂Cl | O | CH₃ | CH₃ | H | |
| CH₂CH₂Cl | O | OCH₃ | CH₃ | H | |

TABLE X

Structure: R¹⁷O₂C-furan-SO₂NHC(W)(Z)N=C(X)—furan with Y.

| R¹⁷ | W | X | Y | Z |
|---|---|---|---|---|
| CH₃ | O | C₂H₅ | CH₃ | H |
| CH₃ | O | OCH₃ | CH₃ | H |
| CH₃ | O | CH₃ | CH₃ | H |
| CH₃ | O | Cl | CH₃ | H |
| CH₃ | O | SCH₃ | CH₃ | H |
| CH₃ | O | N(CH₃)₂ | CH₃ | H |
| CH₃ | S | CH₃ | CH₃ | H |
| C₂H₅ | O | OCH₃ | CH₃ | H |
| C₂H₅ | O | CH₃ | CH₃ | CH₃ |
| CH(CH₃)₂ | O | H | CH₃ | H |
| CH(CH₃)₂ | O | CH₃ | H | H |
| CH(CH₃)C₂H₅ | O | C₂H₅ | CH₃ | H |
| (CH₂)₃CH₃ | O | CH₃ | CH₃ | H |
| CH₂CH(CH₃)₂ | O | OCH₃ | CH₃ | H |
| CH₂CH=CH₂ | O | CH₃ | CH₃ | H |
| CH₂CH=CH₂ | O | OC₂H₅ | CH₃ | H |
| CH(CH₃)CH=CH₂ | O | CH₃ | C₂H₅ | H |
| CH₂CH₂OCH₃ | O | Cl | CH₃ | H |
| CH₂CH₂OCH₃ | S | CH₃ | CH₃ | H |
| CH₂CH₂Cl | O | CH₃ | CH₃ | H |
| CH₂CH₂Cl | O | OCH₃ | CH₃ | H |

TABLE XI

Structure: phenyl with R¹ and R²⁰, OSO₂NHC(W)(Z)N=C(X)—furan with Y.

| R¹ | R²⁰ | W | X | Y | Z | m.p. (°C.) |
|---|---|---|---|---|---|---|
| H | F | O | CH₃ | CH₃ | H | |
| H | Cl | O | CH₃ | CH₃ | H | |
| H | Cl | O | OCH₃ | CH₃ | H | |
| H | Cl | O | N(CH₃)₂ | CH₃ | H | |
| H | Br | O | H | CH₃ | H | |
| H | CO₂CH₃ | O | CH₃ | CH₃ | H | |
| H | CO₂CH₃ | O | OCH₃ | CH₃ | H | |
| H | CO₂(CH₂)₄H | O | CH₃ | CH₃ | H | |
| H | CO₂CH₂CH₂=CH₂ | S | CH₃ | CH₃ | H | |
| H | OSO₂CH₃ | O | CH₃ | CH₃ | H | 174–176° |
| H | OSO₂CH₃ | O | OCH₃ | CH₃ | H | |
| H | OSO₂(CH₂)₄H | O | CH₃ | CH₃ | H | |
| H | OSO₂(CH₂)₂OCH₃ | O | CH₃ | CH₃ | H | |
| 5-NO₂ | Cl | O | CH₃ | C₂H₅ | H | |
| 5-Cl | OSO₂CF₃ | O | CH₃ | CH₃ | H | |
| 6-Cl | NO₂ | O | CH₃ | CH₃ | H | |
| H | NO₂ | O | OCH₃ | CH₃ | CH₃ | |
| H | CH₃ | O | CH₃ | CH₃ | H | |
| H | CH₃ | O | Cl | CH₃ | H | |
| H | C₂H₅ | O | OCH₃ | CH₃ | H | |
| H | CH(CH₃)C₂H₅ | O | CH₃ | CH₃ | H | |
| H | OCH₃ | O | CH₃ | H | H | |

TABLE XI-continued

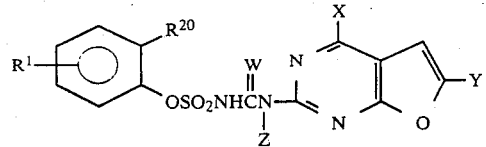

| R¹ | R²⁰ | W | X | Y | Z | m.p. (°C.) |
|---|---|---|---|---|---|---|
| H | OC₂H₅ | O | CH₃ | CH₃ | H | |
| H | O(CH₂)₄H | O | CH₃ | CH₃ | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extruded in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce form, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1977, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, Line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 12

| Wettable Powder | |
|---|---|
| 2-Chloro-N—[(4,6-dimethylfuro[2,3-d]pyrimidin-2-yl-aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 13

| Wettable Powder | |
|---|---|
| N—[(4,6-Dimethylfuro[2,3-d]pyrimidin-2-yl)aminocarbonyl]-2-nitrobenzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 14

| Granule | |
|---|---|
| Wettable Powder of Example 13 | 5% |
| attapulgite granules | 95% |

| Granule |   |
|---|---|
| (U.S.S. 20–40 mesh; 0.84–0.42 mm) |   |

A slurry of wettable powder containing ≈25% solids is sprayed on the surface of attapulgite granules in a double-cone blender. The granules are dried and packaged.

EXAMPLE 15

| Extruded Pellet |   |
|---|---|
| 2-{[(4,6-Dimethylfuro[2,3-d]pyrimidin-2-yl)aminocarbonyl]-aminosulfonyl}benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

| Oil Suspension |   |
|---|---|
| N—[(4,6-Dimethylfuro[2,3-d]pyrimidin-2-yl)aminocarbonyl]-2-methylsulfonylbenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 17

| Wettable Powder |   |
|---|---|
| 2-{[(4,6-Dimethylfuro[2,3-d]pyrimidin-2-yl)aminocarbonyl]-aminosulfonyl}benzoic acid, (2-propenyl)ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 18

| Low Strength Granule |   |
|---|---|
| N—[(4,6-Dimethylfuro[2,3-d]pyrimidin-2-yl)aminocarbonyl]-3-methyl-2-thiophenesulfonamide | 1% |
| N,N—dimethylformamide | 9% |
| attapulgite granules | 90% |

| Low Strength Granule |   |
|---|---|
| (U.S.S. 20–40 sieve) |   |

The active ingredient is dissolved in the solvent and the solution is sprayed upon dedusted granules in a double cone blender. After spraying of the solution has been completed, the blender is allowed to run for a short period and then the granules are packaged.

EXAMPLE 19

| Aqueous Suspension |   |
|---|---|
| 2-{[(4,6-Dimethylfuro[2,3-d]pyrimidin-2-yl)-aminocarbonyl]-aminosulfonyl}benzoic acid, (1-methylethyl)ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 20

| Solution |   |
|---|---|
| 2-Chloro-N—[(4,6-dimethylfuro[2,3-d]pyrimidin-2-yl)amino-carbonyl]-3-pyridinesulfonamide, sodium salt | 5% |
| water | 95% |

The salt is added directly to the water with stirring to produce the solution, which may then be packaged for use.

EXAMPLE 21

| Low Strength Granule |   |
|---|---|
| 4-{[(4,6-Dimethylfuro[2,3-d]pyrimidin-2-yl)-aminocarbonyl]-aminosulfonyl}-3-thiophenecarboxylate, methy ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 22

| Granule |   |
|---|---|
| 3-{[(4,6-Dimethylfuro[2,3-d]pyrimidin-2-yl) aminocarbonyl]-aminosulfonyl}-2-thiophenecarboxylate, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 23

| High Strength Concentrate | |
|---|---|
| 2-[[(4,6-Dimethylfuro[2,3-d]pyrimidin-2-yl)aminocarbonyl]aminosulfonyl]benzoic acid, ethyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 24

| Wettable Powder | |
|---|---|
| 2-[[(4-Methoxy-6-methylfuro[2,3-d]pyrimidin-2-yl)aminocarbonyl]aminosulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 25

| Wettable Powder | |
|---|---|
| N'—[(4,6-Dimethylfuro[2,3-d]pyrimidin-2-yl)aminocarbonyl[-N,N—dimethyl-benzene-1,2-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 26

| Oil Suspension | |
|---|---|
| N'—[(4,6-Dimethylfuro[2,3-d]pyrimidin-2-yl)aminocarbonyl]-N,N—dimethyl-benzene-1,2-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 27

| Dust | |
|---|---|
| 2-Chloro-N—[(4,6-dimethylfuro[2,3-d]pyrimidin-2-yl-aminocarbonyl]benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broadspectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application, compounds of this invention may be used to modify plant growth beneficially, and also selectively control weeds in crops such as wheat, barley, cotton and soybeans.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); $\alpha,\alpha,\alpha$-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl(methoxymethyl)acetanilide (alachlor); and 1,1-dimethyl-3-($\alpha,\alpha,\alpha$-trifluoro-m-tolyl)urea (fluometuron).

The activity of these compounds was discovered in greenhouse tests. The tests are described and the data resulting from them are shown below.

Test Procedure A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a nonphytotoxic solvent solution of the compounds of Table I. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three–five leaves were sprayed with a nonphytotoxic solvent solution of the compounds of Table I. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0 = no effect;
10 = maximum effect;
C = chlorosis or necrosis;
D = defoliation;
E = emergence inhibition;
G = growth retardation;
H = formative effects;
U = unusual pigmentation;
X = axillary stimulation; and
6Y = abscised buds or flowers.
L = lodging
6F = delayed flowering
I = increased chlorophyl

TABLE A

POST-EMERGENCE

| Compound | kg/ha | BUSH BEAN | COTTON | MORNING GLORY | COCKLEBUR | CASSIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| 2-Cl (SO2NHCNH, furan-CH3) | 0.4 | 9D,9G, 6Y | 5C,7D, 9G | 9C | 3C,9G | 6C,9G | 1C,9G | 5C,9G | 10C | 2C,9H | 2C,9G | 4C,9G | 4C,9G | 5C,9G | 1C,9G |
| 2-NO2 | 0.4 | 9C | 9C | 10C | 9C | 9C | 5C,9G | 9C | 10C | 9C | 2C,9G | 9C | 6C,9G | 9C | 9C |
| 2-CO2CH3 | 0.4 | 9C | 9C | 5C,9G | 6C,9G | 9C | 6C,9G | 6C,9G | 10C | 4C,9G | 5C,9G | 9C | 9C | 9C | 10C |
| 2-CO2CH2CH=CH2 | 0.4 | 9C | 9C | 4C,9G | 9C | 9C | 6C,9G | 1C,7G | 9C | 5C,9G | 3C,9G | 3C,9G | 2C,8G, 5X | 2C,9G | 3C,9G |
| 2-CO2CH(CH3)2 | 0.4 | 9D,9G, 6Y | 6C,8D, 9G | 9C | 9C | 6C,9G | 3C,9G | 4C,9G | 10C | 6C,9G | 2C,9G | 2C,9G | 3C,9G | 6C,9G | 1C,9G |
| 2-Cl, 3-NO2 | 0.05 | 9D,9G, 6Y | 1C,2G | 4G | 1C,8G | 2C,8G | 9C,9G | 3C,7G | 4C,8H | 2C | 1C,4G | 2U,9G | 4C,9H | 2C,7G | 2C,9H |

TABLE A-continued

| Structure | | | | | | | | | | | | |
|---|---|---|---|---|---|---|---|---|---|---|---|---|
| Structure 1 | 0.05 | 2C,6F, 6Y | 2C,1H | 2C,8G | 2C,4G | 1C | 2C,9G | 1C,5G | 6C,9H | 3C | 9C | 1H,5G 3C,9G 3U,9C |
| Structure 2 | 0.05 | 2C,7G 6Y | 1G | 1C | 1C,8G | 2C,8C | 5C,9G | 2C,6G | 9C | 3C | 9C | 10C 3C,9G 7U,9G |
| Structure 3 | 0.05 | 3C,3G, 6Y | 2C,5C, 5G | 5G | 5G | 1C,6G | 5G | 2C,7G | 9C | 2C,7G | 9G | 8U,10C 3H,9G 3U,9G 9G |
| Structure 4 | 0.05 | 9D,9G, 2U,5C, 6Y | 1C,8G | 9C | 9C | 9C | 7C,9G | 1C,5G | 9C | 3C,9G | 1C,8G | 7U,10C 3H,8G 5C,9G 2U,9G 7L |
| Structure 5 | 0.05 | 1C,3G | 2G | 1C,5G | 1C,9G | 2C,7H | 0 | 2C,9H | 10C | 2C,8G | 2C,9G | 7U,9C 5C,9G 5C,9G 3C,9H |

TABLE A-continued

| Structure | | | | | | | | | | | | | | |
|---|---|---|---|---|---|---|---|---|---|---|---|---|---|---|
| Cyclopentyl CO₂ ester, SO₂NHCONH-pyrimidine with CH₃ and methyl-furan | 0.05 | 1C,4G, 6Y | 0 | 2G | 0 | 0 | 3G | 2G | 2C | 2C,6G | 2C,7H | 2C,8G, 7X | 2C, 7G | 1C,5G |
| Cyclohexyl-S CO₂ ester, SO₂NHCONH-pyrimidine | 0.05 | 2C | 0 | 0 | 0 | 3G | 0 | 0 | 0 | 0 | 1C | 0 | 0 | 0 |
| CO₂CH(CH₃)CH=CH₂ ester, SO₂NHCONH-pyrimidine | 0.05 | 2C,7G, 6Y | 1C,5G | 2C,7G | 5H | 2C,3G | 7G,5X | 4G | 2C,9H | 1C,3G | 1C,3G | 1C,8H | 1H,7G | 1C,9G | 2C,9H |
| Pyrrolidinone carbonyl, SO₂NHCONH-pyrimidine | 0.05 | 2C,7G | 1C | 2C,6G | 2C,5G | 2C,4H | 2C,8G | 1H | 9C | 2C | 2C | 1C,8H | 2C,8G | 9G | 1C,8H |

TABLE A-continued

| Compound | Rate | | | | | | | | | | | | | | | |
|---|---|---|---|---|---|---|---|---|---|---|---|---|---|---|---|---|
| Pyrimidine-furan with Cl (pyrim) / Cl (phenyl), SO₂NHCONH linker | 0.4 | 2G | 0 | 2G | 10C | 2C | 0 | 2C | 0 | 5H | 0 | 0 | 3H | 0 | 3G | 6G,1C |
| Pyrimidine-furan with Cl / CO₂CH₃ | 0.4 | 2C | — | 2H | 2C | 2C,8G | 1C,4G | 9C | 1H | 1C,4G | 5U,9C | 1G | 3C,9G | 2U,9G | | |
| Pyrimidine-furan with OCH₃ / Cl | 0.05 | 3G | 1C,5G | 3G | 2G | 0 | 1C,4G | 1C,6H | 0 | 0 | 1C,5G | 2C,8H | 7G | 2C,7G | | |
| Pyrimidine-furan with OCH₃ / NO₂ | 0.05 | 2H | 4G | 3C | 2C | 2C | 1C | 2C | 1C | 0 | 2C | 2C | 2C | 2C | | |
| Pyrimidine-furan with OCH₃ / CO₂CH₃ | 0.05 | 3C,8G,6F | 3C,3H,9G | 2C,5G | 2C,9G | 6G | 7G | 3C,9H | 8G | 1C,8G | 2C,9H | 2C,9G | 5C,9G | 2C,9G | | |

TABLE A-continued

| Structure | | | | | | | | | | | | | | | |
|---|---|---|---|---|---|---|---|---|---|---|---|---|---|---|---|
| Structure 1 | 0.05 | 3C,9G, 6Y | 1C,5G | 6G | — | 7G | 3G | 9C | 6G | 1C | 1C,6H | 5H | 2C,8G | 3C,9H | |
| Structure 2 | 0.05 | 2G | 0 | 1C | 2C | — | 2C | 9C | 0 | 0 | 2C | 1H | 5G | 2C | |
| Structure 3 | 0.4 | 5C,9G, 4C,9G | 1C,3G | 3C,9G | 1C,5G | 5C,9G | 6C,9G | 9C | 1C | 1C,9G | 7U,9G | 5C,9G | 5C,9G | 4U,9G | |
| Structure 4 | 0.05 | 2G | 0 | 1H | 0 | 4G | 5G | 3H | 0 | 0 | 2C | 1H | 5G | 1C | |
| Structure 5 | 0.05 | 5C,9G, 6Y | 6C,9G | 9C | 6C,9G | 2C,9G | 1C,9G | 4C,9G | 1C,9G | 9G | 3C,9G | 3C,9G | 5C,9G | 9C | |

Structures (left column, top to bottom):
1. Pyridine with OCH3, CO2CH(CH3)2, SO2NHCONH—[dihydrofuran-CH3]
2. Pyridine with OCH3, SO2NHCONH—[thiophene-CO2CH3], dihydrofuran-CH3
3. Pyridine with CH3, CO2CH3, SO2NHCONH—[furan], dihydrofuran-CH3
4. Pyridine with CH3, SO2NHCONH—[furan-CO2CH3], dihydrofuran-CH3
5. Pyridine with CH3, SO2N(CH3)2, SO2NHCONH—[phenyl], dihydrofuran-CH3

TABLE A-continued
| Structure | | | | | | | | | | | | | | | | |
|---|---|---|---|---|---|---|---|---|---|---|---|---|---|---|---|---|
|  | 0.4 | 3C,6G, 6Y | 3C,6G | 1C,2H | 3C,9H | 2C,5G | 2C,9G | 1C,5G | 1C,3G | 0 | 1C | 4C,9G | 3C,9G | 2C,9G | 2C,9G |
|  | 0.05 | 4G,6Y | 0 | 0 | 0 | 0 | 0 | 0 | 0 | 0 | 0 | 2C,8H | 1H | 0 | 0 |
|  | 0.05 | 0 | 1H | 1C | 1H | 0 | 0 | 0 | 0 | 0 | 0 | 0 | 0 | 0 | 0 |
|  | 0.05 | 6F | 0 | 2G | 0 | 3G | 0 | 3G | 8H | 0 | 3G | 2C | 1C | 2G | 2C |
|  | 0.05 | 0 | 1H | 0 | 0 | 1C | 0 | 0 | 1C | 0 | 0 | 1C | 1H | 0 | 2C |
|  | 0.4 | 0 | 0 | 1H | 0 | 0 | 0 | 0 | 0 | 0 | 0 | 1C,2H | 0 | 0 | 0 |

TABLE A-continued

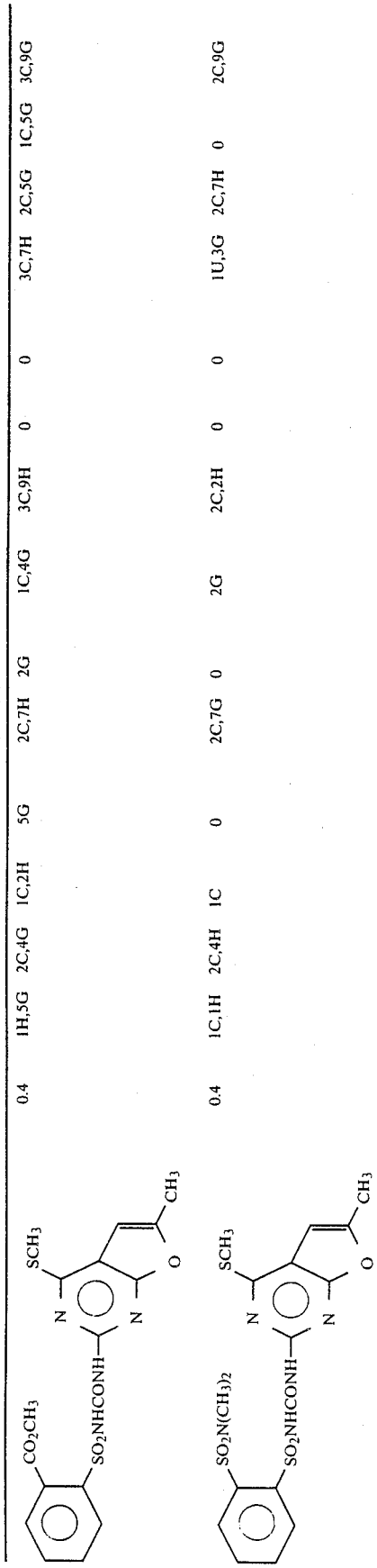

| | kg/ha | MORN-ING-GLORY | COCKLEBUR | CASSIA | NUT-SEDGE | CRAB-GRASS | BARN-YARD-GRASS | WILD OATS | WHEAT | CORN | SOYBEAN | RICE | SORGHUM |
|---|---|---|---|---|---|---|---|---|---|---|---|---|---|
| | 0.4 | 1H,5G | 2C,4G | 1C,2H | 5G | 2C,7H | 2G | 1C,4G | 3C,9H | 0 | 3C,7H | 2C,5G | 1C,5G | 3C,9G |
| | 0.4 | 1C,1H | 2C,4H | 1C | 0 | 2C,7G | 0 | 2G | 2C,2H | 0 | 1U,3G | 2C,7H | 0 | 2C,9G |

PRE-EMERGENCE

| | kg/ha | MORN-ING-GLORY | COCKLEBUR | CASSIA | NUT-SEDGE | CRAB-GRASS | BARN-YARD-GRASS | WILD OATS | WHEAT | CORN | SOYBEAN | RICE | SORGHUM |
|---|---|---|---|---|---|---|---|---|---|---|---|---|---|
| | 0.4 | 9G | 9H | 9G | 10E | 3C,9G | 6C,9H | 9H | 10E | 10E | 9H | 10E | 6C,9H |
| | 0.4 | 9C | 9H | 6C,9G | 10E | 9C | 9H,3C | 2C,9G | 2C,9G | 10H | 9H | 10E | 10H |
| | 0.4 | 9G | 9H | 2C,9G | 10E | 6C,9G | 6C,10 | 5C,9G | 5C,9G | 10H | 9H | 10E | 10E |
| | 0.4 | 8H | 9H | 4C,9G | 10E | 4C,8G | 5C,9H | 1C,9H | 1C,9H | 10E | 8H | 10E | 5C,9H |

TABLE A-continued

| Structure | | | | | | | | | | | | | |
|---|---|---|---|---|---|---|---|---|---|---|---|---|---|
| isopropyl 2-[[[[(4-methoxy-6-methyl...)]]]]benzoate-type (CO$_2$CH(CH$_3$)$_2$, SO$_2$NHCNH, CH$_3$, O furan) | 0.4 | 9G | 9H | 6C,9G | 10E | 6C,9G | 5C,9H | 2C,9G | 5C,9H | 10H | 9H | 10E | 10H |
| 2-chloro-6-nitro (Cl, NO$_2$, SO$_2$NHCNH, CH$_3$, O) | 0.05 | 8G | 9H | 2C,9G | 10E | 1C,6G | 5C,9G | 5G | 2C,9G | 10H | 9H | 2C,8G | 2C,9H |
| thiophene CO$_2$CH$_3$, CH$_3$, SO$_2$NHCONH, CH$_3$, O | 0.05 | | | 1C,4G | | | 2C,7H | 4G | 5G | | | | 10E 3C,9H |
| 2-chloropyridine CH$_3$, SO$_2$NHCONH, CH$_3$, O | 0.05 | 2C,8G | 9H | 2C,9G | 9G | 2G,1C | 9H | 2G | 8G | 4C,9G | 1G | 10E | 2C,9H |
| 2-methylphenyl SO$_2$NHCONH, CH$_3$, O | 0.05 | 5G | 9H | | | 3G | | 1C,5G | 9G | 3C,9G | 8H | 10E | |
| | 0.05 | 8G | 7C,9H | 2C,9G | | 1C,3G | 3C,9H | 2C,8G | 7G | 3C,9H | 8H | 10E | 4C,9H |

TABLE A-continued

| Structure | | | | | | | | | | | | | | | | |
|---|---|---|---|---|---|---|---|---|---|---|---|---|---|---|---|---|
| Pyrimidine with CO₂CH₂CH₃, SO₂NHCONH-phenyl | 0.05 | 9G | 2C,9H | | 9G | 10E | 5G | 2C,9H | 2C,9G | 10E | 10E | 2H,5G | 10E | 10H | | |
| Pyrimidine with SO₂CH₃, SO₂NHCONH-phenyl | 0.05 | 2C,7G | 9H | 2C,8G | 2G | 3G,1C | 9H | 2C,9G | 2C,9H | 6H | 10E | 7C,9H | | | | |
| Pyrimidine with cyclopentyl-CO₂, SO₂NHCONH-phenyl | 0.05 | 0 | 8H | 3G | 2G | 1C | 2C,5G | 0 | 3G | 3C,8G | 1C,2G | | | | | |
| Pyrimidine with thiacyclohexyl-CO₂, SO₂NHCONH-phenyl | 0.05 | 0 | 0 | 0 | 0 | 0 | 4G | 0 | 0 | 0 | 2G | 0 | | | | |
| Pyrimidine with CO₂CH(CH₃)CH=CH₂, CH₃, SO₂NHCONH-phenyl | 0.05 | 5G | 9H | 3H | 1C,7G | 1C | 2C,6H | 1C | 3G | 0 | 2C,8H | 2C,8H | | | | |

TABLE A-continued

| Structure | | | | | | | | | | | | | | |
|---|---|---|---|---|---|---|---|---|---|---|---|---|---|---|
| Structure 1 (CH3, pyrrolidinone-CN phenyl, SO2NHCONH) | 0.05 | 9H | 9H | 1C | 1C | 2C,9H | 1C,6G | 1C,8H | 1C,5G | 10E | 2C,9H | | | |
| Structure 2 (CH3, Cl phenyl, SO2NHCONH) | 0.4 | 2G | 8H | 0 | 0 | 2C,5H | 0 | 2C,6G | 0 | 2C,8G | 1C | | | |
| Structure 3 (CH3, Cl phenyl CO2CH3, SO2NHCONH) | 0.4 | 8G | 9H | 5G | 10E | 2G | 3C,9H | 1C,8G | 8G | 1G | 2C,9H | | | |
| Structure 4 (OCH3, Cl phenyl, SO2NHCONH) | 0.05 | 0 | 0 | 0 | 0 | 1C,3G | 1C,2G | 1C,4G | 0 | 10E | 2C,9H | | | |
| Structure 5 (OCH3, NO2 phenyl, SO2NHCONH) | 0.05 | 4G | 0 | 5G | 5G | 1C,4G | 9G | 2C,6H | 0 | 2C,7G | 8H | 3C,9H | 2C,7G | 9H | 2C,9H |

TABLE A-continued

| Structure | | | | | | | | | | | | | |
|---|---|---|---|---|---|---|---|---|---|---|---|---|---|
| CO₂CH₃ / OCH₃ pyrimidine / SO₂NHCONH-phenyl-CH₃-furan | 0.05 | 9G | 9G | 1C,3G | 10E | 3C,7G | 3C,9H | 1C,9G | 1C,9G | 3C,9H | 1H | 10E | 5C,9H |
| CO₂CH(CH₃)₂ / OCH₃ pyrimidine / SO₂NHCONH-phenyl | 0.05 | 9G | 9H | 0 | 8G | 1C | 2C,9H | 1C,8G | 7G | 1C,8H | 0 | 10E | 2C,9H |
| SO₂NHCONH / OCH₃ pyrimidine / CO₂CH₃-thiophene | 0.05 | 5G | 9G | 0 | 4G | 2C | 2C,9H | 2G | 2C,9H | 0 | 8H | 2C,8G |
| CO₂CH₃ / CH₃ pyrimidine / SO₂NHCONH-furan | 0.4 | 8G | 9H | 9G | 10E | 9G,5C | 5C,9H | 3C,8G | 9H | 10H | 8H | 10E | 5C,9H |
| SO₂NHCONH / CH₃ pyrimidine / CO₂CH₃-furan | 0.05 | 0 | 6H | 2G | 3G | 0 | 0 | 0 | 0 | 2C,7G | 2A | 2C,8H | 2C,3H |

TABLE A-continued

| Structure | Rate | | | | | | | | | | | | | |
|---|---|---|---|---|---|---|---|---|---|---|---|---|---|---|
| Phenyl with SO₂N(CH₃)₂ and SO₂NHCONH— (furo-pyrimidine with CH₃, CH₃) | 0.05 | 9G | 9H | 7G | 10E | 2C,8G | 9H | 2C,7H | 9G | 9G | 5C,9G | 7G | 10E | 3C,9H |
| Phenyl with OSO₂CH₃ and OSO₂NHCONH— (furo-pyrimidine with CH₃, CH₃) | 0.4 | 1H | 8H | 2G | 10E | 5G,1C | 2C,7H | 4G | 1C,8G | 2U,9G | 2C,8H | 5C,9H | 10H | |
| Phenyl with Cl and SO₂NHCONH— (furo-pyrimidine with N(CH₃)₂, CH₃) | 0.05 | 0 | 0 | 0 | 0 | 2G | 2G | 2G | 0 | 0 | 0 | 0 | 0 | 0 |
| Phenyl with CO₂CH₃ and SO₂NHCONH— (furo-pyrimidine with N(CH₃)₂, CH₃) | 0.05 | 0 | 4H | 0 | 0 | 5G | 6H | 5G | 5G | 2C,9G | 3C,9H | 3C,9H | 2C,8H | |
| Phenyl with SO₂N(CH₃)₂ and SO₂NHCONH— (furo-pyrimidine with N(CH₃)₂, CH₃) | 0.05 | 0 | 0 | 0 | 0 | 5G | 5G | 7H | 2G | 2C,7G | 0 | 2C,6G | 3C,8H | |

TABLE A-continued

| Structure | | | | | | | | | | | | |
|---|---|---|---|---|---|---|---|---|---|---|---|---|
| ![structure with Cl, SCH3, SO2NHCONH, CH3, O] | 0.4 | 1C | 8H | 2C,3H | 3G | 2C | 2G | 0 | 0 | 3C | 0 | 2C,4G 1C |
| ![structure with CO2CH3, SCH3, SO2NHCONH, CH3, O] | 0.4 | 8G | 9H | 6G | 8G | 1C,6G | 3C,9G | 2C,9H | 1C,7G | 9G | 6H | 10E 2C,9G |
| ![structure with SO2N(CH3)2, SCH3, SO2NHCONH, CH3, O] | 0.4 | 5G | 9H | 2H,2C | 2G | 1C,7G | 2C,9H | 1C,8G | 3G | 2C,8H | 1H | 2C,8G 9H |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that the compounds are useful as pre-emergence treatments for weed control in crops such as soybeans and cotton.

TABLE B
PRE-EMERGENCE ON FALLSINGTON SILT LOAM

| Structure | Rate kg/ha | Crabgrass | Barnyard-grass | Sorghum | Wild Oats | Johnson-grass | Dallis-grass | Giant foxtail | Ky. bluegrass | grass | Sugarbeets | Corn | Mustard |
|---|---|---|---|---|---|---|---|---|---|---|---|---|---|
|  | 0.031<br>0.125 | 4G<br>5G | 5G<br>8C,8G | 4G<br>4G | 0<br>0 | 6G<br>6G,3H | —<br>— | 4G,3C<br>6G,6C | 4G<br>6G | 4G<br>8G | 3G<br>5G | 3G<br>5G,5H | 7G,3C<br>8G,8C |
| 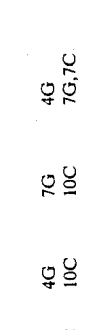 | 0.031<br>0.125 | 5G<br>7G | 6G<br>7G | 5G<br>8G,7H | 5G<br>7G | 6G<br>9C,9G | —<br>— | 4G<br>7G,3C | 4G<br>10C | 7G<br>10C | 4G<br>7G,7C | 2G<br>4G | 7G,6C<br>9G,9C |
| 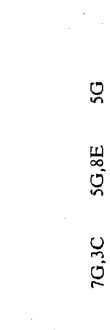 | 0.031<br>0.125 | 6G<br>8G,3H | 6G<br>9G,9C | 10E<br>10E | 6G<br>8G,8C | 8G,3H<br>9G,9C | —<br>— | 3G<br>5G,4C | 7G,3C<br>10C | 5G,8E<br>10E | 5G<br>10C | 6G,5H<br>9G,9C | 9G,9C<br>10C |
| 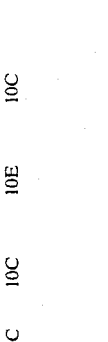 | 0.031<br>0.125 | 4G<br>4G | 5G<br>5G | 4G<br>7G,3H | 0<br>3G | 5G<br>8C,7C | —<br>— | 4G<br>4G,3C | 0<br>4G | 0<br>6G | 5G<br>7G,7C | 0<br>3G,3H | 7G<br>8G,5C |
|  | 0.031<br>0.125 | 5G<br>5G | 6G<br>7G | 6G,3H<br>7G,5H | 2G<br>6G | 7G<br>8G,3H | —<br>— | 5G<br>7G,4C | 7G,5C<br>9G,9C | 5G<br>10C | 3G<br>7G,8C | 5C<br>6G,5H | 7G,3C<br>8G,8C |
| 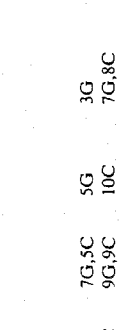 | 0.031<br>0.125 | 0<br>3G | 3G,2C<br>7G,5H | 5G,3H<br>7G,5H | 0<br>4G | 3G<br>6G,3H | 3G<br>6G | 4G<br>6G,3H | 5G<br>7G | 7G<br>7G | 5G<br>6G,7C | 2G<br>4G | 6G,3C<br>7G,8C |

TABLE B-continued

PRE-EMERGENCE ON FALLSINGTON SILT LOAM

| Structure | Rate | | | | | | | | | | | |
|---|---|---|---|---|---|---|---|---|---|---|---|---|
| CH₃ / CH₃ phenyl-SO₂NHCONH-pyrimidine-CH=C(CH₃)O | 0.031<br>0.125 | 3G<br>5G | 4G,3C<br>6G,3C | 6G,2H<br>8G,5H | 0<br>3G | 5G<br>6G | 5G<br>6G | 3G<br>6G,3H | 4G<br>7G | 7G<br>7G | 2G<br>5G,4C | 0<br>5G,3H | 7G<br>8G,5C |
| OCH₃ / CH₃ analogue | 0.063<br>0.25 | 3G<br>5G | 5G<br>8G,3H | 2G<br>6G,3H | 4G<br>7G | 0<br>5G,3H | 3G<br>5G,3H | 3G<br>5G | 4G<br>6G | 5G<br>5G | 4G<br>7G,7C | 0<br>2G | 7G<br>7G,4C |
| CO₂CH₂CH₃ / CH₃ analogue | 0.031<br>0.125 | 4G<br>3G | 4G<br>6G | 7G,3H<br>10C | 3G<br>4G | 5G,3H<br>8G,5H | 6G<br>7G,3H | 4G<br>8G,5H | 7G<br>7G,3G | 7G<br>9G,9E | 5G,3H<br>9G,9C | 0<br>8G,3H | 6G<br>7G |
| SO₂CH₃ / CH₃ analogue | 0.031<br>0.125 | 0<br>0 | 0<br>2G | 2G<br>6G,3H | 0<br>4G | 0<br>5G,5H | 0<br>5G,3H | 0<br>5G,3H | 3G<br>6G,3C | 0<br>8G,5C | 0<br>5G | 0<br>1U | 5G<br>6G |
| CO₂CH₃ / OCH₃ analogue | 0.031<br>0.125 | 0<br>3G | 0<br>4G,2C | 7G,5H<br>10C | 3G<br>5G | 4G<br>5G,3H | 5G<br>7G,3H | 3G<br>6G,5H | 7G<br>8G,8C | 6G<br>8G,8C | 6G,5C<br>7G,6C | 2H<br>6G,3H | 6G<br>6G,3C |

TABLE B-continued

PRE-EMERGENCE ON FALLSINGTON SILT LOAM

| Structure | Rate | | | | | | | | | | | | | | |
|---|---|---|---|---|---|---|---|---|---|---|---|---|---|---|---|
| Structure with CO₂CH(CH₃)₂, OCH₃, SO₂NHCONH | 0.031<br>0.125 | 0<br>0 | 4G,3H<br>5G,3H | 5G,3H | 4G<br>2H | 0<br>2G | 0<br>3G | 0<br>3G | 0<br>4G | 5G<br>6G,3C | 0<br>0 | 6G,3C<br>6G,4C |
| Structure with SO₂N(CH₃)₂, CH₃, SO₂NHCONH | 0.031<br>0.125 | 5G<br>7G,2H | 8G,5H<br>10C | 9G,5H<br>10C | 3G<br>7G,3H | 5G<br>8G,3H | 6G<br>8G,6C | 8G,8C<br>10C | 5G<br>6G,3H | 6G,3C<br>10E | 4G<br>8G,8C | 3G,5H<br>8G,5H | 6G,3C<br>7G,5C |
| Structure with OSO₂CH₃, CH₃, SO₂NHCONH | 0.031<br>0.125 | 0<br>4G | 2C<br>4G,2C | 4G,2H<br>7G,5H | 0<br>2G | 6G,3H | 0<br>5G | 3G<br>0 | 3G<br>3G | 3G<br>5G,5C | 0<br>2G | 0<br>0 | 0<br>3G |
| Structure with CO₂CH₃, CH₃, SO₂NHCONH (furan) | 0.031<br>0.125 | 3G<br>7G,3H | 5G,3C<br>6G,3C | 8G,5H<br>10C | 0<br>3G | 7G,5H<br>8G,5H | 0<br>5G | 0<br>3H | 5G,3H<br>7G,7H | 5G<br>10C | 5G<br>8G,7C | 5G,2H<br>6G,5H | 7G<br>8G,5C |
| Structure with CO₂CH₃, SCH₃, SO₂NHCONH | 0.063<br>0.25 | 0<br>0 | 0<br>3G | 0<br>5G,3H | 0<br>2G | 0<br>2H | 0<br>2G | 0<br>3G | 0<br>5G | 0<br>4G | 0<br>5G | 0<br>0 | 6G<br>7G,4C |

TABLE B-continued

PRE-EMERGENCE ON FALLSINGTON SILT LOAM

| Structure | Rate kg/ha | Cocklebur | Pigweed | Nutsedge | Cotton | Morningglory | Cassia | Teaweed | Velvetleaf | Jimsonweed | Soybean | Rice | Wheat |
|---|---|---|---|---|---|---|---|---|---|---|---|---|---|
| $SO_2N(CH_3)_2$ / $SO_2NHCONH$-pyrimidine-$SCH_3$ structure | 0.063 / 0.25 | 0 / 0 | 6G / 10E | 0 / 0 | 0 / 2G | 3G / 4G | 4G / 7G | 3G / 10C | 3G / 5G,5C | 0 / 3G | 2G / 3G | 6G / 10C | 2G / 5G |
| 2-Cl-phenyl-$SO_2NHCNH$ / furan structure | 0.031 / 0.125 | 0 / 0 | 8G,8C / 10E | 0 / 0 | 4G / 5G | 4G / 3G | 5G / 7G,7C | 3G / 6G,5C | 4G / 6G,3H | 3G / 8G,8C | 4G / 6G,5H | 5G / 7G | 2G / 4G |
| 2-$NO_2$-phenyl-$SO_2NHCNH$ / furan structure | 0.031 / 0.125 | — / 4G | 10E / 10E | 5G / 7G | 3G / 6G | 5G / 4G | 7G,4C / 6G | 3G / 5G,3H | 3G / 5G,3H | 3G / 7G,3C | 3G / 4G | 8G,8C / 10E | 6G / 7G |
| 2-$CO_2CH_3$-phenyl-$SO_2NHCNH$ / furan structure | 0.031 / 0.125 | 0 / 0 | 3G / 7G,3C | 0 / 5G | 0 / 0 | 4G / 5G | 4G / 4G | 3G / 3G | 4G / 4G | 0 / 3G | 0 / 3G | 4G / 5G | 2G / 4G |
| 2-$CO_2CH_2CH=CH_2$-phenyl-$SO_2NHCNH$ / furan structure | 0.031 / 0.125 | 0 / 4G | 4G / 8G,8C | 3G / 7G | 0 / 5G,3H | 2G / 4G | 3G / 3G | 0 / 3G | 0 / 5G,2H | 0 / 7G,7C | 3G / 3G | 5G / 8G,8C | 5G / 6C |
| 2-$CO_2CH(CH_3)_2$-phenyl-$SO_2NHCNH$ / furan structure | | | | | | | | | | | | | |

TABLE B-continued

PRE-EMERGENCE ON FALLSINGTON SILT LOAM

| Compound | Rate | | | | | | | | | | | | | | | | |
|---|---|---|---|---|---|---|---|---|---|---|---|---|---|---|---|---|---|
| ![structure with pyrrolidinone-CN, CH3, N, N, SO2NHCONH, CH3, O, CH3] | 0.031<br>0.125 | 0<br>3G | —<br>— | 5G<br>8G | 0<br>3G | 3G<br>6G | 3G<br>3G | 0<br>4G | 0<br>4G | 0<br>4G | 0<br>3G | 5G<br>10C | 0<br>3G |
| ![structure with CH3, CH3, N, N, SO2NHCONH, CH3, O, CH3] | 0.031<br>0.125 | 0<br>0 | 10E<br>10E | 0<br>3G | 0<br>3G | 3G<br>2G | 3G<br>6G | 6G,5C<br>9G,9C | 3G<br>7G,8C | 2G<br>5G | 0<br>0 | 10C<br>10E | 2G<br>0 |
| ![structure with NO2, OCH3, N, N, SO2NHCONH, CH3, O, CH3] | 0.063<br>0.25 | 0<br>3G | 10C<br>10C | 0<br>5G | 0<br>— | 0<br>0 | 0<br>3G | 0<br>3G | 0<br>3G | 6G,5C | 0<br>2G | 2G<br>10C | 0<br>0 |
| ![structure with CO2CH2CH3, CH3, N, N, SO2NHCONH, CH3, O, CH3] | 0.031<br>0.125 | 3G<br>4G | 9G,9C<br>10E | 0<br>0 | 0<br>0 | 0<br>3G | 3G<br>5G,5C | 0<br>3G | 0<br>2G | 0<br>5G | 0<br>2G | 10C<br>10E | 2G<br>6G,3H |
| ![structure with SO2CH3, CH3, N, N, SO2NHCONH, CH3, O, CH3] | 0.031<br>0.125 | 0<br>0 | 0<br>0 | 0<br>0 | 0<br>0 | 0<br>0 | 0<br>0 | 0<br>0 | 0<br>0 | 0<br>0 | 0<br>0 | 7G,3H<br>10E | 0<br>4G |

TABLE B-continued

PRE-EMERGENCE ON FALLSINGTON SILT LOAM

| Structure | Rate | | | | | | | | | | | |
|---|---|---|---|---|---|---|---|---|---|---|---|---|
| CO₂CH₃ / OCH₃ / SO₂NHCONH- cyclohexane / furan-CH₃ | 0.031<br>0.125 | 0<br>0 | 9G,9C<br>10C | 0<br>3G | 0<br>2G | 0<br>0 | 0<br>0 | 0<br>0 | 0<br>0 | 0<br>4G,3H | 8G,6E<br>10E | 3G<br>6G,3C |
| CO₂CH(CH₃)₂ / OCH₃ / SO₂NHCONH- cyclohexane / furan-CH₃ | 0.031<br>0.125 | 0<br>0 | 5G<br>5G | 0<br>0 | 0<br>0 | 0<br>2G | 0<br>0 | 0<br>0 | 0<br>0 | 0<br>0 | 5G<br>5G | 3G<br>2G,2C |
| SO₂N(CH₃)₂ / CH₃ / SO₂NHCONH- cyclohexane / furan-CH₃ | 0.031<br>0.125 | 0<br>5G | 5G<br>9G,9C | 0<br>0 | 0<br>3G | 3G<br>5G | 3G<br>5G | 0<br>0 | 4G,3H<br>5G,2C | 0<br>2H | 8G,5H<br>10E | 2G<br>5G |
| OSO₂CH₃ / CH₃ / OSO₂NHCONH- cyclohexane / furan-CH₃ | 0.031<br>0.125 | 0<br>0 | C<br>0 | 4G<br>10E | 0<br>4G,2H | 0<br>0 | 3G<br>3G | 0<br>0 | 0<br>0 | 0<br>0 | 3G<br>2G | 0<br>0 |
| CO₂CH₃ / CH₃ / SO₂NHCONH- furan / furan-CH₃ | 0.031<br>0.125 | 0<br>6G | 5G<br>5G | 4G<br>10E | 0<br>3G | 6G<br>7G | 3G<br>3G | 3G<br>5G,5H | 3G<br>5G | 0<br>3G,2H | 10E<br>10E | 0<br>4G |

TABLE B-continued
PRE-EMERGENCE ON FALLSINGTON SILT LOAM

| Compound | Rate | | | | | | | | | | | |
|---|---|---|---|---|---|---|---|---|---|---|---|---|
| ![structure with CO2CH3, SO2NHCONH, SCH3, CH3, O, N] | 0.063 | 0 | 0 | 8G,8C | 0 | 0 | 0 | 0 | 0 | 0 | 0 | 3G | 0 |
| | 0.25 | 3G | 3G | 3G | 0 | 0 | 0 | 0 | 0 | 0 | 0 | 6G,3H | 0 |
| ![structure with SO2N(CH3)2, SO2NHCONH, SCH3, CH3, O, N] | 0.063 | 0 | 0 | 5G | 0 | 0 | 0 | 0 | 0 | 0 | 0 | 0 | 0 |
| | 0.25 | 0 | 0 | 7G | 0 | 0 | 0 | 0 | 0 | 0 | 0 | 2G | 0 |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately two weeks after planting, the young plants and the soil around them were sprayed overall with the test chemicals dissolved in a nonphytotoxic solvent. Two weeks after treatment, all species were compared to untreated controls and visually rated for response to treatment. The rating system was as described previously for Test A. The data are presented in Table C. Several of the compounds tested by this procedure are useful for the post-emergence control of weeds in wheat and cotton.

TABLE C

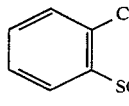

| Rate kg/ha | 0.250 | 0.063 |
|---|---|---|
| Soybeans | 10G,8C | 10G,7C |
| Velvetleaf | 10G,2C | 9G,2C |
| Sesbania | 10G | 7G,5C |
| Cassia | 2G,2C | 4G |
| Cotton | 5G,5C | 5G |
| Morningglory | 6G,6C | 6G,2C |
| Alfalfa | 7G,4C | 5G |
| Jimonweed | 10G | 8G |
| Cocklebur | 0G | 2G,3C |
| Sunflower | — | — |
| Mustard | — | — |
| Sugarbeets | — | — |
| Corn | 8G,5U | 7G,5U |
| Crabgrass | 9G | 5G |
| Rice | 8G,8C | 8G,7C |
| Nutsedge | 4G,2C | 2G |
| Barnyardgrass | 10C | 8G,4C |
| Wheat | 5G,4C | 4G,3C |
| Giant Foxtail | — | — |
| Wild Oats | 7G,4C | 6G,2C |
| Sorghum | 6G,1H | 5G,1H |

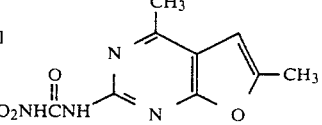

| Rate kg/ha | 0.250 | 0.063 | 0.125 | 0.031 |
|---|---|---|---|---|
| Soybean | 9G,4C | 10G,7C | 10C | 9G,9C |
| Velvetleaf | 10C | 9G | 9G,8C | 7G,5C |
| Sesbania | 10C | 10C | 10C | 10C |
| Cassia | 4G,2C | 2G | 9G,5C | 9G,5C |
| Cotton | 8G,2C | 7G,2C | 9G,9C | 6G,5C |
| Morningglory | 7G,7C | 5G,2C | 8G,7C | 9G,9C |
| Alfalfa | 8G,6C | 5G | 8G,4C | 7G,2C |
| Jimsonweed | — | 9G | 0 | — |
| Cocklebur | 10G | 9G,4C | — | 3G |
| Sunflower | — | — | 10C | 5G |
| Mustard | — | — | 10C | 9G,9C |
| Sugarbeets | — | — | 10C | 9G,9C |
| Corn | 10G,9U | 7G,6U | 7G,7C | 10C |
| Crabgrass | 9G,6C | 7G | 7G,5C | 7G |
| Rice | 9G,5C | 8G,5C | 8G,7C | 7G,4C |
| Nutsedge | 6G,4C | 7G,5C | 2G | 0 |
| Barnyardgrass | 9G,8C | 10C | 8G,5C | 8G,5C |
| Wheat | 5G,5C | 5G,3C | 7G,1C | 5G |
| Giant Foxtail | — | 9G,4C | 9G,8C | 7G |
| Wild Oats | 8G,6C | 6G,4C | 7G | 5G |
| Sorghum | 7G,3U | 7G,2C | 3G | 7G,3C |

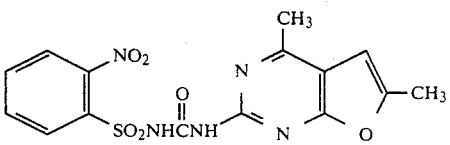

| Rate kg/ha | 0.008 | 0.063 | 0.016 |
|---|---|---|---|
| Soybeans | 8G,7C | 10C | 10C |
| Velvetleaf | 2G,2C | 9G,5C | 8G,3C |
| Sesbania | 10G | 10G | 10G |
| Cassia | 7G,1C | 9G,9C | 10G,9C |
| Cotton | 6G,5C | 8G,2C | 8G |
| Morningglory | 4G,5C | 9G,5C | 8G,6C |
| Alfalfa | 2G,2C | 8G,8C | 9G,8C |
| Jimsonweed | 2C | 9G,6C | 8G |
| Cocklebur | 0 | 9G,6C | 8G |
| Sunflower | 0 | 9G,8C | 8G |
| Mustard | 5G | 10C | 10C |
| Sugarbeets | 5G | 9G,7C | 10C |
| Corn | 7G,7C | 10C | 10C |
| Crabgrass | 0 | 9G,9C | 6G |
| Rice | 4G,2C | 10C | 9G,9C |
| Nutsedge | 0 | — | 0 |
| Barnyardgrass | 8G,1C | 9G,9C | 10C |
| Wheat | 0 | 9G,5C | 5C |
| Giant Foxtail | 0 | 9G,9C | 8G |
| Wild Oats | 3G | 9G,9C | 8G,7C |
| Sorghum | 2G | 8G,6C | 7G,3C |

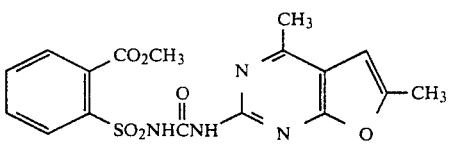

| Rate kg/ha | 0.250 | 0.063 |
|---|---|---|
| Soybeans | 10C | 5G,5C |
| Velvetleaf | 10G,7C | 9G,5C |
| Sesbania | 10C | 10G,5C |
| Cassia | 6G,2C | 5G |
| Cotton | 10G | 8G,2C |
| Morningglory | 7G,7C | 6G,6C |
| Alfalfa | 9G,8C | 9G,6C |
| Jimsonweed | 8G | — |
| Cocklebur | 10C | 10C |
| Sunflower | — | — |
| Mustard | — | — |
| Sugarbeets | — | — |
| Corn | 10G,9U | 10G,9U |
| Crabgrass | 9G,8C | 9G,3C |
| Rice | 9G,8C | 9G,7C |
| Nutsedge | 9G,9C | 9G,7C |
| Barnyardgrass | 10C | 10C |
| Wheat | 6G,4C | 5G,3C |
| Giant Foxtail | 10C | — |
| Wild Oats | 8G,7C | 8G,5C |
| Sorghum | 9G,8C | 10G,6C |

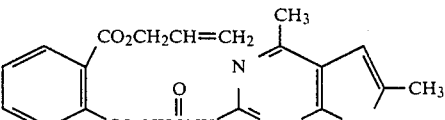

| Rate kg/ha | 0.250 | 0.016 | 0.063 |
|---|---|---|---|
| Soybean | 10G,7C | 10G,4C | 9G,5H |
| Velvetleaf | 9G,3C | 6G | 3G |
| Sesbania | 10G | 8G,2C | 7G,4C |
| Cassia | 7G,2C | 7G,5C | 3G,5C |
| Cotton | 7G,6C | 7G,3C | 5G,2C |
| Morningglory | 6G,4C | 5G,2C | 4G,2C |

TABLE C-continued

| | | | |
|---|---|---|---|
| Alfalfa | 7G,2C | 5G | 0 |
| Jimsonweed | 8G | — | 7G |
| Cocklebur | 10C | 6G,2H | 4G |
| Sunflower | — | — | — |
| Mustard | — | — | — |
| Sugarbeets | — | — | — |
| Corn | 10G,8U | 7G,4U | 5G,2U |
| Crabgrass | 0 | 0 | 0 |
| Rice | 8G | 7G | 7G |
| Nutsedge | 9G,4C | 8G,2C | 8G,2C |
| Barnyardgrass | 6G,6C | 4G,2C | 4G |
| Wheat | 5G,2C | 1G | 2G |
| Giant Foxtail | — | — | 4G |
| Wild Oats | 5G,4C | 3G | 1G |
| Sorghum | 6G,2C | 5G | 4G |

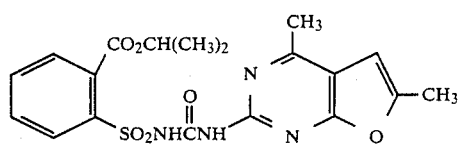

| Rate kg/ha | 0.250 | 0.063 |
|---|---|---|
| Soybeans | 10G,5C | 10G,4C |
| Velvetleaf | 7G | 7G |
| Sesbania | 6G,2C | 5G,2C |
| Cassia | 6G | 5G |
| Cotton | 9G | 5G |
| Morningglory | 6G,7C | 5G,5C |
| Alfalfa | 7G | 8G,5C |
| Jimsonweed | — | 8G |
| Cocklebur | 10C | 8G,5C |
| Sunflower | — | — |
| Mustard | — | — |
| Sugarbeets | — | — |
| Corn | 9G,7U | 7G,6U |
| Crabgrass | 5G | 0 |
| Rice | 9G,5C | 8G,5C |
| Nutsedge | 9G,4C | 9G,2C |
| Barnyardgrass | 8G,7C | 8G,5C |
| Wheat | 8G,3C | 7G,3C |
| Gaint Foxtail | 8G,4C | 6G,2C |
| Sorghum | 6G | 7G,2C |

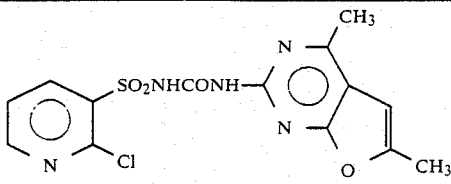

| Rate kg/ha | 0.063 | 0.016 |
|---|---|---|
| Soybeans | 3G | 1G,1C |
| Velvetleaf | 8G,5C | 6G,1C |
| Sedbania | 9G,8C | 8G,5C |
| Cassia | 1C | 1C |
| Cotton | 7C,5C | 4G,2C |
| Morningglory | 8G,3C | 2G,4C |
| Alfalfa | 1G | 0 |
| Jimsonweed | — | — |
| Cocklebur | 0 | 0 |
| Sunflower | 3G | 3G |
| Mustard | 6G | 5G |
| Sugarbeets | 7G | 6G |
| Corn | 7G,1C | 5G,1U |
| Crabgrass | 6G | 0 |
| Rice | 7G,4C | 7G,2C |
| Nutsedge | 7G,3C | 7G |
| Barnyardgrass | 7G,7C | 4G,3C |
| Wheat | 4G | 1G |
| Giant Foxtail | 9G | 0 |
| Wild Oats | 0 | 0 |
| Sorghum | 9G,2C | 7G,1C |

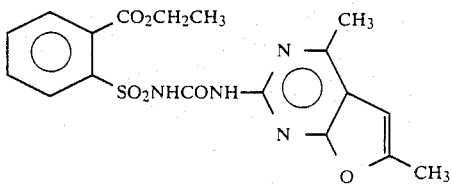

| Rate kg/ha | 0.250 | 0.063 |
|---|---|---|
| Soybeans | 10C | 10C |
| Vetvetleaf | 6G | 4G |
| Sesbania | 10C | 10C |
| Cassia | 10C | 7G,4C |
| Cotton | 1G | 0 |
| Morningglory | 5G,4C | 2G,1C |
| Alfalfa | 10C | 7G |
| Jimsonweed | — | 0 |
| Cocklebur | 10C | 0 |
| Sunflower | 10C | 7G |
| Mustard | 10C | 7G |
| Sugarbeets | 10C | 6G |
| Corn | 10C | 8G,5U |
| Crabgrass | 3G | 0 |
| Rice | 7G,6C | 5G |
| Nutsedge | 4G | 2G |
| Barnyardgrass | 9G,9C | 6G,2C |
| Wheat | 4G,2C | 4G |
| Giant Foxtail | 8G,6U | 5G |
| Wild Oats | 2G | 1G |
| Sorghum | 7G,9U | 7G,6U |

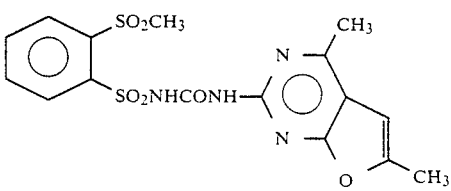

| Rate kg/ha | 0.031 | 0.008 |
|---|---|---|
| Soybeans | 9G,9G | 8G,7C |
| Velvetleaf | 10C | 9G,7C |
| Sesbania | 10C | 9G,5C |
| Cassia | 10C | 9G,5C |
| Cotton | 10C | 8G,3C |
| Moringglory | 7G,5C | 4G |
| Alfalfa | 10C | 6G,4C |
| Jimsonweed | 8G | 4G |
| Cocklebur | 8G | 6G,1H |
| Sunflower | 10C | 8G |
| Mustard | 10C | 8G |
| Sugarbeets | 10C | 9G |
| Corn | 10C | 10G,7C |
| Crabgrass | 8G | 0 |
| Rice | 9C | 9G,9C |
| Nutsedge | 8G,7C | 2G |
| Barnyardgrass | 9G,5C | 8G |
| Wheat | 8G,5C | 8G,7C |
| Giant Foxtail | 9G,9C | 8G, |
| Wild Oats | 8G | 8G,2C |
| Sorghum | 7G,1C | 7G,1C |

| Rate kg/ha | 0.063 | 0.016 |
|---|---|---|
| Soybeans | 10C | 9G,9C |
| Velvetleaf | 9G | 7G,2C |
| Sesbania | 9G,8C | 9G,7C |

TABLE C-continued

| | | |
|---|---|---|
| Cassia | 9G,5C | 5G,7C |
| Cotton | 7G,1C | 6G |
| Morningglory | 7G,2C | 5G,1C |
| Alfalfa | 2G,2C | 3G,1C |
| Jimsonweed | 0 | 0 |
| Cocklebur | 4G | 4G |
| Sunflower | 4G,1C | 4G |
| Mustard | 4G | 4G |
| Sugarbeets | 3G | 2G |
| Corn | 9G,1U | 9G,1U |
| Crabgrass | 1C | 3G |
| Rice | 9G,9C | 8G,8C |
| Nutsedge | 0 | 0 |
| Barnyardgrass | 10C | 7G |
| Wheat | 5G,2C | 4G |
| Giant Foxtail | 7G,2C | 4G,1C |
| Wild Oats | 8G,1C | 6G,1C |
| Sorghum | 8G,1H | 6G,1U |

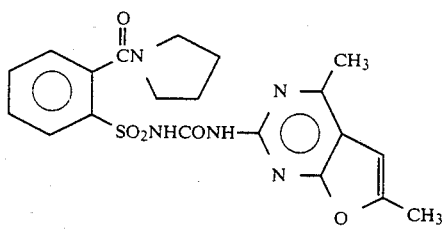

| Rate kg/ha | 0.125 | 0.063 | 0.016 |
|---|---|---|---|
| Soybeans | 10G,9C | 10G,8C | 3G |
| Velvetleaf | 5G,3C | 3G,2C | 1C |
| Sesbania | 4G | 2G | 0 |
| Cassia | 2G,1C | 2G,2C | 1C |
| Cotton | 2G | 2G | 1G |
| Morningglory | 4G,4C | 3G,1C | 2G,1C |
| Alfalfa | 1G,1C | 1C | 0 |
| Jimsomweed | 0 | 0 | 0 |
| Cocklebur | 2G | 0 | 0 |
| Sunflower | 0 | 0 | 0 |
| Mustard | 9G | 9G | 5G |
| Sugarbeets | 7G | 6G | 3G |
| Corn | 10C | 8G,4U | 4G,2H |
| Crabgrass | 1G | 5G | 1C |
| Rice | 8G,5C | 6G,3C | 5G,2C |
| Nutsedge | 2G | 0 | 0 |
| Barnyardgrass | 5G,2C | 6G,2C | 4G |
| Wheat | 5G | 5G | 1G |
| Giant Foxtail | 8G | 7G | 1G |
| Wild Oats | 5G | 4G | 3G |
| Sorghum | 7G,2C | 6G | 1G,1C |

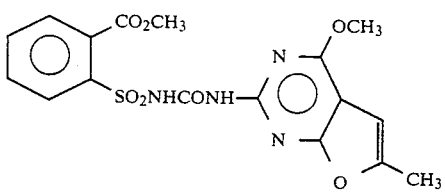

| Rate kg/ha | 0.125 | 0.063 |
|---|---|---|
| Soybeans | 10G,8C | 10G,8C |
| Velvetleaf | 9G,4C | 8G,4C |
| Sesbania | 9G,2C | 9G,4C |
| Cassia | 10G,8C | 10G,8C |
| Cotton | 9G,5C | 8G,4C |
| Morningglory | 9G,4C | 9G,4C |
| Alfalfa | 9G,4C | 7G,3C |
| Jimsonweed | 9G | — |
| Cocklebur | — | 10G,3C |
| Sunflower | 8G,3C | 8G,3C |
| Mustard | 10G,5C | 9G,4C |
| Sugarbeets | 8G,4C | 9G,5C |
| Corn | 9G,1C | 9G,3I |
| Crabgrass | 8G,3C | 7G,3C |
| Rice | 10G,7C | 7G,3C |
| Nutsedge | 9G,4C | 5G,2C |
| Barnyardgrass | 9G,6C | 9G,2C |
| Wheat | 7G,2C | 6G |
| Giant Foxtail | 7G,3C | 8C,5G |
| Wild Oats | 7G,2C | 6G,1C |
| Sorghum | 9G,2C | 9G,2U |

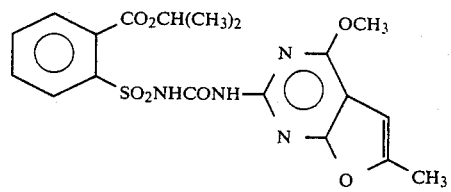

| Rate kh/ha | 0.125 | 0.063 |
|---|---|---|
| Soybeans | 7G,3C | 7G,2C |
| Velvetleaf | 4G,2C | 4G |
| Sesbania | 9G,5C | — |
| Cassia | 9G,4C | 7G,3C |
| Cotton | 5G,1C | 7G,3C |
| Morningglory | 9G,4C | 8G,4C |
| Alfalfa | 7G,3C | 9G,4C |
| Jimsonweed | 8G | 7G |
| Cocklebur | 8G,4C | 5G,4C |
| Sunflower | 7G,3C | 7G,3C |
| Mustard | 7G,3C | 7G,2C |
| Sugarbeets | 6G | 5G |
| Corn | 8G,5C | 7G,3C |
| Crabgrass | 7G,2C | 5G,3C |
| Rice | 8G,3C | 7G,3C |
| Nutsedge | 4G | 0 |
| Barnyardgrass | 10G,5C | 10G,5C |
| Wheat | 6G | 4G |
| Giant Foxtail | 7G,3C | 6G,2C |
| Wild Oats | 6G | 4G |
| Sorghum | 10G,1C | 10G,2C |

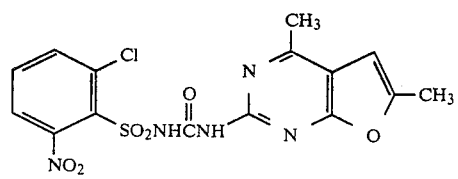

| Rate kg/ha | 0.063 | 0.016 |
|---|---|---|
| Soybeans | 10G,5C | 10G,5C |
| Velvetleaf | 8G,2C | 7G,2C |
| Sesbania | 10C | 10C |
| Cassia | 9G | 6G,3C |
| Cotton | 8G,2C | 5G |
| Morningglory | 3G,3C | 3C |
| Alfalfa | 8G,3C | 7G |
| Jimsonweed | 7G | 0 |
| Cocklebur | 10G,5C | 3G |
| Sunflower | 9G,3C | 8G,1C |
| Mustard | 4G,2C | 1I |
| Sugarbeets | 6G,3C | 1I |
| Corn | 7G | 5G,4H |
| Crabgrass | 7G | 4G |
| Rice | 8G | 5G |
| Nutsedge | 5G | 4G |
| Barnyardgrass | 6G,2C | 4G |
| Wheat | 4G | 5G |
| Giant Foxtail | 7G,2C | 2G |
| Wild Oats | 6G | 3G |
| Sorghum | 6G,2C | 4G |

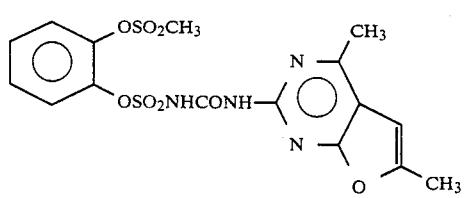

TABLE C-continued

| Rate kg/ha | 0.500 | 0.125 |
|---|---|---|
| Soybeans | 9G,7C | 9G,5C |
| Velvetleaf | 7G,4C | 1C |
| Sesbania | 9G,4C | 8G,4C |
| Cassia | 3C | 5G |
| Cotton | 4G | 4G |
| Morningglory | 2G,5C | 2G,5C |
| Alfalfa | 7G,2C | 7G |
| Jimsonweed | 0 | — |
| Cocklebur | 9G,7C | 1G |
| Sunflower | 6G,2C | 1G,1L |
| Mustard | 9G,8C | 4G |
| Sugarbeets | 8G,1C | 3G |
| Corn | 10C | 8G,4H |
| Crabgrass | 0 | 0 |
| Rice | 3G,2C | 2G,2C |
| Nutsedge | 4G | 7G |
| Barnyardgrass | 0 | 3G |
| Wheat | 2G,1C | 2G |
| Giant Foxtail | 0 | 0 |
| Wild Oats | 0 | 0 |
| Sorghum | 8G | 6G |

Test D

The high herbicidal activity of one of the compounds from within the scope of the invention is evident from the results obtained in this test. The experiment concerned pre-emergence applications on soil. The containers used were 25 cm diameter plastic pots filled with Fallsington silt loam. One set of pots was planted to weeds, the seeds of which were uniformly mixed with the top 1.2 cm layer of soil. The species selected were: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*), and pigweed (*Amaranthus retroflexus*). Another set of pots was planted to the following crops with from one to four species per pot: corn (planting depth 3.7 cm), cotton, soybeans, sunflower, Clinton oats, wheat, Black Valentine beans, rice, sorghum, peas, flax, and peanuts (all at 2.5 cm depth), cucumbers, cabbage, alfalfa, safflower, sugarbeets, tomato, spinach, barley, and Kentucky bluegrass (all at 1.2 cm depth). Immediately after planting, the test chemical was applied to the soil surfaces dissolved in a non-phytotoxic solvent. One pot from the weed phase and one of each of the crop species were left untreated for the purpose of comparison. The treated and untreated pots were promptly watered with approximately 4 mm of simulated rainfall and then held in a greenhouse for several weeks. Visual weed and crop response ratings were made 28 days after treatment utilizing the rating system as described above for test procedure A. The data are given in Table D.

TABLE D

[Structure: benzene ring with CO₂CH₃ and SO₂NHC(O)NH- linked to a pyridine ring bearing =C(CH₃)- and CH₃ and O substituents]

| Rate kg/ha | 0.031 | 0.063 | 0.125 | 0.25 |
|---|---|---|---|---|
| CROPS | | | | |
| Corn | — | — | — | 10C |
| Cotton | — | — | — | 8G,8C |
| Soybean | — | — | — | 7G,7H |
| Tobacco | — | — | — | — |
| Sunflower | — | — | — | 8G,8C |
| Cucumber | — | — | — | 8G,8C |
| Wheat | — | — | — | 10E |
| Rice | — | — | — | 10E |
| Oats | — | — | — | 7G,9C |
| Bean | — | — | — | 5G,8C |
| Tomato | — | — | — | 7G,5C |
| Pea | — | — | — | 10E |
| Spinach | — | — | — | 9G,9C |
| Sugarbeet | — | — | — | 10C |
| Peanuts | — | — | — | 7G,3H |
| Kentucky Bluegrass | — | — | — | 8G,8C |
| Flax | — | — | — | 10E |
| Barley | — | — | — | 8G,8C |
| Sorghum | — | — | — | 10E |
| Safflower | — | — | — | 8G,7C |
| Cabbage | — | — | — | 8G,7C |
| Alfalfa | — | — | — | 9G,9C |
| WEEDS | | | | |
| Broadleaves | 7G,4C | 8G,7C | 8G,8C | |
| Grasses | 5G | 7G,5C | 9G,9C | |

Test E

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russia thistle (*Salsola kali*), tansy mustard (*Descuraina pinnata*), smartweed (*Polygonum pennsylvanicum*), tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table E. Some of the compounds provide selective weed control in wheat and barley.

TABLE E

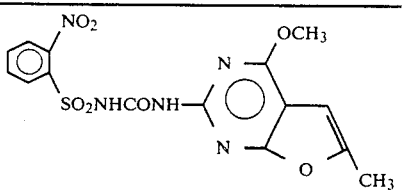

| Rate kg/ha | Post-emergence 0.063 | Pre-emergence 0.063 |
|---|---|---|
| wheat | 1C,2G | 5G |
| barley | 2C,2G | 2C,5G |
| wild oats | 2C,2G | 1C,3G |
| downy brome | 3G | 6G |
| cheatgrass | 2G | 2C,7G |
| blackgrass | 4G | 1C,6G |
| annual bluegrass | 0 | 2C,5G |
| green foxtail | 1C,3G | 1C,6G |
| quackgrass | 1G | 1C,4G |
| Italian ryegrass | 3G | 1C,3G |
| ripgut brome | 1G | 1C,3G |
| Russian thistle | 2G | 0 |
| tansy mustard | 10C | 10E |
| smartweed | — | — |
| jimhill mustard | 2G | 10C |
| Kochia | 2G | 5G |
| shepherd's purse | 1C,6G | 10C |
| false chamomile | 1C,3G | 9C,9G |
| black nightshade | 5G | 8G |
| yellow rocket | 0 | 8G |
| wild mustard | 10C | 5C,9G |
| wild buckwheat | 0 | 4G |

| Rate kg/ha | 0.25 | 0.25 |
|---|---|---|
| wheat | 3G | 6G |
| barley | 2C,2G | 2C,6G |
| wild oats | 2C,4G | 1C,5G |
| downy brome | 5G | 1C,9G |
| cheatgrass | 1C,4G | 3C,7G |
| blackgrass | 2C,7G | 3C,7G |
| annual bluegrass | 1C,4G | 3C,7G |
| green foxtail | 3C,6G | 2C,8G |
| quackgrass | 1C,4G | 2C,7G |
| Italian ryegrass | 1C,4G | 2C,7G |
| ripgut brome | 4G | 6G |
| Russian thistle | 7G | 2G |
| tansy mustard | 10C | 10E |
| smartweed | — | — |
| jimhill mustard | 9C,9G | 10C |
| Kochia | 4C,8G | 2C,7G |
| shepherd's purse | 5C,9G | 10C |
| false chamomile | 10C | 10C |
| black nightshade | 2C,8G | 9G |
| yellow rocket | 0 | 9G |
| wild mustard | 10C | 9G |
| wild buckwheat | 0 | 5G |

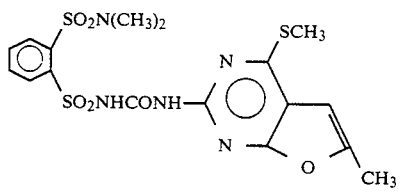

| Rate kg/ha | Post-emergence 0.031 | Pre-emergence 0.031 |
|---|---|---|
| wheat | 0 | 0 |
| barley | 0 | 0 |
| wild oats | 0 | 0 |
| downy brome | 0 | 0 |
| cheatgrass | 2G | 0 |
| blackgrass | 2G | 0 |
| annual bluegrass | 4G | 0 |
| green foxtail | 3G | 0 |
| quackgrass | 0 | 0 |
| Italian ryegrass | 0 | 0 |
| ripgut brome | 0 | 0 |

TABLE E-continued

| | | |
|---|---|---|
| Russian thistle | 0 | 0 |
| tansy mustard | 3C,6G | 4G |
| smartweed | — | — |
| jimhill mustard | 4G | 1G |
| Kochia | 0 | 0 |
| shepherd's purse | 3C,7G | 7G |
| false chamomile | 2C,2G | 1C |
| black nightshade | 2C,1G | 1G |
| yellow rocket | 0 | 6G |
| wild mustard | 5G | 2G |
| wild buckwheat | 0 | 0 |

| Rate kg/ha | 0.125 | 0.125 |
|---|---|---|
| wheat | 3G | 1G |
| barley | 5G | 1C |
| wild oats | 5G | 0 |
| downy brome | 4G | 1G |
| cheatgrass | 5G | 1G |
| blackgrass | 7G | 0 |
| annual bluegrass | 6G | 0 |
| green foxtail | 7G | 1G |
| quackgrass | 1C | 1G |
| Italian ryegrass | 4G | 0 |
| ripgut brome | 3G | 0 |
| Russian thistle | 0 | 0 |
| tansy mustard | 2C,6G | 5C,7G |
| smartweed | — | — |
| jimhill mustard | 1C,4G | 7G |
| Kochia | 1G | 0 |
| shepherd's purse | 2C,7G | 1C,8G |
| false chamomile | 3C,7G | 2C,7G |
| black nightshade | 2C,4G | 6G |
| yellow rocket | 2C,2G | 7G |
| wild mustard | 6G | 2G |
| wild buckwheat | 1G | 1G |

What is claimed is:

1. A compound selected from

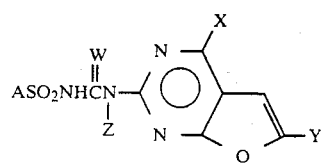

where A is

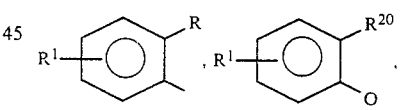

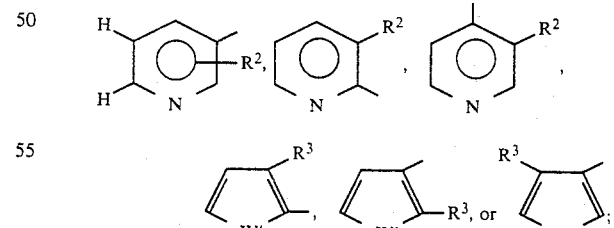

R is H, $C_1$–$C_4$ alkyl, $C_2$–$C_4$ alkenyl, $C_5$–$C_6$ cycloalkenyl, phenyl, phenyl substituted with one Cl or $CH_3$ group, $C_1$–$C_4$ alkoxy, F, Cl, Br, $NO_2$, $NH_2$, CN, $CF_3$, $C(O)R^4$, $S(O)_mR^5$, $SO_2NR^6R^7$, $SO_2N(OCH_3)CH_3$, $SO_2OCH_2CF_3$, $SO_2OCH_2CCl_3$, $BR^8$, $OSO_2R^9$, $CH_2L$ or $CH(CH_3)L$;

Z is H or $CH_3$;

$R^1$ is H, F, Cl, Br, $CF_3$, $C_1$–$C_4$ alkyl, $C_1$–$C_4$ alkoxy or $NO_2$;

$R^4$ is H, $C_1-C_3$ alkyl, $C_1-C_6$ alkoxy, benzyloxy, $C_3-C_6$ alkenyloxy, $C_3-C_6$ alkynyloxy, $C_2-C_6$ haloalkoxy substituted with 1-3 atoms selected from F, Cl or Br, $C_5-C_6$ cycloalkoxy, $O(CH_2CH_2O)_nR^{10}$, $OCH_2CH_2CH_2OR^{10}$, $OCH_2OR^5$, $OCH_2OCH_2CH_2OR^{10}$, $NR^{11}R^{12}$ or $C_1-C_4$ alkylthio;

m is 0, 1 or 2;
n is 1 or 2;
$R^5$ is $C_1-C_4$ alkyl;
$R^6$ and $R^7$ are independently $C_1-C_4$ alkyl, provided that the total number of carbon atoms of $R^6$ and $R^7$ is less than or equal to 5;
B is O or $S(O)_m$;
$R^8$ is $CHF_2$, $CF_3$, $CH_2CF_3$ or $CF_2CHFG$ where G is F, Cl, Br or $CF_3$;
$R^9$ is $C_1-C_4$ alkyl, $CH_2CH_2OCH_3$, $CH_2CH_2CH_2OCH_3$, or $C_1-C_4$ alkyl substituted with 1-3 atoms of F, Cl or Br;
L is Cl, Br, $C_1-C_4$ alkoxy, $C_3-C_4$ alkenyloxy, OH, $S(O)_mR^5$, $CO_2R^{17}$ or $SO_2N(CH_3)_2$;
$R^{10}$ is $CH_3$ or $C_2H_5$;
$R^{11}$ is H, $C_1-C_4$ alkyl, $OCH_3$ or

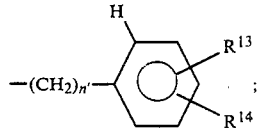

$R^{12}$ is H or $C_1-C_4$ alkyl;
$R^{11}$ and $R^{12}$ can also be taken together to form $-(CH_2)_4-$, $-(CH_2)_5-$ or $-CH_2CH_2OCH_2CH_2-$;
n' is 0 or 1;
$R^{13}$ is H, F, Cl, Br, $NO_2$, CN, $CF_3$, $C_1-C_3$ alkyl, $OCH_3$ or $SCH_3$;
$R^{14}$ is H, F, Cl, Br, $CH_3$ or $OCH_3$;
$R^2$ is H, F, Cl, Br, $C_1-C_4$ alkyl, $C_1-C_4$ alkoxy, $NO_2$, $CO_2R^{15}$, $S(O)_mR^{16}$, $SO_2NR^{18}R^{19}$ or $SO_2N(OCH_3)CH_3$;
$R^{15}$ is $C_1-C_4$ alkyl;
$R^{16}$ is $C_1-C_3$ alkyl;
$R^{17}$ is $C_1-C_4$ alkyl, $C_3-C_4$ alkenyloxy, $CH_2CH_2OCH_3$ or $CH_2CH_2Cl$;
$R^{18}$ and $R^{19}$ are independently $CH_3$ or $C_2H_5$;
W' is O or S;
$R^3$ is $C_1-C_4$ alkyl, $C_1-C_4$ alkoxy, H, F, Cl, Br, $NO_2$, $SO_2MR^6R^7$, $SO_2N(OCH_3)CH_3$ or $C(O)R^4$;
$R^{20}$ is F, Cl, Br, $CO_2R^{17}$, $OSO_2R^9$, $NO_2$, $C_1-C_4$ alkyl or $C_1-C_4$ alkoxy;
W is O or S;
X is $CH_3$, $C_2H_5$, Cl, $OCH_3$, $OC_2H_5$, $N(CH_3)_2$ or $SCH_3$; and
Y is H, $CH_3$ or $C_2H_5$;
and their agriculturally suitable salts; provided that
 (a) when $R^{11}$ is $OCH_3$; then $R^{12}$ is $CH_3$;
 (b) if $R^1$ is other than H and R is H, then $R^1$ cannot be in the 4-position of the benzene ring;
 (c) when $R^{11}$ is

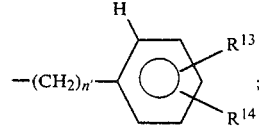

then $R^{12}$ is H or $CH_3$; and (d) when W' is O, then $R^3$ is $CO_2R^{17}$.

2. A compound of claim 1 where
W is O;
Y is $CH_3$;
X is other than Cl;
A is other than

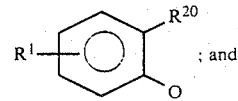
and
Z is H.

3. A compound of claim 2 where
X is $CH_3$ or $OCH_3$; and
A is

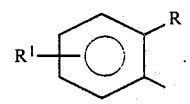

4. A compound of claim 2 where
X is $CH_3$ or $OCH_3$; and
A is

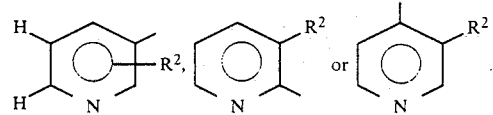

5. A compound of claim 2 where
X is $CH_3$ or $OCH_3$; and
A is

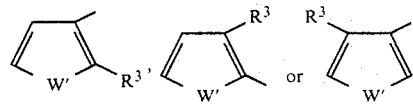

6. A compound of claim 3 where
R is $C_1-C_3$ alkyl, $OCH_3$, F, Cl, Br, $NO_2$, $CF_3$, $C(O)R^4$, $S(O)_mR^5$, $SO_2NR^6R^7$, $SO_2N(OCH_3)CH_3$, $BR^8$, $OSO_2R^9$ or $CH_2L$;
$R^4$ is H, $C_1-C_3$ alkyl, $C_1-C_4$ alkoxy, $C_3-C_4$ alkenyloxy, haloethoxy containing 1-3 atoms of F or Cl, $OCH_2CH_2OR^{10}$, $OCH_2CH_2CH_2OR^{10}$, $OCH_2OR^5$, $OCH_2OCH_2CH_2OR^{10}$, $NR^{11}R^{12}$ or $C_1-C_4$ alkylthio;
B is O;
L is $OCH_3$ or $CO_2R^{17}$;
$R^{11}$ is $C_1-C_4$ alkyl or $OCH_3$;
$R^{12}$ is $C_1-C_4$ alkyl; and
$R^{11}$ and $R^{12}$ can be taken together to form $-(CH_2)_4-$, $-(CH_2)_5-$ or $-CH_2CH_2OCH_2CH_2-$, provided that the total carbon atoms of $R^{11}$ and $R^{12}$ is less than or equal to 5.

7. A compound of claim 6 where
$R^1$ is H;
$R^4$ is $C_1-C_4$ alkoxy, $C_3-C_4$ alkenyloxy, $OCH_2CH_2Cl$ or $OCH_2CH_2OCH_3$;
$R^8$ is $CF_3$, $CH_2CF_3$ or $CF_2CHF_2$;
$R^9$ is $CH_3$; and
L is $OCH_3$.

8. A compound of claim 7 where
R is $NO_2$, $C(O)R^4$, $SO_2R^5$ or $SO_2N(CH_3)_2$;
$R^4$ is $C_1$-$C_3$ alkoxy; and
$R^5$ is $C_1$-$C_3$ alkyl.

9. A compound of claim 4 where
A is

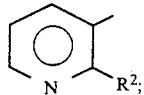
; ps and $R^2$ is Cl, Br, $CH_3$, $OCH_3$ or $S(O)_mCH_3$.

10. A compound of claim 5 where
W' is S;
$R^3$ is H, $CH_3$, Cl, Br or $C(O)R^4$; and
$R^4$ is $C_1$-$C_3$ alkoxy.

11. The compound of claim 1, 2-chloro-N-[(4,6-dimethylfuro[2,3-d]pyrimidin-2-yl)aminocarbonyl]benzenesulfonamide.

12. The compound of claim 1, N-[(4,6-dimethylfuro[2,3-d]pyrimidin-2-yl)aminocarbonyl]-2-nitrobenzenesulfonamide.

13. The compound of claim 1, 2-[(4,6-dimethylfuro[2,3-d]pyrimidin-2-yl)aminocarbonyl]aminosulfonyl benzoic acid, methyl ester.

14. The compound of claim 1, 2-[(4,6-dimethylfuro[2,3-d]pyrimidin-2-yl)aminocarbonyl]aminosulfonyl benzoic acid, (2-propenyl)ester.

15. The compound of claim 1, 2-[(4,6-dimethylfuro[2,3-d]pyrimidin-2-yl)aminocarbonyl]aminosulfonyl benzoic acid, (1-methylethyl)ester.

16. The compound of claim 1, 2-chloro-N-[(4,6-dimethylfuro[2,3-d]pyrimidin-2-yl)aminocarbonyl]-3-pyridinesulfonamide.

17. The compound of claim 1, 3-[(4,6-dimethylfuro[2,3-d]pyrimidin-2-yl)aminocarbonyl]aminosulfonyl-2-thiophenecarboxylate, methyl ester.

18. The compound of claim 1, N-[(4,6-dimethylfuro[2,3-d]pyrimidin-2-yl)aminocarbonyl]-3-methyl-2-thiophenesulfonamide.

19. The compound of claim 1, 4-[(4,6-dimethylfuro[2,3-d]pyrimidin-2-yl)aminocarbonyl]aminosulfonyl-3-thiophenecarboxylate, methyl ester.

20. The compound of claim 1, 2-[[(4,6-dimethylfuro[2,3-d]pyrimidin-2-yl)aminocarbonyl]aminosulfonyl]benzoic acid, ethyl ester.

21. The compound of claim 1, 2-[[(4-methoxy-6-methylfuro[2,3-d]pyrimidin-2-yl)aminocarbonyl]aminosulfonyl]benzoic acid, methyl ester.

22. The compound of claim 1, N-[(4,6-dimethylfuro[2,3-d]pyrimidin-2-yl)aminocarbonyl]-2-methylsulfonylbenzenesulfonamide.

23. The compound of claim 1, N'-[(4,6-dimethylfuro[2,3-d]pyrimidin-2-yl)aminocarbonyl]-N,N-dimethylbenzene-1,2-sulfonamide.

24. A compound selected from

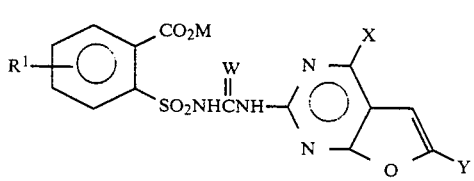

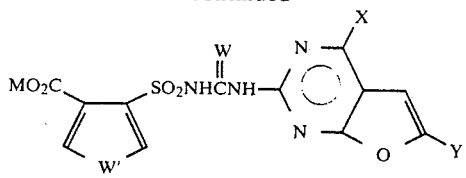

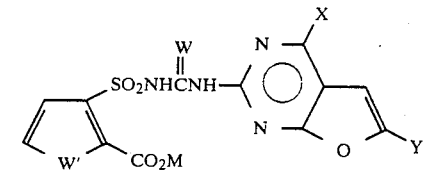

or

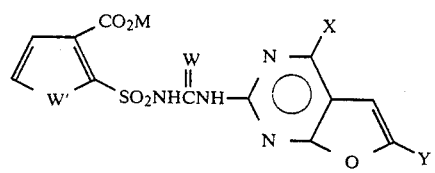

wherein
$R^1$ is H, F, Cl, Br, $CF_3$, $C_1$-$C_4$ alkyl or $C_1$-$C_4$ alkoxy;
M is H or an alkali metal;
W' is O or S;
W is O or S;
X is $CH_3$, $C_2H_5$, $OCH_3$ or $OC_2H_5$; and
Y is H, $CH_3$ or $C_2H_5$.

25. A composition suitable for controlling the growth of undesired vegetation which comprises an effective amount of a compound of claim 1 and at least one of the following: surfactant, solid or liquid diluent.

26. A composition suitable for controlling the growth of undesired vegetation which comprises an effective amount of a compound of claim 2 and at least one of the following: surfactant, solid or liquid diluent.

27. A composition suitable for controlling the growth of undesired vegetation which comprises an effective amount of a compound of claim 3 and at least one of the following: surfactant, solid or liquid diluent.

28. A composition suitable for controlling the growth of undesired vegetation which comprises an effective amount of a compound of claim 4 and at least one of the following: surfactant, solid or liquid diluent.

29. A composition suitable for controlling the growth of undesired vegetation which comprises an effective amount of a compound of claim 5 and at least one of the following: surfactant, solid or liquid diluent.

30. A composition suitable for controlling the growth of undesired vegetation which comprises an effective amount of a compound of claim 6 and at least one of the following: surfactant, solid or liquid diluent.

31. A composition suitable for controlling the growth of undesired vegetation which comprises an effective amount of a compound of claim 7 and at least one of the following: surfactant, solid or liquid diluent.

32. A composition suitable for controlling the growth of undesired vegetation which comprises an effective amount of the compound of claim 8 and at least one of the following: surfactant, solid or liquid diluent.

33. A method for controlling the growth of undesired vegetation which comprises applying to the locus to be protected an effective amount of a compound of claim 1.

34. A method for controlling the growth of undesired vegetation which comprises applying to the locus to be protected an effective amount of a compound of claim 2.

35. A method for controlling the growth of undesired vegetation which comprises applying to the locus to be protected an effective amount of a compound of claim 3.

36. A method for controlling the growth of undesired vegetation which comprises applying to the locus to be protected an effective amount of a compound of claim 4.

37. A method for controlling the growth of undesired vegetation which comprises applying to the locus to be protected an effective amount of a compound of claim 5.

38. A method for controlling the growth of undesired vegetation which comprises applying to the locus to be protected an effective amount of a compound of claim 6.

39. A method for controlling the growth of undesired vegetation which comprises applying to the locus to be protected an effective amount of a compound of claim 7.

40. A method for controlling the growth of undesired vegetation which comprises applying to the locus to be protected an effective amount of the compound of claim 8.

* * * * *